United States Patent
Franklin et al.

(10) Patent No.: US 10,368,872 B2
(45) Date of Patent: Aug. 6, 2019

(54) SYSTEM AND METHOD FOR LOW PROFILE OCCLUSION BALLOON CATHETER

(71) Applicant: Prytime Medical Devices, Inc., Boerne, TX (US)

(72) Inventors: Curtis J. Franklin, Lakewood, CO (US); Todd J. Krummenacher, Lakewood, CO (US); Jeremy Reynolds, Lakewood, CO (US); David Spencer, Boerne, TX (US); Luke William Fisher, Lakewood, CO (US)

(73) Assignee: Prytime Medical Devices, Inc., Boerne, TX (US)

( * ) Notice: Subject to any disclaimer, the term of this patent is extended or adjusted under 35 U.S.C. 154(b) by 0 days.

(21) Appl. No.: 15/573,054

(22) PCT Filed: Jun. 2, 2017

(86) PCT No.: PCT/US2017/035729
§ 371 (c)(1),
(2) Date: Nov. 9, 2017

(87) PCT Pub. No.: WO2017/210584
PCT Pub. Date: Dec. 7, 2017

(65) Prior Publication Data
US 2019/0076152 A1 Mar. 14, 2019

Related U.S. Application Data

(60) Provisional application No. 62/375,472, filed on Aug. 16, 2016, provisional application No. 62/353,388, (Continued)

(51) Int. Cl.
*A61B 17/12* (2006.01)
*A61M 25/10* (2013.01)
(Continued)

(52) U.S. Cl.
CPC .. *A61B 17/12136* (2013.01); *A61B 17/12036* (2013.01); *A61B 17/12109* (2013.01);
(Continued)

(58) Field of Classification Search
CPC ....... A61B 17/12109; A61B 17/12136; A61M 25/00; A61M 25/10; A61M 25/1002;
(Continued)

(56) References Cited

U.S. PATENT DOCUMENTS

| 2,156,289 A | 5/1939 | Hoy |
| 4,464,172 A | 8/1984 | Lichtenstein |

(Continued)

FOREIGN PATENT DOCUMENTS

| EP | 9834670 A2 | 8/1998 |
| EP | 1094861 B1 | 4/2005 |

(Continued)

OTHER PUBLICATIONS

Chen et al., "The Renal Length Nomogram: A Multivariable Approach," The Journal of Urology, vol. 168, pp. 2149-2152 (Nov. 2002).
(Continued)

*Primary Examiner* — George J Ulsh
(74) *Attorney, Agent, or Firm* — Panitch Schwarze Belisario & Nadel LLP

(57) ABSTRACT

An occlusion catheter system includes an inflation catheter member and an occlusion balloon. The proximal and distal balloon ends are connected to the inflation catheter between the proximal and distal catheter ends. A distal pressure sensor is attached to the inflation catheter member between the proximal balloon end and the atraumatic tip. An inflatable spine is connected to the inflation catheter. The proximal spine end is connected to the inflation catheter near the proximal balloon end and the distal spine end is connected to the inflation catheter near the distal balloon end. The
(Continued)

occlusion balloon and the inflatable spine are configured to define blood flow channels with the internal surface and the external balloon surface when the occlusion catheter system is at least partially positioned in the vessel and the occlusion balloon and the inflatable spine are in a partially inflated configuration.

25 Claims, 30 Drawing Sheets

Related U.S. Application Data filed on Jun. 22, 2016, provisional application No. 62/344,699, filed on Jun. 2, 2016.

(51) Int. Cl.
*A61M 25/00* (2006.01)
*A61M 25/02* (2006.01)
*A61B 17/22* (2006.01)

(52) U.S. Cl.
CPC ........ *A61M 25/00* (2013.01); *A61M 25/0068* (2013.01); *A61M 25/02* (2013.01); *A61M 25/10* (2013.01); *A61M 25/1002* (2013.01); *A61M 25/104* (2013.01); *A61M 25/1011* (2013.01); *A61M 25/10184* (2013.11); *A61B 2017/22051* (2013.01); *A61B 2017/22055* (2013.01); *A61M 2025/0002* (2013.01); *A61M 2025/0003* (2013.01); *A61M 2025/024* (2013.01); *A61M 2025/028* (2013.01); *A61M 2025/0286* (2013.01); *A61M 2025/1052* (2013.01); *A61M 2025/1056* (2013.01); *A61M 2025/1061* (2013.01); *A61M 2025/1084* (2013.01); *A61M 2025/1088* (2013.01); *A61M 2025/1095* (2013.01)

(58) Field of Classification Search
CPC ........ A61M 25/104; A61M 2025/1052; A61M 2025/1093
See application file for complete search history.

(56) References Cited

U.S. PATENT DOCUMENTS

| | | |
|---|---|---|
| 4,713,888 A | 12/1987 | Broselow |
| 4,777,951 A | 10/1988 | Cribier et al. |
| 4,823,469 A | 4/1989 | Broselow |
| 4,865,549 A | 9/1989 | Sonsteby |
| 4,926,885 A | 5/1990 | Hinkle |
| 4,983,166 A | 1/1991 | Yamawaki |
| 5,135,494 A | 8/1992 | Engelson et al. |
| 5,169,386 A | 12/1992 | Becker et al. |
| 5,282,479 A | 2/1994 | Havran |
| 5,320,605 A | 6/1994 | Sahota |
| 5,383,856 A | 1/1995 | Bersin |
| 5,447,503 A | 9/1995 | Miller |
| 5,505,702 A | 4/1996 | Arney |
| 5,522,400 A | 6/1996 | Williams |
| 5,571,093 A | 11/1996 | Cruz et al. |
| 5,718,678 A | 2/1998 | Fleming, III |
| 5,738,652 A | 4/1998 | Boyd et al. |
| 5,911,702 A | 6/1999 | Romley et al. |
| 6,011,988 A | 1/2000 | Lynch et al. |
| 6,013,019 A | 1/2000 | Fischell et al. |
| 6,102,930 A | 8/2000 | Simmons, Jr. |
| 6,113,579 A | 9/2000 | Eidenschink et al. |
| 6,146,370 A | 11/2000 | Barbut |
| 6,161,547 A | 12/2000 | Barbut |
| 6,165,199 A | 12/2000 | Barbut |
| 6,190,356 B1 | 2/2001 | Bersin |
| 6,231,572 B1 | 5/2001 | Hart et al. |
| 6,248,121 B1 | 6/2001 | Nobles |
| 6,280,434 B1 | 8/2001 | Kinoshita et al. |
| 6,423,031 B1 | 7/2002 | Donlon |
| 6,453,572 B2 | 9/2002 | Cross et al. |
| 6,575,932 B1 | 6/2003 | O'Brien et al. |
| 6,579,221 B1 | 6/2003 | Peterson |
| 6,602,270 B2 | 8/2003 | Leschinsky et al. |
| 6,656,153 B1 | 12/2003 | Sakai et al. |
| 6,666,814 B2 | 12/2003 | Downey et al. |
| 6,669,679 B1 | 12/2003 | Savage et al. |
| 6,679,860 B2 | 1/2004 | Stiger |
| 6,695,811 B2 | 2/2004 | Samson et al. |
| 6,719,270 B2 | 4/2004 | Ozawa |
| 6,719,720 B1 | 4/2004 | Voelker et al. |
| 6,733,513 B2 | 5/2004 | Boyle et al. |
| 6,735,532 B2 | 5/2004 | Freed et al. |
| 6,736,790 B2 | 5/2004 | Barbut et al. |
| 6,746,462 B1 | 6/2004 | Selmon et al. |
| 6,796,959 B2 | 9/2004 | Davis et al. |
| 6,936,056 B2 | 8/2005 | Nash et al. |
| 6,979,318 B2 | 12/2005 | McDonald et al. |
| 7,341,571 B1 | 3/2008 | Harris et al. |
| 7,434,326 B2 | 10/2008 | Gifford |
| 7,503,904 B2 | 3/2009 | Choi |
| 7,503,909 B2 | 3/2009 | Kusu et al. |
| 7,763,043 B2 | 7/2010 | Goodin et al. |
| 7,892,469 B2 | 2/2011 | Lim et al. |
| 7,909,810 B2 | 3/2011 | Noone |
| 7,951,186 B2 | 5/2011 | Eidenschink et al. |
| 7,951,819 B2 | 5/2011 | Niculescu-Duvaz et al. |
| 7,959,644 B2 | 6/2011 | Shriver |
| 8,088,103 B2 | 1/2012 | Teeslink et al. |
| 8,162,879 B2 | 4/2012 | Hattangadi et al. |
| 8,241,241 B2 | 8/2012 | Evans et al. |
| 8,262,611 B2 | 9/2012 | Teeslink et al. |
| 8,419,648 B2 | 4/2013 | Corl et al. |
| 8,430,899 B2 | 4/2013 | Dae et al. |
| 8,499,681 B2 | 8/2013 | Kanner et al. |
| 8,545,382 B2 | 10/2013 | Suzuki et al. |
| 8,647,376 B2 * | 2/2014 | Arcand .......... A61F 2/958 623/1.11 |
| 8,655,798 B2 | 2/2014 | Humphrey et al. |
| 8,672,868 B2 | 3/2014 | Simons |
| 8,747,358 B2 | 6/2014 | Trombley, III et al. |
| 8,814,900 B2 | 8/2014 | Fleming, III |
| 8,900,214 B2 | 12/2014 | Nance et al. |
| 8,948,848 B2 | 2/2015 | Merhi |
| 8,951,565 B2 | 2/2015 | McCarthy |
| 9,131,874 B2 | 9/2015 | Eliason et al. |
| D748,257 S | 1/2016 | Franklin |
| 9,414,843 B2 | 8/2016 | Pavcnik et al. |
| 9,474,882 B2 | 10/2016 | Franklin |
| 9,687,333 B2 | 6/2017 | Angel et al. |
| 2002/0193735 A1 | 12/2002 | Stiger |
| 2003/0032974 A1 | 2/2003 | Leschinsky et al. |
| 2003/0167038 A1 | 9/2003 | Yozu et al. |
| 2004/0073162 A1 | 4/2004 | Bleam et al. |
| 2004/0082935 A1 | 4/2004 | Lee et al. |
| 2004/0254528 A1 | 12/2004 | Adams et al. |
| 2005/0059931 A1 | 3/2005 | Garrison et al. |
| 2005/0148812 A1 | 7/2005 | Nigroni et al. |
| 2005/0261725 A1 | 11/2005 | Crawford et al. |
| 2007/0043307 A1 | 2/2007 | Raulerson et al. |
| 2007/0043409 A1 | 2/2007 | Brian et al. |
| 2007/0129466 A1 | 6/2007 | Kagawa et al. |
| 2007/0135830 A1 | 6/2007 | Schaeffer |
| 2007/0219466 A1 | 9/2007 | Tremulis et al. |
| 2007/0219488 A1 | 9/2007 | Francescatti |
| 2008/0027356 A1 | 1/2008 | Chen et al. |
| 2008/0082046 A1 | 4/2008 | Kato et al. |
| 2008/0082119 A1 | 4/2008 | Vitullo |
| 2008/0243067 A1 | 10/2008 | Rottenberg et al. |
| 2008/0262477 A1 | 10/2008 | Djaladat |
| 2009/0026595 A1 | 1/2009 | Kadoi |
| 2009/0062666 A1 | 3/2009 | Roteliuk |
| 2009/0171272 A1 | 7/2009 | Tegg et al. |
| 2009/0171293 A1 | 7/2009 | Yang et al. |
| 2009/0265951 A1 | 10/2009 | Black |
| 2009/0287079 A1 | 11/2009 | Shriver |

(56) References Cited

U.S. PATENT DOCUMENTS

| | | |
|---|---|---|
| 2009/0312807 A1 | 12/2009 | Boudreault et al. |
| 2010/0016735 A1 | 1/2010 | Harpas et al. |
| 2010/0041984 A1 | 2/2010 | Shapland et al. |
| 2010/0234915 A1 | 9/2010 | Herlich et al. |
| 2010/0262076 A1 | 10/2010 | Rowe et al. |
| 2010/0268017 A1 | 10/2010 | Siess |
| 2010/0280451 A1 | 11/2010 | Teeslink et al. |
| 2011/0196412 A1 | 8/2011 | Levit et al. |
| 2011/0295301 A1 | 12/2011 | Hoem et al. |
| 2011/0295302 A1 | 12/2011 | Mohl |
| 2011/0301630 A1 | 12/2011 | Hendriksen et al. |
| 2012/0101413 A1 | 4/2012 | Beetel et al. |
| 2012/0108979 A1 | 5/2012 | Franklin et al. |
| 2012/0109057 A1 | 5/2012 | Krolik et al. |
| 2012/0116352 A1 | 5/2012 | Rangi |
| 2012/0130359 A1 | 5/2012 | Turovskiy |
| 2012/0172911 A1 | 7/2012 | Welch |
| 2012/0215166 A1 | 8/2012 | Barki |
| 2012/0271231 A1 | 10/2012 | Agrawal |
| 2012/0302994 A1 | 11/2012 | Wilson et al. |
| 2013/0102926 A1 | 4/2013 | Eliason et al. |
| 2013/0102929 A1 | 4/2013 | Haight et al. |
| 2013/0190619 A1 | 7/2013 | Nudel |
| 2013/0281869 A1 | 10/2013 | Barbut et al. |
| 2013/0289607 A1 | 10/2013 | Pedersen et al. |
| 2014/0221898 A1 | 8/2014 | Kurrus et al. |
| 2014/0243873 A1 | 8/2014 | Franklin |
| 2014/0249504 A1 | 9/2014 | Franklin et al. |
| 2014/0316012 A1 | 10/2014 | Freyman et al. |
| 2014/0378869 A1 | 12/2014 | Sela et al. |
| 2015/0012031 A1 | 1/2015 | Rago et al. |
| 2015/0039012 A1 | 2/2015 | Solar et al. |
| 2015/0367098 A1 | 12/2015 | Aggerholm et al. |
| 2016/0000446 A1 | 1/2016 | Eliason et al. |

FOREIGN PATENT DOCUMENTS

| | | |
|---|---|---|
| EP | 1658808 A1 | 5/2006 |
| EP | 1911484 A2 | 4/2008 |
| EP | 2389974 A1 | 11/2011 |
| EP | 2716323 A1 | 4/2014 |
| GB | 2297259 | 7/1996 |
| JP | H 03198868 A | 8/1991 |
| JP | H 09-164208 A | 6/1997 |
| JP | 2002505165 A | 2/2002 |
| JP | 2003535652 A | 12/2003 |
| JP | 200714820 A | 1/2007 |
| JP | 2008546471 A | 12/2008 |
| JP | 2011245300 A | 12/2011 |
| WO | 9220398 A1 | 11/1992 |
| WO | 9713542 A1 | 4/1997 |
| WO | 1999/24105 A2 | 5/1999 |
| WO | 9944666 A2 | 9/1999 |
| WO | 0197743 A2 | 12/2001 |
| WO | 2004049970 A2 | 6/2004 |
| WO | 2006135853 A2 | 12/2006 |
| WO | 2007001701 A1 | 1/2007 |
| WO | 2007022592 A1 | 3/2007 |
| WO | 2008013441 A1 | 1/2008 |
| WO | 2010070685 A1 | 6/2010 |
| WO | 2011133736 A2 | 10/2011 |
| WO | 2014/003809 A1 | 1/2014 |
| WO | 2014134215 A1 | 9/2014 |
| WO | 2014152191 A1 | 9/2014 |
| WO | 2015/006828 A1 | 1/2015 |
| WO | 2015035393 A1 | 3/2015 |
| WO | 2015191685 A1 | 12/2015 |
| WO | 2016149653 A2 | 9/2016 |

OTHER PUBLICATIONS

Int'l Search Report and Written Opinioin dated Sep. 28, 2017 in Int'l Application No. PCT/US2017/035729.

Holcomb et al., "Causes of death in US Special Operations Forces in the global war on terrorism: 2001-2004," Annals of Surgery, vol. 245, No. 6, pp. 986-991 (2007).

Sohn et al., "Demographics, Treatment, and Early Outcomes in Penetrating Vascular Combat Trauma," Arch Surg, vol. 143, No. 8, pp. 783-787 (2008).

White et al., "The Epidemiology of Vascular Injury in the Wars in Iraq and Afghanistan," Annals of Surgery, vol. 253, No. 6, pp. 1184-1189 (2011).

Fenton et al., "Comparing risks of alternative medical diagnosis using Bayesian arguments," J. Biomed. Inf., vol. 43, pp. 485-495 (2010).

Patel et al., "Bayesian Designs for Device Clinical Trials," MDG Forum, Waltham, MA., Nov. 3, 2010, downloaded from web page: <http://www.cytel.com/pdfs/Patel_Bayes_Devices_Slides_11.18.10.pdf>.

Guidance for the Use of Bayesian Statistics in Medical Device Clinical Trials, U.S. Department of Health and Human Services, Food and Drug Administration, Center for Devices and Radiological Health, Division of Biostatistics, Office of Surveillance and Biometrics, Feb. 5, 2010.

Int'l Preliminary Report on Patentability dated Sep. 11, 2015 in Int'l Application No. PCT/US2014/018779.

Int'l Search Report and Written Opinion dated Jun. 8, 2014 in Int'l Application No. PCT/US2014/018779.

Int'l Search Report and Written Opinion dated Oct. 14, 2011 in Int'l Application No. PCT/US2011/033368.

Sandgren et al., "The Diameter of the Common Femoral Artery in Healthy Human: Influence of Sex, Age, and Body Size," Journal of Vascular Surgery, vol. 29, No. 3, pp. 503-510 (1999).

Sam Il et al., "Blunt Traumatic Aortic Transection: Endoluminal Repair with Commercially Available Aortic Cuffs," Journal of Vascular Surgery, vol. 38, No. 5, pp. 1132-1135 (2003).

Peterson et al., "Percutaneous endovascular repair of blunt thoracic aortic transection," Journal of Trauma, vol. 59, No. 5, pp. 1062-1065 (2005).

Office Action dated Oct. 28, 2014 in U.S. Appl. No. 13/642,465, by Eliason.

Office Action dated Apr. 6, 2015 in U.S. Appl. No. 13/642,465, by Eliason.

Stannard et al., "Resuscitative Endovascular Balloon Occlusion of the Aorta (REBOA) as an Adjunct for Hemorrhagic Shock," J. Trauma, vol. 71, pp. 1869-1872 (2011).

Ledgerwood et al., "The Role of Thoracic Aortic Occlusion for Massive Hemoperitoneum," J Trauma, vol. 16, No. 3, pp. 610-615 (1976).

Detrano et al. "Bayesian Probability Analysis: a Prospective Demonstration of its Clinical Utility in Diagnosing Coronary Disease," Circulation, vol. 69, No. 3, pp. 541-547 (1984).

Int'l Search Report and Written Opinion dated Jan. 28, 2015 in Int'l Application No. PCT/US2014/054802.

Int'l Preliminary Report on Patentability dated Mar. 24, 2016 in Int'l Application No. PCT/US2014/054802.

Int'l Preliminary Report on Patentability dated Nov. 1, 2012 in Int'l Application No. PCT/US2011/033368.

Langewouters et al., "The static elastic properties of 45 human thoracic and 20 abdominal aortas in vitra and the parameters of a new model," Journal of Biometrics, vol. 17, No. 6, pp. 425-435 (1984).

Hughes, "Use of an Intra-Aortic Balloon Catheter Tamponade for Controlling Intra-Abdominal Hemorrhage in Man," Surgery, vol. 36, pp. 65-68 (1954).

Office Action dated Aug. 23, 2016 in AU Application No. 2015274743.

Extended European Search Report dated Oct. 5, 2016 in Europe Application No. EP 14 75 6640.

Supplemental Search Report dated Dec. 19, 2016 in EP Application No. 15806534.

Int'l Preliminary Report dated Dec. 22, 2016 in Int'l Application No. PCT/US2015/035061.

Int'l Search Report and Written Opinion dated Sep. 4, 2015 in Int'l Application No. PCT/US2014/035061.

Extended Search Report dated Mar. 24, 2017 in EP Application No. 14842370.

(56) References Cited

OTHER PUBLICATIONS

Int'l Search Report and Written Opinion dated Apr. 21, 2017 in Int'l Application No. PCT/US2016/023223.
Extended Search Report dated Mar. 21, 2017 in EP Application No. 15806534.
Office Action dated Apr. 11, 2017 in JP Application No. 2016-546035.
Office Action dated Mar. 20, 2017 in CA Application No. 2,797,237.
Extended European Search Report dated Jun. 26, 2017 in EP Application No. 14842370.
Int'l Preliminary Report dated Jul. 17, 2017 in Int'l Application No. PCT/US2016/023223.
Office Action dated Sep. 19, 2017 in JP Application No. 2015-559309.
Office Action dated Sep. 12, 2017 in JP Application No. 2016-546035.
Office Action dated Oct. 12, 2017 in CA Application No. 2,980,018.

* cited by examiner

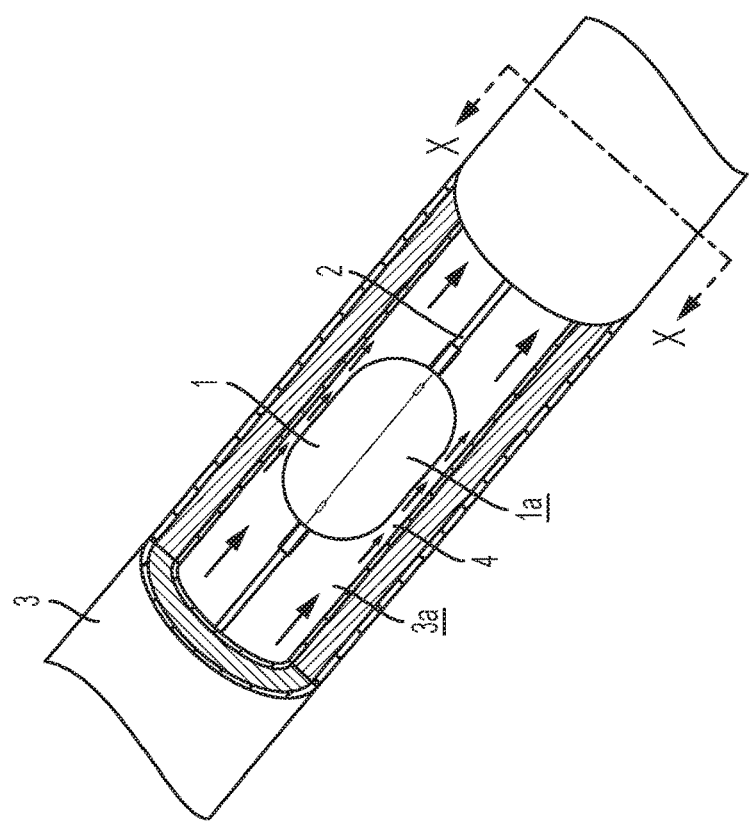
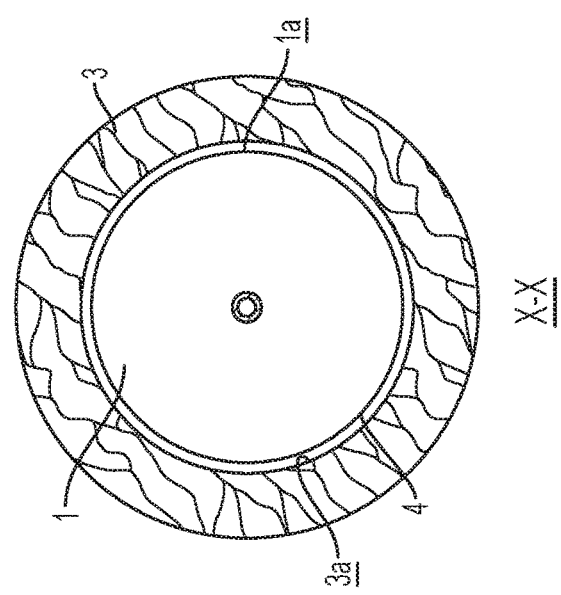
Fig 1PA
PRIOR ART

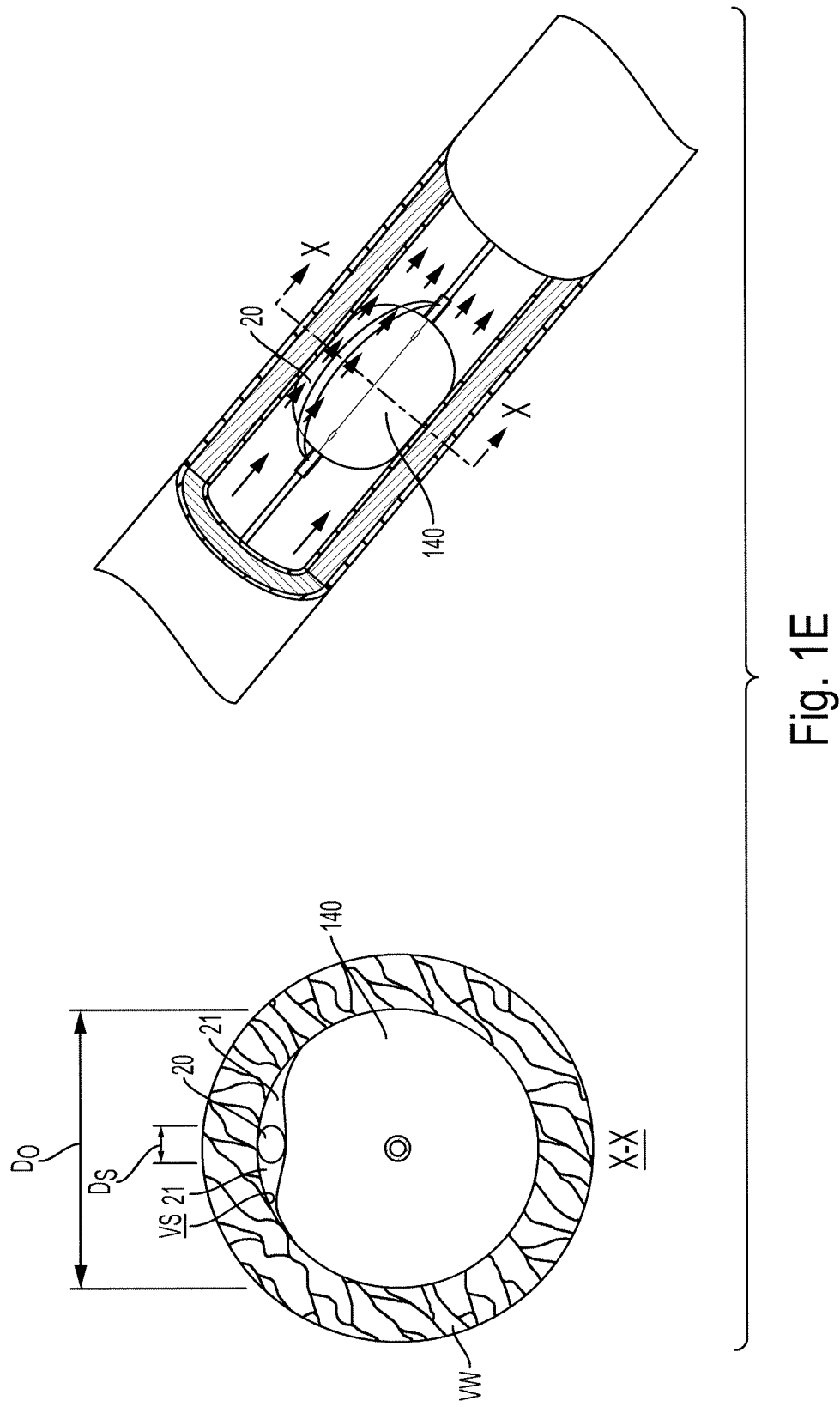

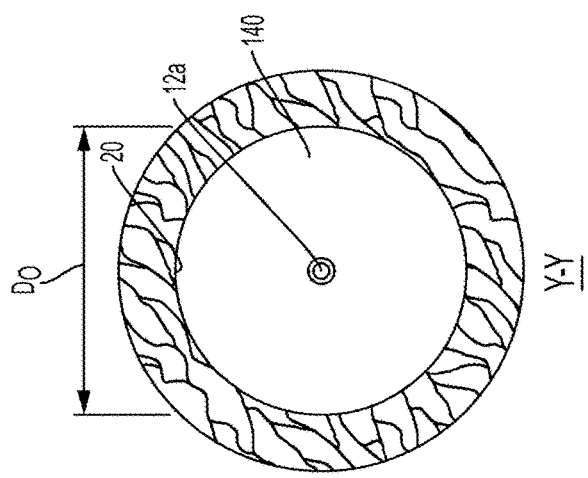
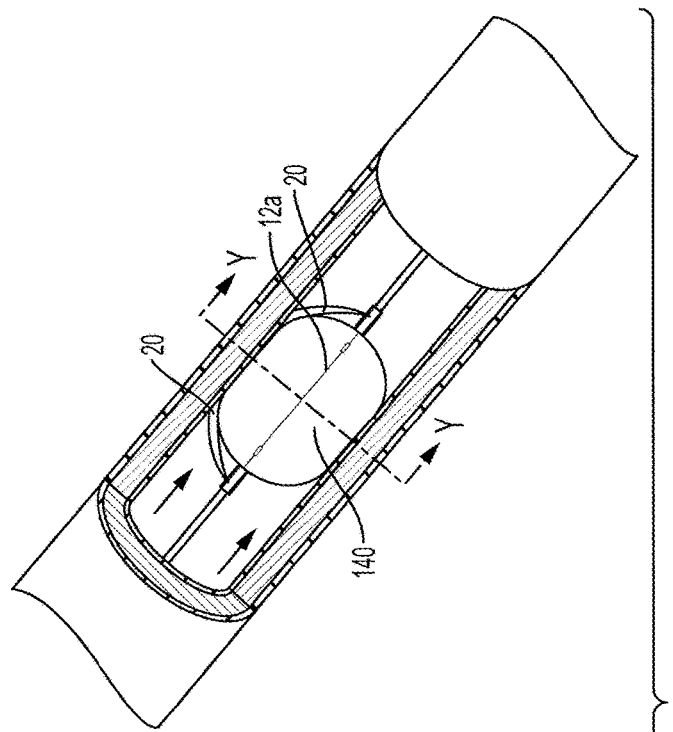
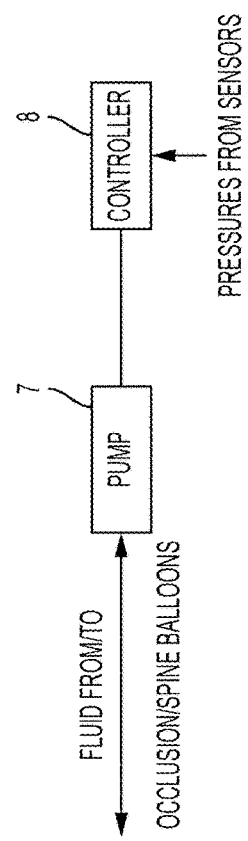
Fig. 1F
Fig. 1G

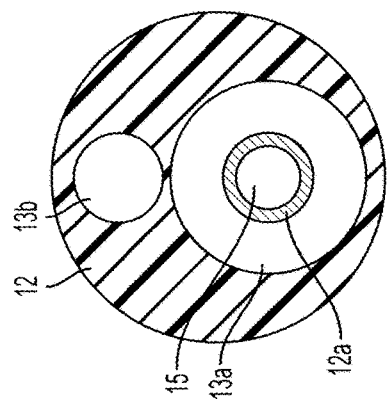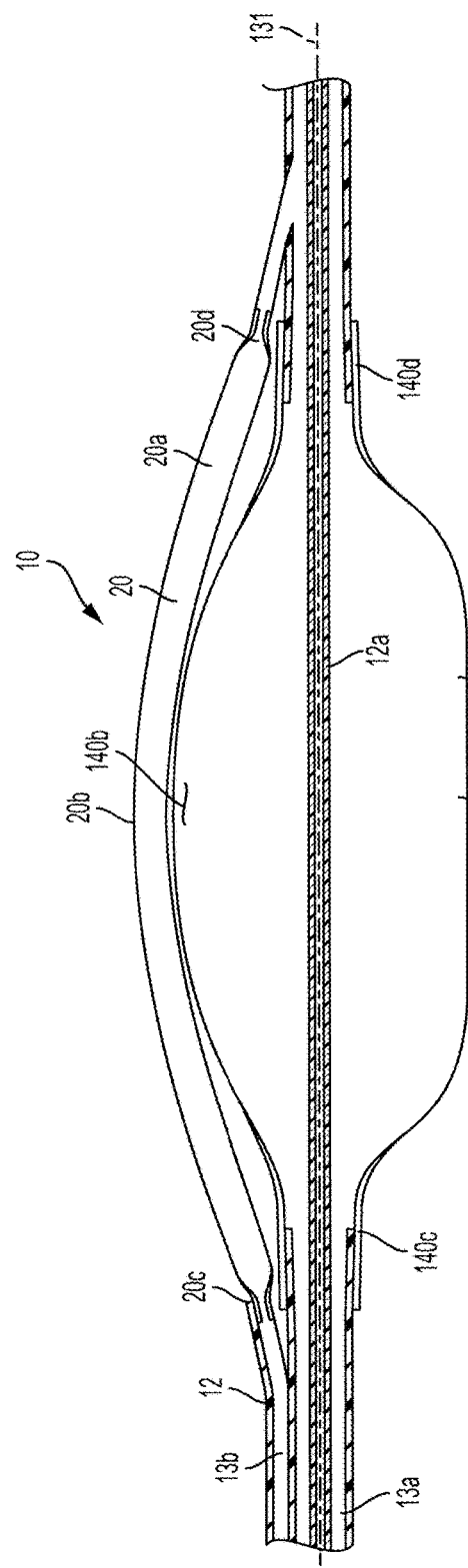

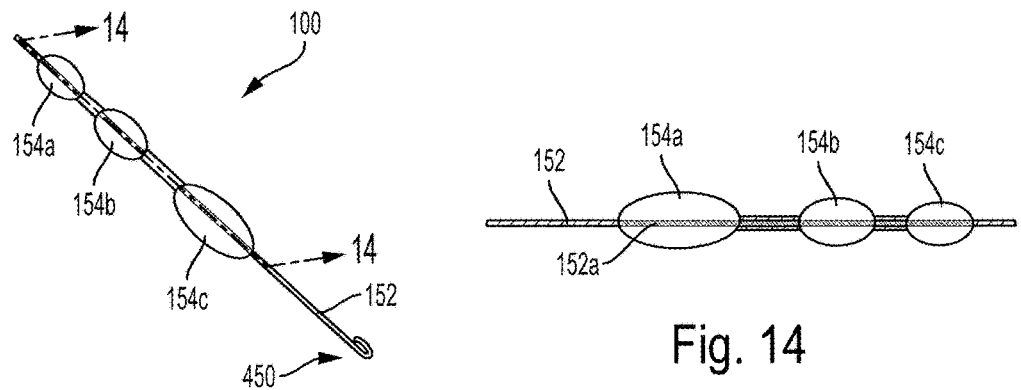
Fig. 13
Fig. 14
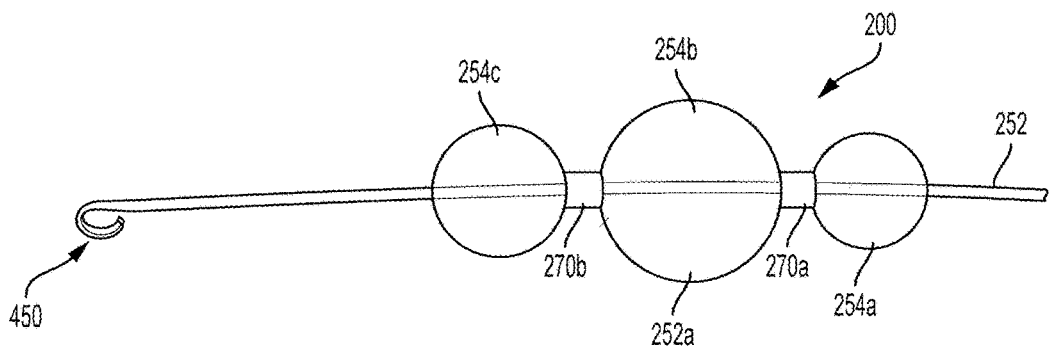
Fig. 15
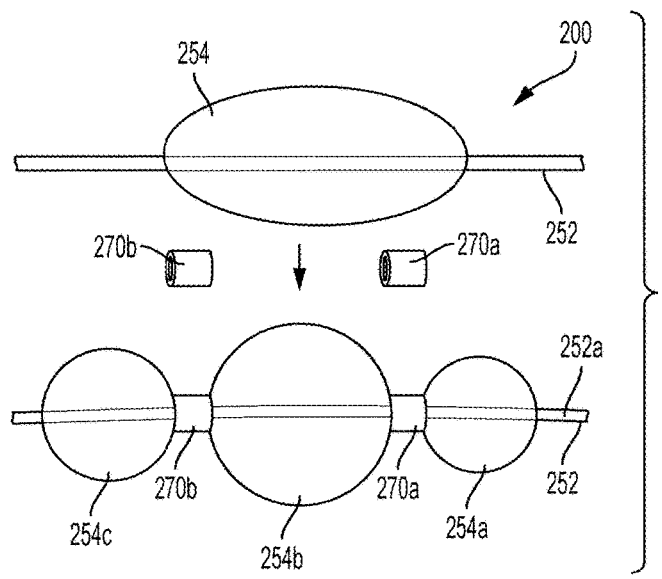
Fig. 16

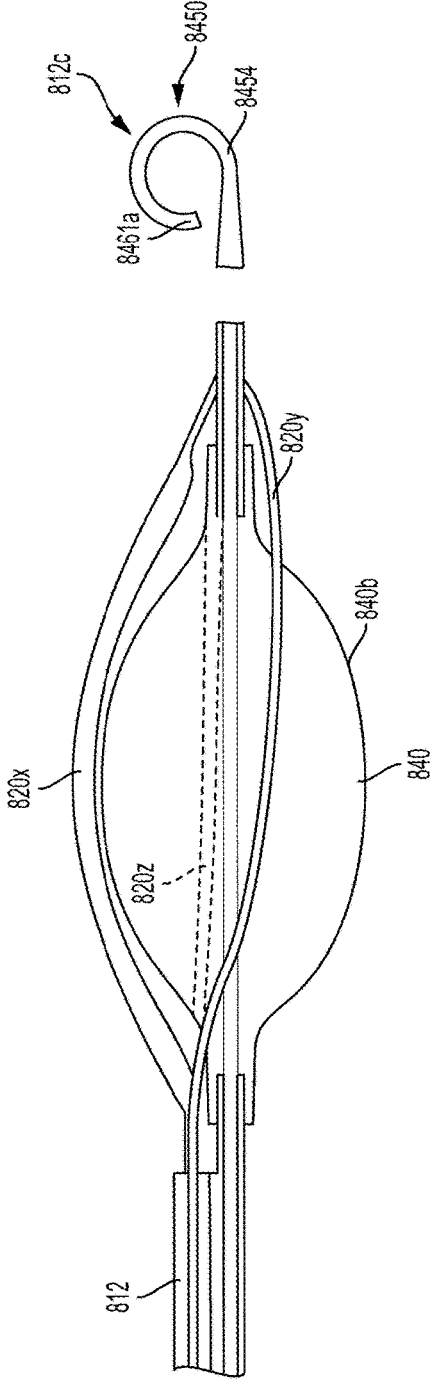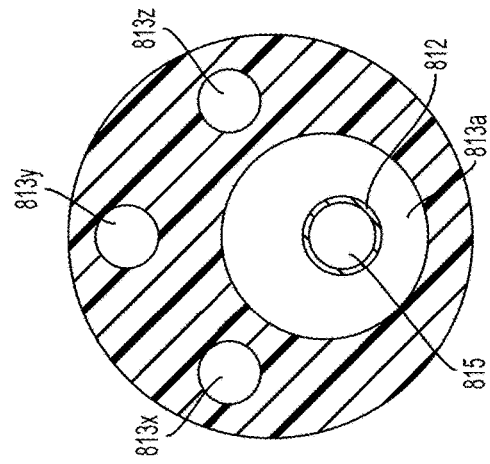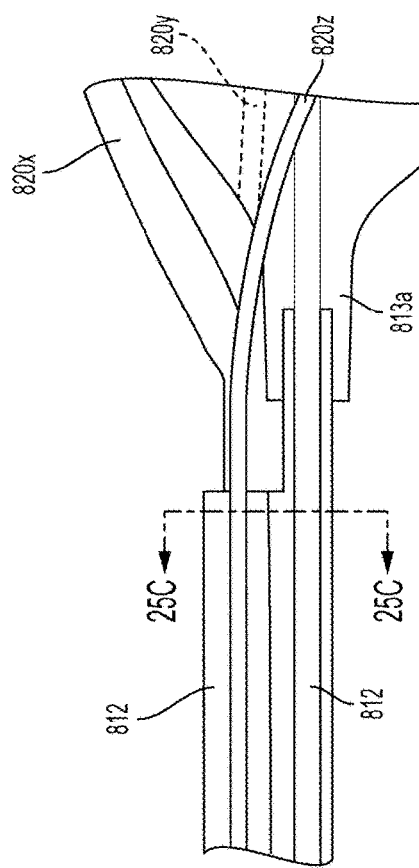
Fig. 25A
Fig. 25B
Fig. 25C

US 10,368,872 B2

SYSTEM AND METHOD FOR LOW PROFILE OCCLUSION BALLOON CATHETER

CROSS-REFERENCE TO RELATED APPLICATIONS

The present application is a Section 371 national phase of International Patent Application No. PCT/US2017/035729, filed Jun. 2, 2017, titled, "System and Method for Low-Profile Occlusion Balloon Catheter" and claims the benefit of U.S. Provisional Patent Application No. 62/375,472, filed on Aug. 16, 2016 and titled, "System and Method for Low Profile Occlusion Balloon Catheter," U.S. Provisional Patent Application No. 62/344,699, filed on Jun. 2, 2016 and titled, "System and Method for Low Profile Occlusion Balloon Catheter" and U.S. Provisional Patent Application No. 62/353,388, filed Jun. 22, 2016 and titled, "System and Method for Low-Profile Occlusion Balloon Catheter," the entire contents of which are incorporated herein by reference in their entirety.

STATEMENT REGARDING FEDERALLY SPONSORED RESEARCH OR DEVELOPMENT

This invention was made with government support under Contract No. W911QY-15-C-0099 awarded by U.S. Army Medical Materiel Agency. The government has certain rights in the invention.

BACKGROUND OF THE INVENTION

The present invention pertains generally to vascular occlusion catheters and methods of vascular pre-conditioning while controlling occlusion and perfusion during an occlusion procedure. Pre-conditioning is employed to mitigate ischemia before, during and/or after a vascular occlusion procedure, as well as used to reduce or ameliorate the onset of hypertension during or reduce or ameliorate the onset of hypotension after a vascular occlusion procedure. Vascular occlusions may be indicated in either the venous system and/or the arterial system. Endoarterial occlusion is a procedure in which a blood vessel is at least partially occluded in order to restrict blood flow upstream or downstream of the occlusion site for purposes of a vascular procedure or repair. It is known that transient hypertension is a risk factor in arterial occlusion, particularly aortic occlusion. Transient hypertension occurs when the blood pressure upstream of the occlusion site rises to a potentially unsafe level during the time duration of the occlusion. Upon completion of a procedure requiring arterial occlusion, particularly aortic occlusion, care must be taken during the process of reestablishing blood flow to reduce or ameliorate the onset of hypotension. Thus, arterial occlusion carries with it two twin risks, hypertension during the occlusion and hypotension as the occlusion is withdrawn and blood flow restored that must be managed.

In addition to hypotension and hypertension, techniques allowing partial flow of blood and related fluids past the occlusion member may be desirable to provide at least partial blood flow to portions of the patient's body downstream of the occlusion member. At least partial perfusion past the occlusion member can provide the benefits of focusing or directing a majority of blood flow to the brain, heart and lungs or other upstream portions of the patient, but also potentially increasing the amount of time the occlusion member can be implanted in the patient, by providing at least partial blood flow to the patient's organs downstream of the occlusion member, such as to the patient's liver, digestive tract, kidneys and legs.

Referring to Fig. A, partial perfusion may be accomplished by reducing the size of an occlusion member or occlusion balloon 1 that is attached to a catheter 2. The occlusion balloon 1 may, for example, be partially deflated to allow blood to flow between outer surfaces 1a of the occlusion balloon 1 and inner surfaces 3a of a vessel 3 within which the occlusion balloon 1 is positioned. This, for example, deflation of the occlusion balloon 1 may cause the occlusion balloon 1 to lose contact with the inner surface 3a of the vessel 3, thereby causing movement of the occlusion balloon 1 and partial vibration between the vessel 3 and the occlusion balloon 1 that is undesirable. Such loss of contact with the inner surfaces 3a of the vessel 3 by the occlusion balloon 1 is represented in Fig. A, by a cylindrical channel 4 defined between the outer surface 1a of the occlusion balloon 1 and the inner surfaces 3a of the vessel 3. Loss of contact with the inner surface 3a of the vessel 3 by the occlusion balloon 1 may also result in the occlusion balloon 1 and attached catheter 2 being urged downstream in the vessel 3, thereby moving the occlusion balloon 1 out of its preferred placement. It would be desirable to design, develop and implement an occlusion balloon catheter that maintains contact with the vessel during partial perfusion to reduce or eliminate such vibrations and movement of the occlusion member during partial perfusion.

Temporary aortic occlusion as an operative method to increase proximal or central perfusion to the heart and brain in the setting of shock due to major trauma is generally known. Despite potential advantages over thoracotomy with aortic clamping, resuscitative endovascular balloon occlusion of the aorta ("REBOA") for trauma has not been widely adopted.

Many attempts have been made at developing technologies to control non-compressible abdominal hemorrhage. For example, non-occlusive, abdominal tamponade procedures have been developed to address the problem of non-compressible hemorrhage, such as introducing an expandable, biocompatible foam into the abdominal cavity to apply pressure to the abdominal organs and vasculature. Pharmacological efforts have also been developed to address the problem of non-compressible hemorrhage. Conventional REBOA procedures are typically performed in an operating room and with the aid of fluoroscopy or other imaging.

Devices that automate inflation and deflation of a balloon are generally known. Intra-aortic balloon counterpulsation catheters for blood pressure augmentation coordinated with electrocardiography signals are also known. Over-inflation safety devices are also known, such as a pressure-relief valve coupled to an inflation lumen that opens when pressure within the inflation lumen exceeds a threshold pressure, but relative pressure within the occlusion balloon is necessary to maintain occlusion of the blood vessel.

It would be desirable to design, develop and implement a system that intermittently and automatically releases an occlusion balloon or member by releasing apposition of the occlusion balloon or member against the vascular wall and allowing perfusion past the occlusion balloon or member in response to a physiological parameter, then re-establishing occlusion in response to potential changes in the physiological parameter, either during a vascular repair procedure to control hypertension or post-repair procedure to control hypotension. It would also be desirable to design, develop and implement a system that allows perfusion past the occlusion balloon or member while maintaining engagement between the occlusion balloon or member and the walls of the vasculature, preferably an artery and more preferably the aorta, to prevent vibration, movement, sliding or shifting of the occlusion balloon or member as blood flows past the occlusion balloon. In addition, it is desirable to design, develop and implement an occlusion balloon that permits relatively fine control of a pressure ratio between proximal and distal sides of the occlusion balloon and, therefore, relatively fine control of blood flow across the occlusion balloon through the vessel. The preferred embodiments of the present invention addresses certain of these limitations of the prior art occlusion systems.

In addition, it is desirable to design, develop and implement an occlusion balloon that permits relatively fine control of a pressure ratio between proximal and distal sides of the occlusion balloon and, therefore, relatively fine control of blood flow across the occlusion balloon through the vessel. Existing occlusion balloons are difficult to modulate pressure drop across the balloon. A relatively small change in balloon volume or internal pressure often results in drastic changes in blood pressure between proximal and distal sides of the occlusion balloon, resulting in full occlusion or a relatively high rate of volumetric blood flow across the balloon. It is desirable to design, develop and deploy an occlusion system that is less sensitive to slight pressure changes in the occlusion balloon and provides a more gradual change in blood flow past the occlusion balloon. The preferred present invention addresses these shortcomings of prior art occlusion balloons.

BRIEF SUMMARY OF THE INVENTION

An occlusion catheter system for occlusion or partial occlusion of a relatively large vessel includes an inflation catheter member, an occlusion balloon and an inflatable spine. The inflation catheter member includes a stiffener member, a first inflation lumen and a second inflation lumen. The inflation catheter member has a proximal catheter end and a distal catheter end and defines a longitudinal axis. The occlusion balloon has an internal balloon space, an external balloon surface, a proximal balloon end and a distal balloon end. The proximal and distal balloon ends are connected to the inflation catheter. The first inflation lumen is in fluid communication with the internal balloon space. The inflatable spine has an internal spine space, an external spine surface, a proximal spine end and a distal spine end. The proximal and distal spine ends are connected to the inflation catheter. The second inflation lumen is in fluid communication with the internal spine space. A portion of the external balloon surface contacts the external spine surface when the occlusion balloon and the inflatable spine are in an inflated configuration. The proximal spine end is connected to the inflation catheter near the proximal balloon end and the distal spine end is connected to the inflation catheter near the distal balloon end.

The preferred occlusion catheter system is intended to give the user or medial professional a means of full occlusion, as well as a smooth-controlled partial occlusion. Current technology is limited in terms of partial occlusion because as the user withdraws fluid from the balloon to move from full occlusion to partial occlusion there is a sudden increase in blood flow across the balloon. The preferred embodiments of the occlusion catheter system mitigate this sudden change by creating flow paths of blood flow channels for the blood allowing the user or medical professional to more precisely control the flow by hand with a syringe, such as by controlling the inflation volume of the occlusion balloon. Current technology utilizing a single occlusion balloon with a smooth, continuous shape can become unstable, vibrate and pulse during partial occlusion because of minimal contact between the vessel wall and the external surfaces of the balloon. The preferred occlusion catheter systems provide constant contact of the balloon to the vessel wall during partial occlusion, thereby deescalating the vibrating and pulsing effects of conventional occlusion balloons and systems.

In a preferred embodiment, the present invention is directed to an occlusion catheter system for occlusion or partial occlusion of a relatively large vessel having an internal surface. The occlusion catheter system includes an inflation catheter member having a stiffener member, an occlusion balloon, a distal pressure sensor, and an inflatable spine. The inflation catheter member also includes a first inflation lumen, a proximal catheter end and a distal catheter end. The inflation catheter member defines a longitudinal axis and the inflation catheter member has an atraumatic tip on the distal catheter end. The occlusion balloon has an internal balloon space, an external balloon surface, a proximal balloon end and a distal balloon end. The proximal and distal balloon ends are connected to the inflation catheter between the proximal catheter end and the distal catheter end. The occlusion balloon is substantially centered along the longitudinal axis in an inflated configuration. The first inflation lumen is in fluid communication with the internal balloon space. The distal pressure sensor is attached to the inflation catheter member between the proximal balloon end and the atraumatic tip. The inflatable spine has an internal spine space, an external spine surface, a proximal spine end and a distal spine end. The proximal and distal spine ends are connected to the inflation catheter. A portion of the external balloon surface contacts the external spine surface when the occlusion balloon and the inflatable spine are in an inflated configuration. The proximal spine end is connected to the inflation catheter near the proximal balloon end and the distal spine end is connected to the inflation catheter near the distal balloon end. The occlusion balloon and the inflatable spine are configured to define blood flow channels with the internal surface and the external balloon surface when the occlusion catheter system is at least partially positioned in the vessel and the occlusion balloon and the inflatable spine are in a partially inflated configuration.

In another aspect, the preferred invention is directed to an occlusion catheter system for occlusion or partial occlusion of a relatively large vessel having an internal surface. The occlusion catheter system includes an inflation catheter member having a stiffener member, an occlusion balloon, a distal pressure sensor and an inflatable spine. The inflation catheter member also includes a first inflation lumen, a second inflation lumen, a proximal catheter end and a distal catheter end. The inflation catheter member defines a longitudinal axis and has an atraumatic tip on the distal catheter end. The occlusion balloon has an internal balloon space, an external balloon surface, a proximal balloon end and a distal balloon end. The proximal and distal balloon ends are connected to the inflation catheter between the proximal catheter end and the distal catheter end. The occlusion balloon is substantially centered along the longitudinal axis in an inflated configuration. The first inflation lumen is in fluid communication with the internal balloon space. The distal pressure sensor is attached to the inflation catheter member between the proximal balloon end and the atraumatic tip. The inflatable spine has an internal spine space, an external spine surface, a proximal spine end and a distal spine end. The proximal and distal spine ends are connected to the inflation catheter. The internal spine space us in fluid communication with the second inflation lumen. A portion of the external balloon surface contacts the external spine surface when the occlusion balloon and the inflatable spine are in an inflated configuration. The proximal spine end is connected to the inflation catheter near the proximal balloon end and the distal spine end is connected to the inflation catheter near the distal balloon end.

In a further aspect, the preferred invention is directed to a rapid catheter securement device for securing a substantially cylindrical catheter to a patient. The securement device includes a base member having a skin facing surface and an engagement mechanism. The engagement mechanism is configured to movably engage the catheter. A needle housing has an arcuate housing slot, a base boss and a substantially flat lower side. The base boss is positioned proximate the lower side. An arcuate needle has a tip and a needle base end. The needle is movably mounted to the needle housing and is movable along the arcuate housing slot. The needle tip is positioned within the needle housing along the housing slot in an initial position and at least a portion of the needle is positioned outside the needle housing in a secured position proximate the lower side.

BRIEF DESCRIPTION OF THE SEVERAL VIEWS OF THE DRAWINGS

The foregoing summary, as well as the following detailed description of preferred embodiments of the in low-profile occlusion balloon catheter system and related instruments, implants and methods of the present application, will be better understood when read in conjunction with the appended drawings. For the purposes of illustrating the occlusion catheter and related components, there are shown in the drawings preferred embodiments. It should be understood, however, that the application is not limited to the precise arrangements and instrumentalities shown. In the drawings:

FIG. 1PA is a side perspective, partially cut-away view of a prior art occlusion balloon catheter implanted in a vessel with partial inflation allowing flow around an entire periphery of the occlusion balloon and a cross-sectional view taken along line X-X of the vessel and catheter;

FIG. 1E is a side perspective, partially cut-away view of the occlusion catheter system of FIG. 1 implanted in a vessel and a cross-sectional view of the occlusion balloon, spine and vessel in a partially inflated configuration, taken along line X-X;

FIG. 1F is a side perspective, partially cut-away view of the occlusion catheter system of FIG. 1 implanted in a vessel and a cross-sectional view of the occlusion balloon, spine and vessel in a fully occluded configuration, taken along line Y-Y;

FIG. 1G is a block diagram of a controller and pump that may be utilized with the occlusion catheter system of FIG. 1;

FIG. 2 is a cross-sectional view of a catheter member of the occlusion catheter system of FIG. 1, taken along line 2-2 of FIG. 1;

FIG. 3 is a cross-sectional view of an alternative preferred embodiment of the occlusion catheter system of FIG. 1, taken along line 3-3 of FIG. 1;

FIG. 13 is a top perspective view of an occlusion catheter system in accordance with a sixth preferred embodiment, showing multiple occlusion balloons positioned in series on an inflation catheter member, wherein the multiple occlusion balloons are in an inflated or partially inflated configuration;

FIG. 14 is a cross-sectional view of the occlusion catheter system of FIG. 13, taken along line 14-14 of FIG. 13;

FIG. 15 is a bottom perspective view of an occlusion catheter system in accordance with a seventh preferred embodiment, showing multiple occlusion balloons positioned in series and formed by restraining rings on an inflation catheter member, wherein the multiple occlusion balloons are in an inflated or partially inflated configuration;

FIG. 16 is a side elevational view graphically representing formation of the multiple occlusion balloons of the occlusion catheter system of FIG. 15;

FIG. 25A is a side elevational view of an occlusion catheter system in accordance with a thirteenth preferred embodiment, showing an occlusion balloon and balloon spine in an inflated or partially inflated configuration that may be utilized with any of the preferred catheters described herein;

FIG. 25B is a magnified side elevational view of a portion of the occlusion catheter system of FIG. 25A near a proximal end of an occlusion balloon and being partially transparent for clarity;

FIG. 25C is a cross-sectional view of the occlusion catheter system of FIG. 25A taken along line 25C-25C of FIG. 25B;

DETAILED DESCRIPTION OF THE INVENTION

Figure 1:
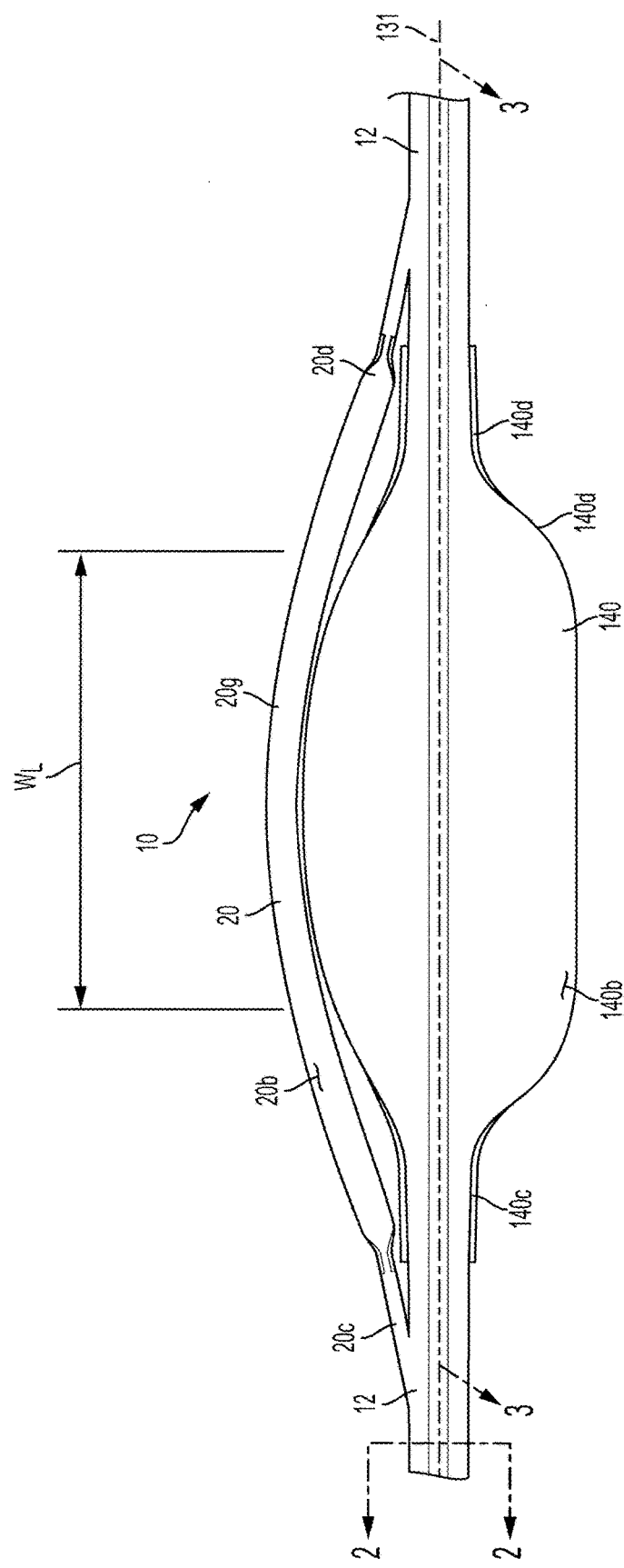
FIG. 1 is a side elevational view of a portion of an occlusion catheter system in accordance with a first preferred embodiment of the present invention, showing an occlusion balloon and inflatable spine of the occlusion catheter system in an inflated or partially inflated configuration.

Certain terminology is used in the following description for convenience only and is not limiting. Unless specifically set forth herein, the terms "a", "an" and "the" are not limited to one element but instead should be read as meaning "at least one". The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred occlusion catheter system and related parts thereof. The words, "anterior", "posterior", "superior," "inferior", "lateral" and related words and/or phrases designate preferred positions, directions and/or orientations in the human body or the device to which reference is made and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Figure 1A:
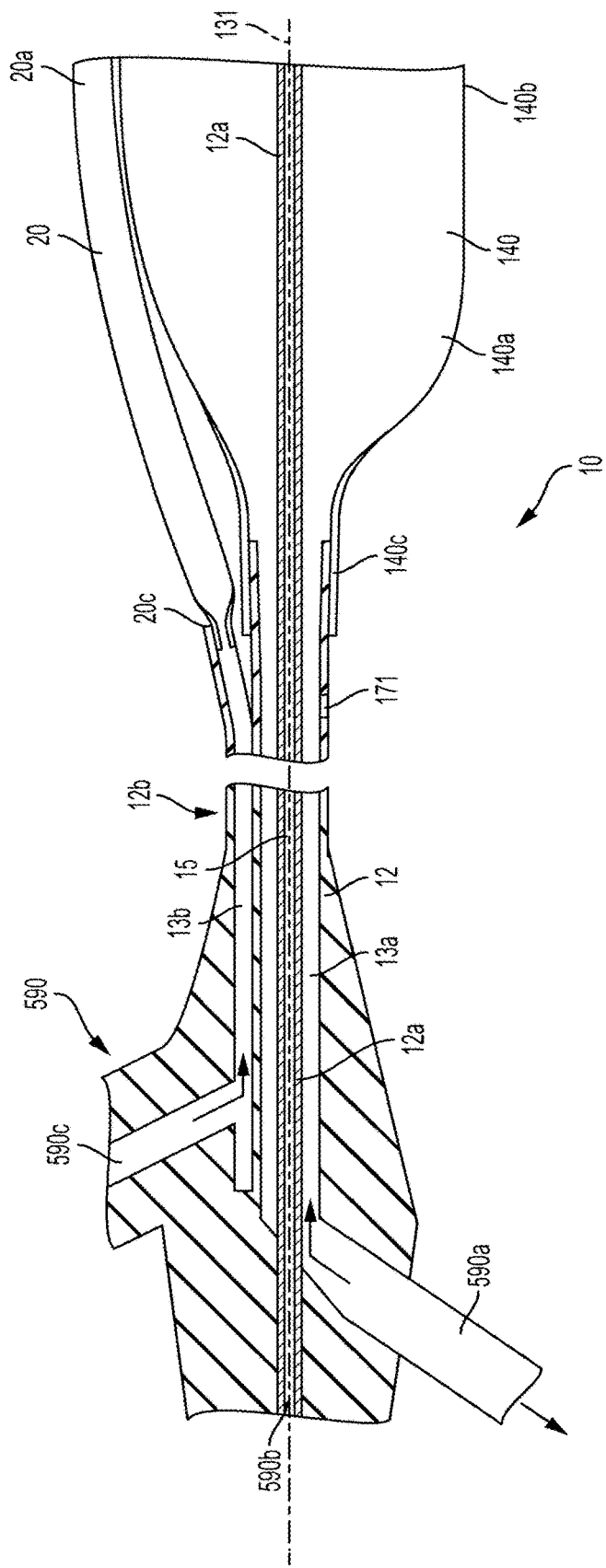
FIG. 1A is a cross-sectional view of a proximal portion of an alternative preferred embodiment of the occlusion catheter system of FIG. 1, taken near a proximal end of an occlusion balloon.

Referring to FIGS. 1-6, in a first preferred embodiment, an occlusion catheter system 10 has similarities in function to the system and method for low-profile occlusion balloon catheter described in International Patent Application No. PCT/US16/23223, titled, "System and Method for Low-Profile Occlusion Balloon Catheter," filed Mar. 18, 2016, the entire contents of which are incorporated herein by reference in their entirety. The first preferred occlusion catheter system 10 is configured to occlude or partially occlude a relatively large vessel, such as the aorta, but is not so limited and may occlude or partially occlude other vessels VW. The occlusion catheter system of the first preferred embodiment includes an inflation catheter member 12 having a stiffener member or hypotube 12a, a first inflation lumen 13a and a second inflation lumen 13b. The inflation catheter member or catheter 12 has a proximal catheter end 12b and a distal catheter end 12c and the catheter member 12 defines a longitudinal axis 131. The inflation catheter member 12 is relatively flexible along its length for traversing the non-linear path of vessels, but the longitudinal axis 131 is defined when the inflation catheter member 12 is in a relaxed or relatively straight configuration (FIG. 1C).

An occlusion balloon 140 is attached to the inflation catheter member 12 and has an internal balloon space 140a, an external balloon surface 140b, a proximal balloon end 140c and a distal balloon end 140d. The proximal and distal balloon ends 140c, 140d are connected to the inflation catheter 12, preferably by bonding or co-molding the inflation catheter 12 with the occlusion balloon 140. The first inflation lumen 13a is in fluid communication with the internal balloon space 140a, such that fluid may be delivered to and from the internal balloon space 140a through the first inflation lumen 13a to inflate and deflate the occlusion balloon 140.

In operation, the occlusion catheter system 10 is preferably inserted into a patient with the occlusion balloon 140 in a deflated or uninflated configuration (not shown) to limit the profile of the portion of the occlusion catheter system 10 that is inserted into the patient's body. The spine 20 and occlusion balloon 140 are preferably wrapped around the stiffener member 12a in the uninflated configuration. The occlusion balloon 140 is inflated to an inflated configuration (FIGS. 1 and 3) to occlude or partially occlude the vessel VW. The occlusion balloon 140 is preferably constructed of a biocompatible, relatively flexible and compliant polymeric material that is configured for engagement or co-molding with the inflation catheter member 12. The occlusion balloon 140 is not so limited and may be constructed of nearly any biocompatible material that is able to take on the general size and shape of the occlusion balloon 140, move between the deflated and inflated configurations upon receipt or withdraw of fluid or gas through the first inflation lumen 13a, perform the preferred functions of the occlusion balloon 140 and withstand the normal operating conditions of the occlusion catheter system 10. The preferred occlusion balloon 140 is also transparent or semi-transparent, such that the user can observe fluid within the occlusion balloon 140 and the stiffener member or hypotube 12a is visible through the occlusion balloon 140 (FIGS. 1, 1C and 1D). The occlusion balloon 140 is not limited to being transparent or semi-transparent and may be opaque or otherwise constructed, as long as the occlusion balloon 140 is able to performed the preferred functions, take on the general size and shape of the occlusion balloon 140 and withstand the normal operating conditions of the occlusion balloon 140.

The first preferred occlusion catheter system 10 also includes an inflatable spine 20 having an internal spine space 20a, an external spine surface 20b, a proximal spine end 20c and a distal spine end 20d. The proximal and distal spine ends 20c, 20d are connected to the inflation catheter 12 and the internal spine space 20a is in fluid communication with the second inflation lumen 13b. A user or medical professional is able to inflate the inflatable spine 20 by introducing fluid into the internal spine space 20a through the second inflation lumen 13b and deflate the inflatable spine 20 by removing fluid from the internal spine space 20a through the second inflation lumen 13b. In the first preferred embodiment, the inflatable spine 20 is constructed of a non-compliant polymeric material that is biocompatible, relatively flexible, and configured for attachment to the inflation catheter 12. The inflatable spine 20 is preferably constructed of a biocompatible polymeric material or other biocompatible non-compliant material that is able to take on the general size and shape of the inflatable spine 20 and withstand the ordinary operating conditions of the inflatable spine 20. The inflatable spine 20 is not limited to such constructions and may be constructed of nearly any biocompatible material that is able to take on the size and shape of the preferred inflatable spine 20, move between the inflated and deflated configurations upon receipt or withdraw of fluid or gas through the second inflation lumen 13b, perform the preferred functions of the inflatable spine 20 and withstand the normal operating conditions of the inflatable spine 20. The inflatable spine 20 may be constructed of the same polymeric material as the occlusion balloon 140, but is not so limited and may be constructed of a different material that is able to withstand the normal operating conditions of the spine 20 and perform the functions of the spine 20 described herein. In the preferred embodiment, the occlusion balloon 140 is constructed of a relatively compliant, biocompatible polymeric material and the spine 20 is constructed of a non-compliant, biocompatible polymeric material. The occlusion balloon 140 and the spine 20 may both be constructed of a polyurethane material. In the preferred embodiment, the polyurethane materials of the occlusion balloon 140 and the spine 20 have different durometers with the second polyurethane material of the spine 20 having a second durometer and the first polyurethane material of the occlusion balloon 140 having a first durometer. The second durometer of the spine 20 is preferably greater than the first durometer of the occlusion balloon 140.

During use, the preferred system 10 is preferably operated or pressurized with a fluid, such as a saline solution or other biocompatible fluid that is able to pressurize the occlusion balloon 140 and balloon spine 20. The fluid may be impregnated with a radiopaque additive, such as barium sulfate, to facilitate detection and location of the occlusion balloon 140 and balloon spine 20 when inserted into the patient. The radiopaque fluid in the occlusion balloon 140 and spine 20 may be visible with radiographic imaging, such as X-ray or fluoroscopy, to determine the location of the occlusion balloon 140 and spine 20 in the patient to confirm proper location or to direct positioning of the occlusion balloon 140 and the spine 20. The fluid is not limited to having radiopaque material mixed therein and may be comprised of a non-radiopaque material without significantly impacting the function of the preferred system 10. The occlusion balloon 140 and the balloon spine 20 may also be impregnated with a radiopaque material for visualization, particularly when utilized with a fluid that does not include radiopaque materials or in regulatory situations where radiopaque fluids are not preferred.

Referring to FIG. 1A-1C and 4, the inflation catheter 12 is preferably connected to an inflation hub 590 at its proximal end 12b. The inflation hub 590 of the alternative first preferred embodiment includes a first port or inflation connection port 590a, a second port or pressure sensing port 590b and a third port or spine inflation port 590c. The first port 590a is in fluid communication with the first inflation lumen 13a and the internal balloon space 140a. The second port 590b is in fluid communication with a hypotube lumen 15 of the stiffener member or the hypotube 12a and a distal side port 170 (FIG. 1C) near the distal balloon end 140d. The distal side port 170 is not limited to being positioned in the location shown in FIG. 1C and may be placed at nearly any location on or along the catheter 12, preferably distally relative to the occlusion balloon 140, including at or near the end of the inflation catheter 12 and proximate or on an atraumatic tip 450 or distal catheter end 12c. In addition, the distal side port 170 is not limited to being comprised of a port or hole that opens from the catheter 12 for sensing pressure and may be replaced by a pressure sensor, such as an electronic pressure sensor. The distal side port or distal pressure sensor 170 may further be replaced or supplemented by a different biological sensor, such as a temperature sensor, a flow sensor, a blood glucose sensor or other sensor that is able to sense a parameter for use by the medical professional. In addition, the inflation catheter 12 may include a similar port (now shown) proximally relative to the occlusion balloon 140.

The third port 590c is preferably in fluid communication with the second inflation lumen 13b and the internal spine space 20a of the spine 20. The inflation hub 590 is not limited to inclusion of the first, second and third ports 590a, 590b, 590c and may include more or less ports for fluid communication with the occlusion balloon 140, the spine 20 and others sensors or clinical sampling purposes. The spine 20 is preferably pocket-bonded to the occlusion balloon 140 and extends over the back of the occlusion balloon 140. When the spine 20 is filled from the third inflation port 590c through the second inflation lumen 13b, the inflated spine 20 preferably prevents the occlusion balloon 140 from sealing up against the vessel sidewall creating leak paths or flow channels between the external spine surface 20b, the external occlusion balloon surface 140b and an inside surface VS of a vessel wall or vessel VW (FIG. 1E) to allow for partial perfusion or blood flow around the occlusion balloon 140, as is described in greater detail below. In addition, the spine 20 and occlusion balloon 140 may be designed and configured such that continued additional pressure applied into the spine 20 and occlusion balloon 140 results in the occlusion balloon 140 over-driving or collapsing the spine 20 (FIG. 1F—sec. Y-Y) against the vessel wall VW to provide full occlusion of the vessel.

Figure 1B:
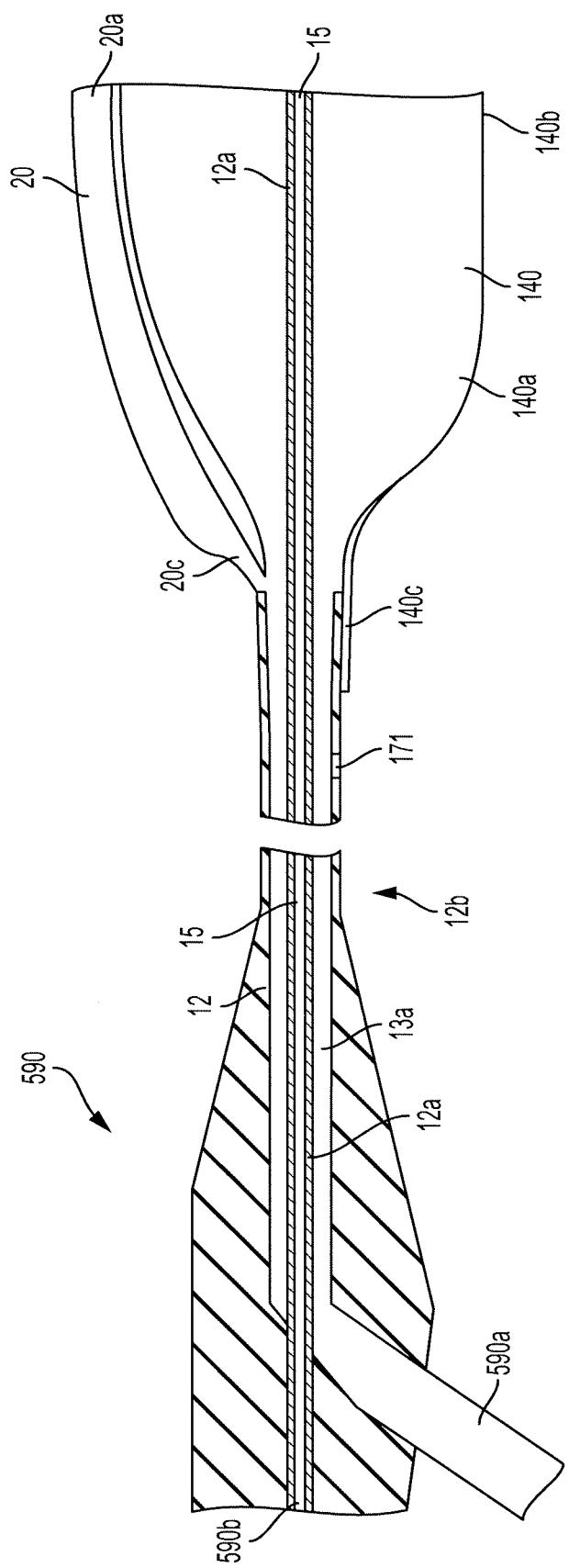
FIG. 1B is a cross-sectional view of a proximal portion of the occlusion catheter system of FIG. 1, taken near a proximal end of an occlusion balloon.
Figure 1C:
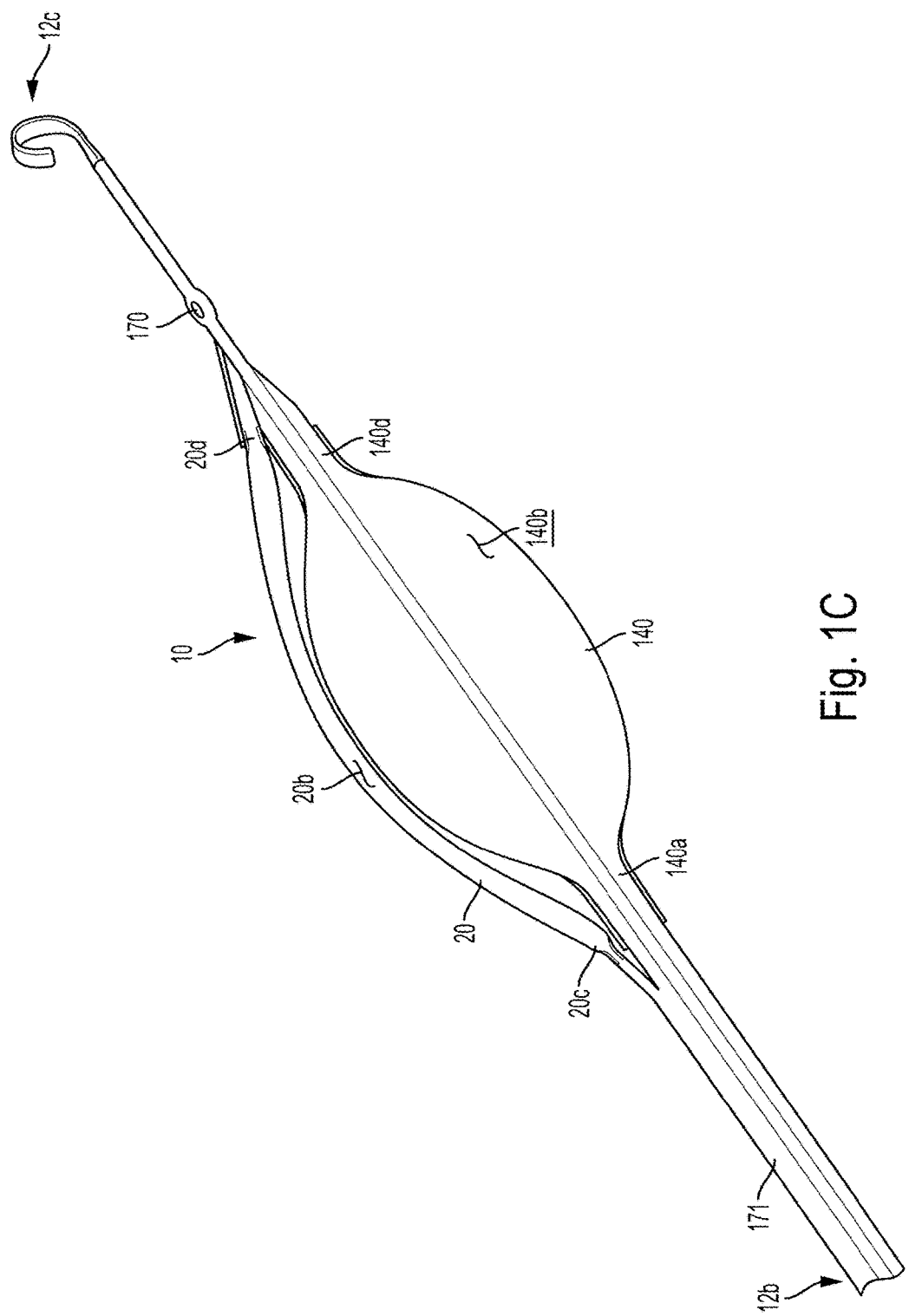
FIG. 1C is a side perspective view of a distal portion of the occlusion catheter system of FIG. 1.
Figure 1D:
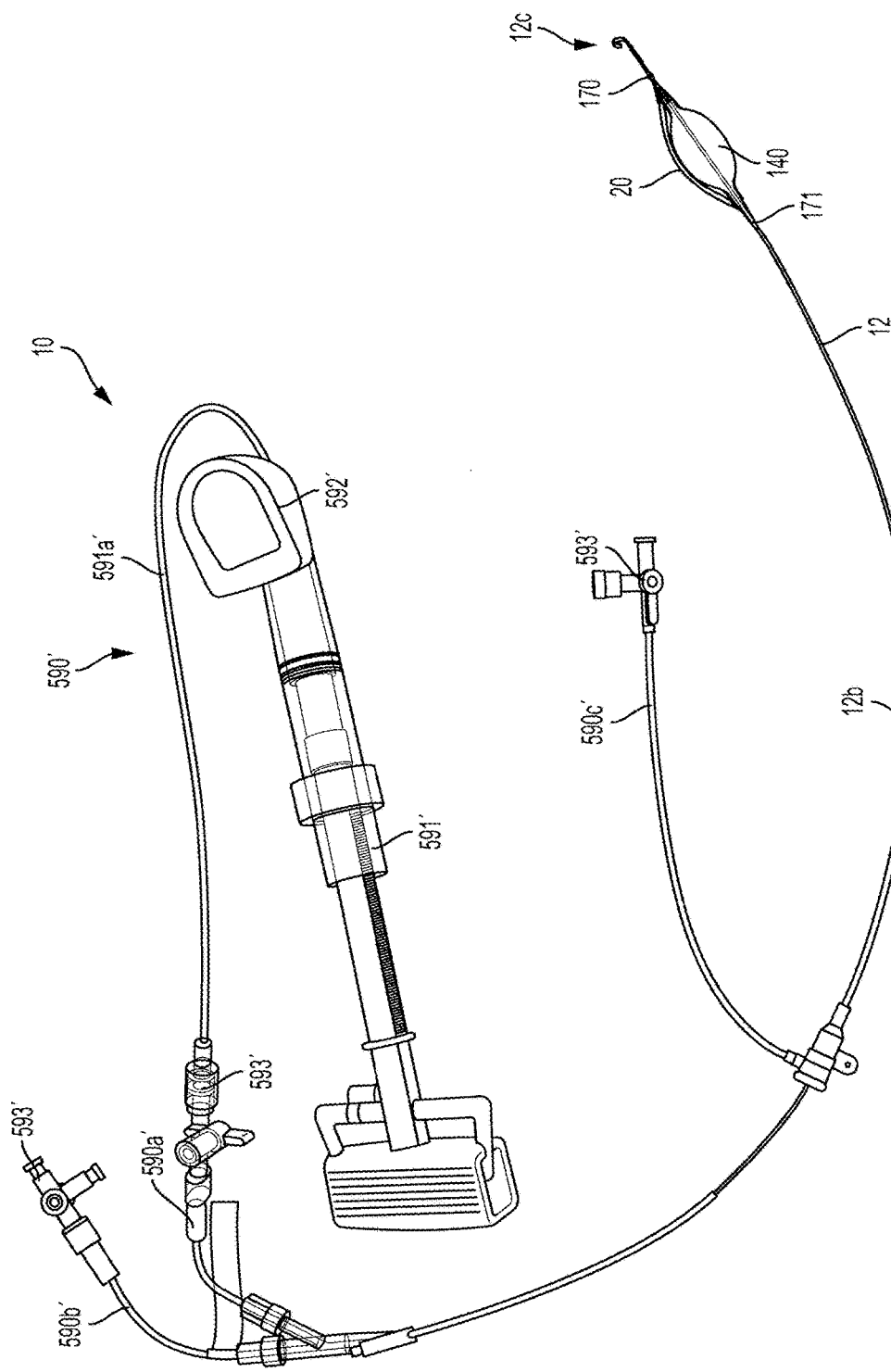
FIG. 1D is a top perspective view of the occlusion catheter system of FIG. 1 with an alternative hub for manipulation by the operator or medical technician.

Referring to FIG. 1B, in the first preferred embodiment, the inflation hub 590 includes only the first and second ports 590a, 590b. In this alternative first preferred embodiment, the first port 590a is in fluid communication with the first inflation lumen 13a, which is in fluid communication with both the internal balloon space 140a and the internal spine space 20a. The second port 590b is in fluid communication with the lumen 15 of the stiffener member 12a and the distal side port 170, preferably for sensing pressure distally relative to the occlusion balloon 140.

Referring to FIG. 1D, in the first preferred embodiment, the inflation catheter 12 may be connected to an alternative hub 590' arrangement that is utilized to inflate and deflate the occlusion balloon 140 and spine 20 and determine pressure at the distal side port 170 or otherwise sample fluid or inject medication with the distal side port 170. The alternative hub 590' includes a first port 590a' that is in fluid communication with the first inflation lumen 13a, a second port 590b' that is in fluid communication with the lumen 15 of the hypotube 12a and a third port 590c' that is in fluid communication with the second inflation lumen 13b. The first, second and third ports 590a', 590b', 590c' are comprised of flexible tubes with valves 593' attached to proximal ends that may engage a syringe, an endoflator, a pump 591' or other instrument for manipulating occlusion catheter system 10. The pump 591' preferably includes a pressure sensor display that exhibits pressure in the tubing of a lead tube 591a' extending from the pump 591'.

Referring to FIGS. 1, 1A, 2 and 3, in operation, the occlusion catheter system 10 of the alternative first preferred embodiment is insertable into a patient's vessel VW, preferably the aorta, with the occlusion balloon 140 and the inflatable spine 20 in the deflated configuration with the deflated occlusion balloon 140 and inflatable spine 20 wrapped around the stiffener member 12a. The occlusion balloon 140 and inflatable spine 20 are preferably wrapped around the stiffener member 12a such that the profile of the catheter 12 is the same or smaller where the occlusion balloon 140 and inflatable spine 20 are wrapped around the stiffener member 12a when compared to the remainder of the catheter member 12. The catheter member 12 is inserted into the vessel VW with the atraumatic tip 450 (FIGS. 4 and 5) guiding the catheter 12 into the large vessel VW. The catheter member 12 preferably includes depth markings (FIG. 44) on a proximal portion that provide a visual indication to a user regarding the depth of insertion of the occlusion balloon 140. The depth markings preferably start approximately fifteen centimeters (15 cm) proximally from the proximal balloon end 140c and extend on an external surface of the catheter 12 to a location proximate the inflation hub 590. The depth markings may also include zone markings or ranges that preferably indicate when the occlusion balloon 140 is in zone 1, zone 2 or zone 3 of the patient's aorta, as is described in further detail herein.

When the occlusion balloon 140 is placed in a desired location of the aorta, the occlusion balloon 140 may be inflated by injecting fluid or gas into the internal balloon space 140a through the first inflation lumen 13a. Fluid or gas may be injected through the first port 590a using a syringe or pump 591' that is able to connect to the first port 590a. Preferably, for full occlusion, the occlusion balloon 140 is inflated such that the external balloon surface 140b is in facing contact with internal surfaces VS of the vessel VW and blood flow is occluded from flowing past the occlusion balloon 140. The spine 20 is preferably in the deflated configuration in this occlusion technique and lies substantially flat between the external balloon surface 140b and the internal vessel surface VS, thereby not creating or creating a limited channel or path 21 for the flow of blood past the inflated occlusion balloon 140. The spine 20 is well suited to facilitate full occlusion, because the spine 20 becomes very thin or substantially flat in the deflated configuration. In the deflated configuration, the spine 20 is able to substantially conform to the external balloon surface 140b when the occlusion balloon 140 is in the inflated configuration. This feature of the spine 20 thereby limits or eliminates creation of the channel 21 adjacent the spine 20 in the deflated configuration as it conforms to the external balloon surface 140b when the occlusion balloon 140 is in the inflated configuration.

Referring to FIGS. 1, 1B, 1C, 1E and 1F, in the preferred embodiment, the user connects the pump 591' to the first port 590a, 590a' and injects pressurized fluid or gas into the catheter 12. The inflation lumen 13a in the first preferred embodiment is in fluid communication with both the occlusion balloon 140 and the spine 20, resulting in substantially simultaneous inflation of the occlusion balloon 140 and the spine 20. This simultaneous inflation results in blood flow channels 21 (See FIG. 1E) being formed at sides of the spine 20 between the external balloon surface 140b, the external spine surface 20b and the internal surfaces VS of the vessel VW in certain of the partially inflated configurations. The blood flow channels 21, shown in FIG. 1E in section Y-Y, may substantially permit sufficient flow of blood past the occlusion balloon 140 such that blood pressure proximal and distal relative to the occlusion balloon 140 may be manipulated by changing the sizes of the channels 21. Generally, when the flow channels 21 are open and blood begins to flow through the channels 21, the blood pressures at the proximal and distal balloon ends 140c, 140d begin to change. Additional fluid pressure may subsequently be applied to the occlusion balloon 140 and the spine 20 to further reduce the size of the blood flow channels 21, thereby resulting in partial occlusion of blood flow through the vessel VW and a pressure differential between the proximal balloon end 140c and the distal balloon end 140d. Referring to FIG. 1F, further fluid pressure may be applied to the occlusion balloon 140 and the spine 20 in an inflated configuration, such that the occlusion balloon 140 over-drives the spine 20 or flattens the spine 20 where the occlusion balloon 140 centrally contacts the vessel walls VW. In this inflated configuration shown in FIG. 1F, the occlusion balloon 140 is in full circumferential contact with the internal surfaces VS of the vessel VW, resulting in full occlusion of the vessel VW, and the spine 20 is collapsed or flattened such that the flow channels 21 are not formed or are collapsed.

In an alternative operation of the first preferred embodiment of the occlusion catheter system 10, the occlusion balloon 140 and spine 20 are inflated to the fully inflated configuration once placed in the predetermined location in the vessel VW. The occlusion balloon 140 and the spine 20 are inflated to the same pressure, as they are both in fluid communication with the first inflation lumen 13a. The occlusion balloon 140 and the spine 20 both inflate through various partially inflated configurations and eventually come into contact with the internal surface VS. As the fluid pressure in the occlusion balloon 140 and the spine 20 press against the internal surface VS, the size and compliant properties of the occlusion balloon 140 drives the fluid out of the spine 20 or over-drives and flattens the spine 20 against the internal surface VS of the vessel VW, thereby creating full occlusion of the vessel VW. The physician or medical technician may maintain this fully occluded configuration for a certain amount of time while the patient is diagnosed and a hemorrhage in lower portions of the patient's body is reviewed. The full occlusion preferably directs blood flow to major organs above or upstream of the full occlusion, such as the brain, heart and lungs and diverts the blood away from the lower body hemorrhage. After a limited amount of time of full occlusion, such as approximately twenty minutes (20 min), the physician or medical technician may desire to allow some blood flow past the occlusion balloon 140 to address an ischemia or inadequate blood supply that may result for organs and tissue that are deprived of blood flow due to the full occlusion.

If and when partial occlusion is desired, fluid from within the occlusion balloon 140 is withdrawn and fluid flows back into the spine 20, thereby forming the flow channels 21. The flow channels 21 are initially relatively small such that blood flow is minimal and the pressure ratio is relatively high or the degree of occlusion is relatively high. The user may continue to deflate the occlusion balloon 140 and the spine 20 to allow enlarging of the channels 21, more blood to flow through the channels 21 and reduction of the pressure ratio or reduction of the degree of occlusion. Accordingly, the more volume in the occlusion balloon 140, the less flow past the occlusion balloon 140 through the channels 21 and the less volume in the occlusion balloon 140, the more flow past the occlusion balloon 140.

Referring to FIGS. 1, 1A, 1E and 1F, in the alternative first preferred embodiment, the occlusion balloon 140 and spine are inserted into the vessel VW to the predetermined location within the vessel VW. The occlusion balloon 140 is initially inflated by introducing fluid into the first inflation lumen 13*a* through the first inflation port 590*a*. If full occlusion is desired, the occlusion balloon 140 is maintained in the fully inflated configuration with the external balloon surface 140*b* in facing engagement with the internal surface VS. If partial occlusion is desired, the spine 20 is inflated by introducing fluid into the second inflation lumen 13 through the third inflation port 590*c* and fluid may be withdrawn from the occlusion balloon 140 such that the flow channels 21 are formed. Additional fluid may be introduced into the spine 20 and additional fluid may be withdrawn from the occlusion balloon 140 to increase the size of the channels 21 and flow of blood past the occlusion balloon 140.

Referring to FIGS. 1E and 1F, in a non-limiting example, the occlusion balloon 140 and spine 20 of first preferred occlusion catheter system 10 was inserted into a high-temperature silicone rubber tube having a durometer of fifty (50 A), an approximate three-quarters of an inch (¾") inside diameter and a seven-eighths inch (⅞") outer diameter. The tube was used to simulate a patient's vessel VW, preferably a zone 1 section of the aorta. In a partially inflated configuration (FIG. 1E), wherein the channels 21 were formed to allow partial perfusion and blood flow past the occlusion balloon 140 and the spine 20 through the channels 21, seven and one-half milliliters (7.5 mL) of fluid were introduced into the system 10, the fluid pressure in the occlusion balloon 140 and the spine 20 was two and four tenths pounds per square inch (2.4 psi), an occlusion diameter DO of the occlusion balloon 140 was eighteen and one-half millimeters (18.5 mm) and a spine diameter DS of the spine 20 was two and one-half millimeters (2.5 mm). In the fully inflated configuration (FIG. 1F), wherein the spine 20 is over-driven by the occlusion balloon 140, eleven and one-half milliliters (11.5 mL) of fluid were introduced into the system 10, the fluid pressure in the occlusion balloon 140 was six and eight tenths pounds per square inch (6.8 psi), the occlusion diameter DO was nineteen millimeters (19 mm) and the spine 20 was flattened or over-driven between the inner surface of the tube and the external balloon surface 140*b*. The fluid volumes, pressures and diameters described above are not limiting and are provided as a preferred example of the operation of the first preferred system 10 in a tube that represents a typical aorta of a patient, preferably in zone 1 of the aorta. The zones of the aorta are described in FIGS. 13 and 14 and the related specification sections of US Patent Application Publication No. 2014/0243873, titled, "Fluoroscopy Independent Balloon Guided Occlusion Catheter and Method," the contents of which are incorporated herein by reference.

In another preferred non-limiting example, the occlusion balloon 140 and spine 20 of first preferred occlusion catheter system 10 was inserted into a high-temperature silicone rubber tube having a durometer of fifty (50 A), an approximate five-eighths of an inch (⅝") inside diameter and a three-quarters of an inch (⅞") outer diameter. The tube was used to simulate a patient's vessel VW, preferably a zone 3 section of the aorta. In a partially inflated configuration (FIG. 1E), wherein the channels 21 were formed to allow partial perfusion and blood flow past the occlusion balloon 140 and the spine 20 through the channels 21, five milliliters (5 mL) of fluid were introduced into the system 10, the fluid pressure in the occlusion balloon 140 and the spine 20 was one and four tenths pounds per square inch (1.4 psi), the occlusion diameter DO was fifteen millimeters (15 mm) and the spine diameter DS was two and one-half millimeters (2.5 mm). In the fully inflated configuration (FIG. 1F), wherein the spine 20 is over-driven by the occlusion balloon 140, seven milliliters (7 mL) of fluid were introduced into the system 10, the fluid pressure in the occlusion balloon 140 was five and eight tenths pounds per square inch (5.8 psi), the occlusion diameter DO was sixteen millimeters (16 mm) and the spine 20 was flattened or over-driven between the inner surface of the tube and the external balloon surface 140*b*. The fluid volumes, pressures and diameters described above are not limiting and are provided as a preferred example of the operation of the first preferred system 10 in a tube that represents a typical aorta of a patient, preferably in zone 3 of the aorta. The zones of the aorta are described in FIGS. 13 and 14 and the related specification sections of US Patent Application Publication No. 2014/0243873, titled, "Fluoroscopy Independent Balloon Guided Occlusion Catheter and Method," the contents of which are incorporated herein by reference. In both of the preferred examples, portions of the external balloon surface 140*b* and the external spine surface 20*b* remain in contact with the internal surface VS of the vessel VW to secure the occlusion balloon 140 in the predetermined location in the vessel VW.

Referring to FIG. 3, the spine 20 is shown as being in fluid communication with the first inflation lumen 13*a* (at distal spine end 20*d*) and the second inflation lumen 13*b* (at proximal spine end 20*c*). This configuration of the occlusion catheter system 10 is not limited to having the spine 20 in fluid communication with both the first and second inflation lumens 13*a*, 13*b* and may be designed and configured to be in fluid communication with only the first inflation lumen 13*a* (FIG. 1B) or in fluid communication with only the second inflation lumen 13*b* (FIG. 1A), as is described above.

Referring to FIGS. 1-3, if and when the technician or medical professional desires partial occlusion or the ability to allow some blood to flow past the occlusion balloon 140, fluid or gas is introduced into the spine 20. The fluid or gas may be introduced into the first lumen 13*a* through the first port 590*a* in the alternative first preferred embodiment (FIG. 1B) or through the second lumen 13*b* through the third port 590*c* in the first preferred embodiment (FIG. 1A). The spine 20 expands from the substantially flat, deflated or uninflated configuration into the inflated configuration (FIG. 1), thereby urging the external balloon surface 140*b* of the occlusion balloon 140 away from the internal surface VS of the vessel VW proximate the inflated spine 20. The inflated spine 20 preferably creates the blood flow channels 21 at least on either side of the inflated spine 20 between the internal surfaces VS of the vessel VW, the external spine surface 20*b* and the external balloon surface 140*b* (See FIG. 1E). These blood flow channels 21 allow at least partial flow of blood through the blood flow channels 21 and past the occlusion balloon 140.

The non-compliant nature of the spine 20 preferably facilitates the creation of the blood flow channels 21 by generally maintaining its cylindrical shape at predetermined pressures. Adjusting the pressure within the spine 20 and the occlusion balloon 140 can likewise impact the size of the blood flow channels 21 and the amount of blood flowing through the blood flow channels 21. The non-compliant nature of the spine 20 also maintains the diameter of the spine 20 under increasing pressure and the compliant nature of the occlusion balloon 140 wraps around sides of the spine 20, thereby pushing fluid out of the spine 20 and flattening the spine 20 as the system reaches the fully inflated configuration. The spine 20 may also be deflated by withdrawing the fluid or gas from the internal spine space 20a such that the spine 20 reverts to the deflated configuration in the first preferred embodiment by withdrawing fluid or gas through the third port 590c. In the deflated configuration, the spine 20 lies substantially flat against the external balloon surface 140b to revert to a full occlusion of the vessel VW. The inflation of the spine 20 and subsequent creation of the blood flow channels 21 at sides of the spine 20 preferably does not impact engagement of the occlusion balloon 140 with the internal surfaces VS of the vessel VW. That is, even when the spine 20 is inflated, the external balloon surface 140b of the occlusion balloon 140 continues to maintain facing engagement with the internal surface VS of the vessel VW, thereby reducing or eliminating movement or vibration of the occlusion balloon 140 that may occur when blood is allowed to flow around a full circumference of the occlusion balloon 140, as is shown in Fig. A.

The stiffener member 12a is preferably comprised of a nitinol hypotube 12a, which is a small tube that has a strength and stiffness configured to permit insertion of the occlusion catheter system 10 into the patient's vessel VW along the potentially curved vessel path into the preferred portion of the vessel VW. The stiffener member 12a may be hollow and include the hypotube lumen 15 therethrough that is in fluid communication with the distal side port 170. The side port 170 is preferably positioned distally relative to the distal spine end 20d on the catheter 12. The hypotube lumen 15 is also preferably in fluid communication with the second port 590b. The stiffener member 12a is not limited to including the hypotube lumen 15 or to being constructed of nitinol. The stiffener member 12a may be substantially solid, be constructed of alternative biocompatible metallic or polymeric materials, such as stainless steel, polyether ether ketone ("PEEK") or have alternative constructions, based on requirements of the preferred occlusion catheter system 10 or preferences of the designer or medical professional.

The hypotube lumen 15 and distal side port 170 may be utilized to withdraw fluids from the vessel VW, inject fluid into the vessel VW, detect pressure of the fluid within the vessel VW or otherwise provide access to the vessel VW distally relative to the occlusion balloon 140 during use. The catheter 12 may also include a proximal side port or proximal pressure sensor 171 near the proximal balloon end 140c that may be utilized to withdraw fluids from the vessel, inject fluids into the vessel VW, detect pressure of the fluid within the vessel VW downstream from the occlusion balloon 140 or otherwise provide access to the vessel VW proximally relative to the occlusion balloon 140 during use. The proximal port 171 may be in fluid communication with a pressure sensor lumen (not shown) that extends from the hub 590 to the proximal side port 171 within the catheter 12. The distal side port 170 and proximal port 171 may alternatively be replaced by or supplemented with electronic pressure sensors, including the distal pressure sensor 170 and the proximal pressure sensor 171 that provide pressure sensing capability to the occlusion catheter system 10. The electronic pressure sensors may have wiring that extends through the catheter 12 or may be comprised of wireless sensors that wirelessly transmit pressure or other sensed features, such as temperature, flow, pH or other features, to a data acquisition system.

The first preferred occlusion catheter system 10 is constructed such that the proximal spine end 20c is connected to the inflation catheter 12 near the proximal balloon end 140c and the distal spine end 20d is connected to the inflation catheter 12 near the distal balloon end 140d. The ends 20c, 20d, 140c, 140d are preferably configured to facilitate wrapping the occlusion balloon 140 and the spine 20 around the stiffener member 12a in the deflated configuration or drawing a vacuum on the occlusion balloon 140 and the spine 20 for insertion into the vessel VW. The ends 20c, 20d, 140c, 140d are not so limited and may be connected and secured to the catheter 12 at nearly any location such that the occlusion catheter system 10 is able to perform its preferred functions and withstand its normal operating conditions. For example, the occlusion balloon 140 may be configured with a feature providing central fluid communication with the hollow hypotube 12a such that the occlusion balloon 140 expands both longitudinally and radially from the deflated configuration to the inflated configuration and the proximal and distal ends 140c, 140d are not directly connected to the catheter 12, but are only connected through the central engagement with the hollow hypotube 12a.

The first preferred embodiment of the occlusion catheter system 10 may alternatively be configured with only the first inflation lumen 13a being in fluid communication with both the occlusion balloon 140 and the spine 20 and elimination of the second inflation lumen 13b. This configuration, as is shown in FIG. 1B, may facilitate a smaller profile for the catheter member 12, because the catheter member 12 only accommodates the first inflation lumen 13a, as opposed to both the first and second inflation lumens 13a, 13b. In this alternative first preferred embodiment, the occlusion balloon 140 and the spine 20 are both inflated by injecting fluid or gas into the internal balloon space 140a and the internal spine space 20a. The fluid or gas is preferably introduced into the first lumen 13a through the first port 590a of the hub 590. In this alternative first preferred embodiment, the occlusion balloon 140 is preferably constructed of a compliant, biocompatible material and the spine 20 is preferably constructed of a non-compliant, biocompatible material. Accordingly, the spine 20 generally maintains its pre-determined shape during inflation and the blood flow channels 21 are defined on either side of the spine 20 during inflation and in the inflated configuration. The alternative first preferred embodiment of the occlusion catheter system 10 may provide full occlusion by inflating the spine 20 and occlusion balloon 140 until the compliant occlusion balloon 140 blocks the blood flow channels 21 by generally conforming to the shape of the spine 20 and the inside surfaces VS of the vessel VW.

Figure 4:
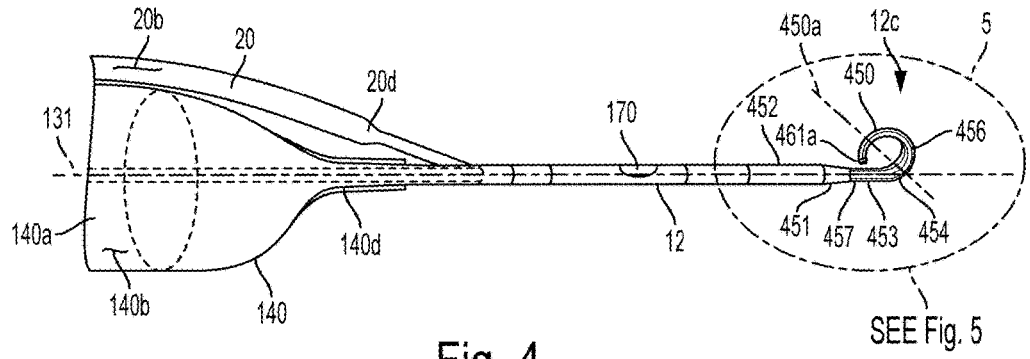
FIG. 4 is a top perspective view of a distal portion of the occlusion catheter system of FIG. 1.
Figure 5:
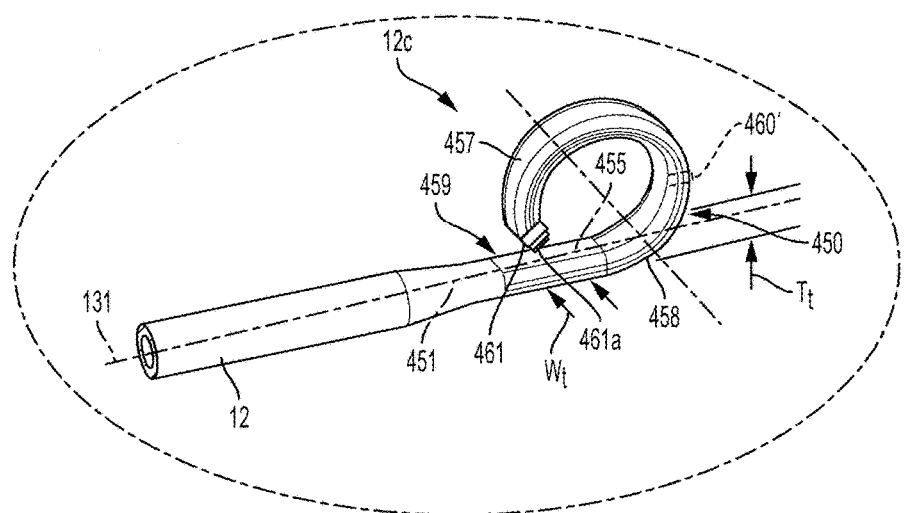
FIG. 5 is a magnified top perspective view an atraumatic tip of the occlusion catheter system of FIG. 1, taken from within shape 5 of FIG. 4.
Figure 6:
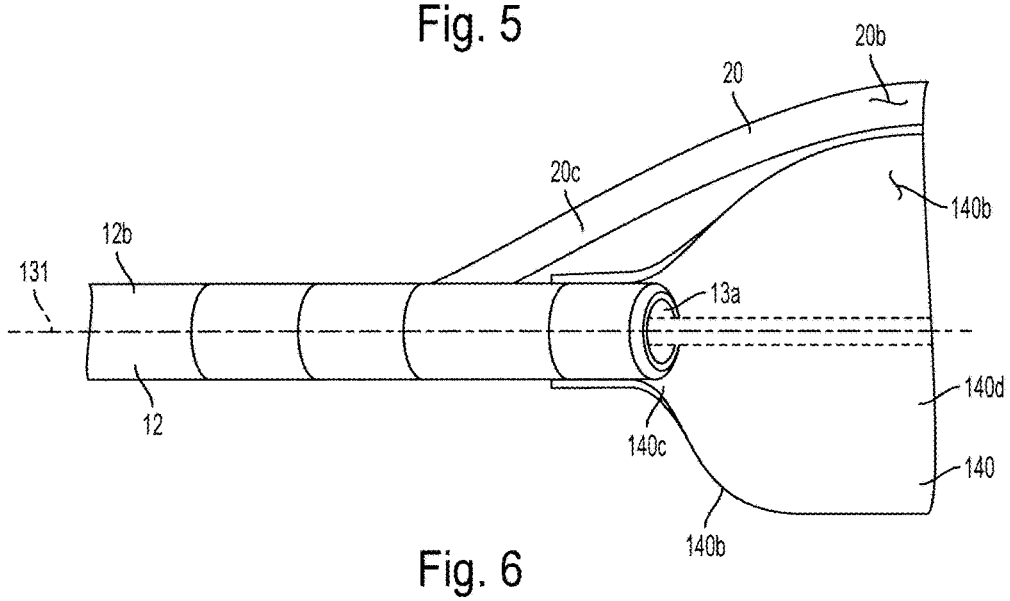
FIG. 6 is a side perspective view of a portion of the occlusion catheter system of FIG. 1, taken near a proximal balloon end and a proximal spine end of the occlusion balloon and the inflatable spine of the occlusion catheter system of FIG. 1.

Referring to FIGS. 4 and 5, in the first preferred embodiment, a guiding atraumatic tip 450 is preferably secured to or co-molded with the distal end 12c of the catheter 12. The guiding atraumatic tip 450 may be employed with any of the preferred embodiments of the occlusion catheter system 10 described herein. The guiding atraumatic tip 450 is preferably comprised of a polymeric cylindrical or tubular member 452 that has a distal section 454 that has been formed into a generally flattened cylinder having two generally planar opposing surfaces 455, 457 and two generally curved opposing surfaces 458, 459. The two generally planar opposing surfaces 455, 457 include an inner planar surface 455 and an outer planar surface 457. The distal section 454 has a distally extending section 453 that projects distally and a curved section 456 continuous with the distally extending section that curves away from the central longitudinal axis 131 of the occlusion catheter system 10, then proximally toward the occlusion balloon 140 and subtends a generally circular arc toward the central longitudinal axis 131 of the occlusion catheter system 10. The angle of the curve may be between about one hundred eighty degrees (180°) and three hundred fifty-five degrees (355°), more preferably between about two hundred seventy degrees (270°) and three hundred fifty degrees (350°) and even more preferably between about three hundred degrees (300°) and three hundred fifty degrees (350°) such that a gap is provided between the terminal end of the generally cylindrical flattened distal section 454 and the more proximal surface of the distal section 454. The distally extending section 453 and curved section 456 may alternatively be formed as a generally in-plane circular shape or may be formed as an out-of-plane generally helical shape, where a terminal end of the curved section 456 is laterally displaced from the central longitudinal axis 131 of the occlusion catheter system 10. In this manner, the generally flattened distal section 454 is characterized by a generally circular profile.

In the preferred embodiments, a tip thickness Tt is defined between the inner planar surface 455 and the outer planar surface 457 and a tip width Wt is defined between the opposing curved lateral surfaces 458, 459. The tip width Wt is preferably greater than the tip thickness Tt such that the atraumatic tip 450 is readily flexible about a central tip axis 450a. The atraumatic tip 450 is preferably flexible about the central tip axis 450a from the substantially circular profile in the relaxed configuration to the introduction configuration, wherein the atraumatic tip 450 is relatively straight or positioned on the longitudinal central axis 131. In the preferred embodiments, the tip thickness Tt is less than the tip width Wt. The relatively smaller tip thickness Tt in comparison to the tip width Wt facilitates the flexing of the atraumatic tip 450 from the relaxed configuration with the substantially circular profile to the introduction configuration, wherein the atraumatic tip 450 is substantially straight and is positioned on the longitudinal central axis 131 and renders bending of the atraumatic tip 450 laterally more difficult.

A tapered transition section 451 may, optionally, be provided between the polymeric cylindrical or tubular member 452 and the generally flattened cylindrical distal section 454. The guiding atraumatic tip 450 may be integral with the catheter member 12 of occlusion catheter system 10. Alternatively, the guiding atraumatic tip 450 may be fabricated as a discrete member and joined to the catheter member 12 of the occlusion catheter system 10.

The guiding atraumatic tip 450 is preferably constructed of a polyether block amide (PBAX, Arkema, Paris France) having a durometer of forty (40D) or a similar polymer, such as a polyurethane or polyethylene that is compatible with the catheter 12, the spine 20 and the occlusion balloon 140 to make bonding easier and more secure, but is not so limited. As discussed above, the guiding atraumatic tip 450 may be either cylindrical or tubular, or have a solid cylindrical section and a tubular section. The curve of the guiding atraumatic tip 450 may be made by any of a wide number of processes, including, for example, injection molding, round extrusion, flattening and post-processing into the curved distal section 456, a flat extrusion bonded to a round extrusion, or an extrusion that is pressed into a hot die having a shape of the desired curved distal section 450.

The atraumatic tip 450 may include a radio opaque tip marker 460. The radio opaque tip marker 460 may be implemented as a band surrounding the tip 450 or as a two-dimensional planar material on one or both of the planar opposing surfaces 455. Alternatively, the radio opaque tip marker 460 may be located at the most distal point of the atraumatic tip 450 indicated at 460' in FIG. 5. The band or the planar material may be composed of any suitable radio opaque material, such as for example, stainless steel or a suitable alloy such as platinum iridium. In another example preferred embodiment, the tip 450 may be made of a plastic or polymer, such as for example, a polyether block amide, such as PEBAX, that is impregnated with a radio opaque material. In another preferred example embodiment, the plastic or polymer composition forming the tip 450 may be mixed with a radio opaque compound such as, for example, barium sulfate sufficient to permit visualization of the tip 450 using x-ray or fluoroscopy. Any of the preferred embodiments of the occlusion catheter systems 10 described herein, including the first preferred embodiment of the occlusion catheter system 10, may include the atraumatic tip 450 mounted or co-molded onto the distal end 12c of the occlusion catheter system 10 to facilitate guiding of the catheter system 10 into the large vessel VW, preferably the aorta of the patient, and generally preventing the catheter 12 from entering a secondary vessel VW during insertion.

Referring to FIGS. 1-6, the occlusion catheter system 10 of the first preferred embodiment is utilized to occlude or partially occlude a relatively large vessel VW, such as the aorta, having an internal surface VS. The occlusion catheter system 10 includes the inflation catheter member 12 having the stiffener member 12a, the first inflation lumen 13a, the proximal catheter end 12b and the distal catheter end 12c. The inflation catheter member 12 defines a longitudinal axis 131 and is relatively flexible with the longitudinal axis 131 extending along the inflation catheter member 12 and the stiffener member 12a. The inflation catheter member 12 has the atraumatic tip 450 at the on the distal catheter end 12c that permits insertion of the inflation catheter member 12 into the relatively large vessel VW and inhibits movement of the atraumatic tip 450 into smaller vessels during the insertion process, while also limiting damage to the vessel VW during insertion.

The stiffener member 12a of the first preferred embodiment is comprised of the hypotube 12a that is constructed of the nitinol material or a relatively strong metallic material. The preferred hypotube 12a includes the lumen 15 therein. In addition, the atraumatic tip 450 of the first preferred embodiment is comprised of a generally flattened cylinder in a relaxed configuration having two planar opposing surfaces 455, 457.

The occlusion catheter system 10 of the first preferred embodiment also includes the occlusion balloon 140 with the internal balloon space 140a, the external balloon surface 140b, the proximal balloon end 140c and the distal balloon end 140d. The proximal and distal balloon ends 140c, 140d are connected to the inflation catheter member 12 between the proximal catheter end 12b and the distal catheter end 12c. The occlusion balloon 140 has a working length $W_L$ between the proximal and distal ends 140c, 140d where at least portions of the external balloon surface 140b preferably contact the internal surface VS of the vessel VW in an occlusion or partial occlusion configuration. The occlusion balloon 140 is substantially centered along the longitudinal axis 131 in an inflated configuration. The first inflation lumen 13a is in fluid communication with the internal balloon space 140a such that fluid or gas can be introduced into the inflation balloon 140 through the first inflation lumen 13a to inflate the occlusion balloon from the uninflated configuration, through various partially inflated configurations and to the inflated or fully inflated configuration.

The occlusion catheter system 10 includes the distal pressure sensor 170 attached to the inflation catheter member 12 between the distal balloon end 140d and the atraumatic tip 450. The pressure sensor 170 is comprised of an electronic pressure sensor in the first preferred embodiment, which will be described in further detail below with respect to other preferred embodiments. The pressure sensor 170 may alternatively be comprised of the distal side port 170 in the inflation catheter member 12. The distal side port 170 is preferably in fluid communication with the lumen 15 in the stiffener member 12a so that pressure may be determined via the fluid in the vessel VW, through the distal side port 170 and through the lumen 15.

The occlusion catheter system 10 also includes the inflatable spine 20 having the internal spine space 20a, the external spine surface 20b, the proximal spine end 20c and the distal spine end 20d. The inflatable spine 20 has a substantially constant spine diameter Ds between the proximal spine end 20c and the distal spine end 20d in the partially and fully inflated configurations. The inflatable spine 20, similar to the occlusion balloon 140, may be expanded to partially and fully inflated configurations from the uninflated configuration, wherein the spine 20 is substantially flattened. The inflatable spine 20 has a plurality of partially inflated configurations between the uninflated configuration and the fully inflated configuration. In certain of the partially inflated configurations, the inflatable spine 20 has the substantially constant spine diameter $D_S$. The inflatable spine 20 is not limited to having the substantially constant spine diameter $D_S$ in certain of the partially inflated configurations and may have a variable cross-section, a cross-section that is substantially consistent, but not circular, or may have other configurations that are designed for creating blood flow channels 21, as is described herein.

The occlusion balloon 140 of the first preferred embodiment has the occlusion diameter $D_O$ that is at least twice the spine diameter DS when the occlusion balloon 140 and the inflatable spine 20 are inflated to one of the partially inflated configurations. For example, a preferred occlusion balloon 140 and inflatable spine 20 configuration of the first preferred embodiment in the partially inflated configuration (FIG. 1E), as was described above, may have the occlusion diameter $D_O$ of approximately eighteen and on-half millimeters (18.5 mm) while the spine diameter $D_S$ is approximately two and one-half millimeters (2.5 mm) in a zone 1 portion of an artery, while the occlusion diameter $D_O$ is approximately fifteen millimeters (15 mm) and the spine diameter $D_S$ is approximately two and one-half millimeters (2.5 mm). In this first preferred embodiment configuration, the occlusion diameter $D_O$ is approximately six to seven and one-half (6-7.5) times larger than the spine diameter $D_S$ in the partially inflated configuration. The ratio is not so limited and may be approximately two to seven and one-half or more (2-7.5+) in certain preferred configurations and when introduced into particularly large vessels VW. In the first preferred embodiment, the occlusion balloon 140 may be molded to an approximate ten to fifteen millimeter (10-15 mm) occlusion diameter $D_O$ and the balloon spine 20 may be molded to an approximate two and one-half millimeter (2.5 mm) spine diameter $D_S$, thereby resulting in the occlusion diameter $D_O$ being approximately four to six (4-6) times greater than the spine diameter $D_S$. The first preferred occlusion balloon 140 and the inflatable spine 20 are not limited to having these specifically described occlusion and spine diameters $D_O$, $D_S$ and may have other specific diameters and shapes, as long as the occlusion catheter system 10 creates the blood flow channels 21 or full occlusion of the vessel VW when desired by the medical technician and are able to withstand the normal operating conditions of the preferred system 10. In addition, this ratio of the occlusion diameter $D_O$ relative to the spine diameter $D_S$ is impacted by the size of the vessel VW that the system 10 is operating within and the compliant or non-compliant nature of the occlusion balloon 140 and the spine 20, respectively.

In the first preferred embodiment, the first inflation lumen 13a is in fluid communication with the internal spine space 20a of the inflatable spine 20 such that the occlusion balloon 140 and the inflatable spine 20 are inflated when pressurized fluid or gas is introduced into the first inflation lumen 13. In this first preferred embodiment, the internal spine space 20a and the internal balloon space 140a are both subjected to the same pressurized fluid when pressurized fluid is introduced into the first inflation lumen 13a.

In the alternative first preferred embodiment, the second inflation lumen 13b is in fluid communication with the internal spine space 20a of the inflatable spine 20 and the first inflation lumen 13a is in fluid communication with the internal balloon space 140a of the occlusion balloon 140. In this alternative first preferred embodiment, the medical technician may individually introduce pressurized fluid or gas into the inflatable spine 20 and the occlusion balloon 140 based on preferences or clinical needs. The technician may, therefore, only introduce pressurized fluid into the occlusion balloon 140 to provide fully occlusion of the vessel VW, may provide full pressure to the balloon spine 20 and partial or a lower pressure to the occlusion balloon 140 to facilitate creation of the blood flow channels 21 or nearly any combination of pressures to the occlusion balloon 140 and the inflatable spine 20, respectively. In addition, the individual pressures may be controlled by the controller 8 based on pressure sensed by sensors associated by the occlusion catheter system 10 to provide partial, fully or no occlusion of the vessel VW, based on the condition of the patient or preferences of the medical technician.

The proximal and distal spine ends 20c, 20d of the first preferred embodiments are connected to the inflation catheter 12 and a portion of the external balloon surface 140b contacts the external spine surface 20b when the occlusion balloon 140 and the inflatable spine 20 are in an inflated configuration, partially inflated configuration or fully inflated configuration. Portions of the external spine surface 20b and the external balloon surface 140b are nearly always in contact with each other, even in the uninflated configuration, when the occlusion catheter system 12 is assembled, as the inflatable spine 20 is generally wrapped or folded around the occlusion balloon 140 in the uninflated configuration for insertion into or withdraw from the vessel VW. The proximal spine end 20c is connected to the inflation catheter 12 near the proximal balloon end 140c and the distal spine end 20d is connected to the inflation catheter 12 near the distal balloon end 140d. The occlusion balloon 140 and the inflatable spine 20 are configured to define the blood flow channels 21 with the internal surface VS of the vessel VW and the external balloon surface 140b when the occlusion catheter system 10 is at least partially positioned in the vessel VW and the occlusion balloon 140 and the inflatable spine 20 are in the partially inflated configuration.

Referring to FIGS. 1A-5, to utilize the first preferred occlusion catheter system 10, the catheter 12 is inserted into the patient, preferably in the left or right femoral common artery or the left or right common iliac artery through a small puncture. The catheter 12 is introduced into the artery or vessel, preferably through an introducer sheath (not shown). When introduced, the atraumatic tip 450 is straightened, substantially along the longitudinal axis 131 and may return to its substantially circular profile when the atraumatic tip 450 enters the vessel VW. The preferred atraumatic tip 450 guides the tip of the catheter 12 through the major vessel VW, generally preventing the catheter 12 from entering smaller vessels that branch off of the major vessel VW. The atraumatic tip 450 preferably guides the catheter 12 and the occlusion balloon 140 into an appropriate or desired location in the major vessel VW where occlusion or partial occlusion is desired by the physician or medical technician. The atraumatic top 450 may, for example, guide the occlusion balloon 140, in an uninflated configuration, into various zones in the aorta below the aortic arch, such as in the thoracic aorta, the abdominal aorta or at nearly any location therein desired by the user.

When the occlusion balloon 140 is positioned appropriately in the vessel VW, a proximal end of the catheter 12 is attached to an insufflator or other device that is able to introduce pressurized fluid into the occlusion balloon 140 and the spine 20. In the first preferred embodiment wherein the first port 590a is in fluid communication with the first inflation lumen 13a, which is in fluid communication with both the internal balloon space 140a and the internal spine space 20a, the insufflator introduces substantially equal pressure into both the occlusion balloon 140 and the spine 20. The second port 590b is in fluid communication with the internal lumen 15 of the stiffener member or hypotube 12a and the distal side port 170, preferably for sensing pressure distally relative to the occlusion balloon 140, but also potentially for introducing medication, withdrawing blood or other fluids from the vessel VW or otherwise gaining fluid access to the vessel VW proximate the distal side port 170. Pressurized fluid is introduced into the occlusion balloon 140 and the spine 20 to at least partially occlude the vessel VW, typically to limit blood flow to the patient's lower extremities and preserve blood flow to major organs, such as the heart, lungs and brain. When inflated, at least portions of the external balloon surface 140b and the external spine surface 20a and in contact with the internal surface VS of the vessel VW, thereby creating the channels 21 that permit flow of blood past the occlusion balloon 140 and the spine 20 through the channels 21. The flow channels 21 are defined between the external spine surface 20a of the spine 20, the external balloon surface 140b and the internal surface VS of the vessel VW (See FIG. 1E, wherein pressure proximal and distal of the occlusion balloon 140 is likely not impacted) to permit partial blood flow through the vessel VW. The size of the channels 21 may be adjusted by modifying the inflation pressure in the spine 20 and the occlusion balloon 140 to permit more or less flow through the vessel VW.

The pressure within the occlusion balloon 140 and spine 20 may specifically be monitored and controlled based on nearly any desired factor determined by the medical professional, such as the blood pressure in the vessel VW upstream from the occlusion balloon 140, which may be detected by a pressure sensor or fluid pressure head through the distal side port 170. For example, the medical professional may desire to maintain a predetermined pressure on the upstream side of the occlusion balloon 140 in its mounted configuration and may control the pressure in the occlusion balloon 140 and spine 20 to maintain this blood pressure. The catheter 12 may alternatively be attached to a controller 8 and a pump 7 for controlling pressure within the occlusion balloon 140 and the spine 20. The pump 7 preferably replaces the insufflator to mechanically pump pressurized fluid into the occlusion balloon 140 and the spine 20. The controller 8 may receive pressure readings from within the occlusion balloon 140 and spine 20, but is not so limited. The controller 8 preferably receives pressure readings distally relative to the occlusion balloon 140, potentially from the distal side port 170, and/or proximally relative to the occlusion balloon 140, potentially from the proximal port 171. The controller 8 may be configured to maintain a predetermined blood pressure detected at the distal side port 170, a predetermined blood pressure differential measured between the distal side port 170 and the proximal side port 171, a predetermined pressure within the occlusion balloon 140 and the spine 20, a predetermined blood pressure detected at the proximal pressure sensor 171, other predetermined pressures or may react based on other biomedical data gathered from the patient that may be transmitted to the controller 8. The preferred controller 8 receives at least blood pressure from the distal side port 170, the proximal pressure sensor 171 and pressure of the fluid in the occlusion balloon 140 and spine 20 and controls the pump 7 to inject fluid into the spine 20 and the occlusion balloon 140, withdraw fluid from the spine 20 and the occlusion balloon 140 or shuts-off the pump 7.

In the first preferred embodiment, the occlusion balloon 140 is preferably constructed of a compliant material and the spine 20 is preferably constructed of a non-compliant material. The occlusion balloon 140 may be constructed of a compliant polyurethane or polyolefin copolymer ("POC") material that is able to take on the general size and shape of the occlusion balloon 140, perform the preferred functions of the occlusion balloon 140 and withstand the normal operating conditions of the occlusion balloon 140. The introduction of pressurized fluid into the spine 20 and occlusion balloon 140 preferably results in the spine 20 and occlusion balloon 140 inflating into the vessel to contact the inside surfaces VS of the vessel VW. The size and compliant nature of the preferred occlusion balloon 140 results in over-driving or flattening of the non-compliant spine 20 after the occlusion balloon 140 engages the internal surfaces VS of the vessel VW and the spine 20 inflates to its full diameter, such as when the occlusion balloon 140 is in the fully inflated configuration or a relatively high pressure partial inflated configuration. The preferred spine 20 has an inflated diameter of approximately one-half to seven millimeters (½-7 mm), more preferably one and one-half to three and one-half millimeters (1½-3½ mm) and is preferably approximately two and one-half millimeters (2½ mm) in an inflated configuration.

In the preferred embodiments, the occlusion balloon 140 is preferably sized to have a maximum diameter that is able to fully occlude the vessel VW into which the occlusion balloon 140 is introduced. In the preferred embodiments, the occlusion balloon 140 may have an inflated occlusion diameter $D_O$ of approximately ten to thirty-two or greater millimeters (10-≈≥32 mm). An example preferred occlusion balloon 140 may be constructed of a compliant balloon material that is blown to an occlusion diameter $D_O$ of twelve to fifteen millimeters (12-15 mm) and is capable of expanding to approximately thirty-two millimeters (32 mm) or more in an inflated configuration. In the example first preferred embodiment, the occlusion balloon 140 and spine 20 may provide partial occlusion when pressurized at one-half atmosphere (½ atm) and full occlusion wherein the occlusion balloon 140 over-drives or flattens the spine 20 at one atmosphere (1 atm)(FIG. 1F), but is not so limited. The preferred occlusion catheter system 10 may be otherwise configured such that nearly any range of pressures may be applied to the occlusion balloon 140 and spine 20 to facilitate partial and full occlusion of the vessel VW.

The occlusion catheter system 10 may also be supplied in a kit with multiple occlusion catheter systems 10 and introduction instruments provided in the kit. The kit may include multiple catheters 12 having differently sized occlusion balloons 140 for occluding or partially occluding differently sized vessels VW. In addition, the occlusion balloon 140 may be inflated to various diameters depending on the pressure introduced into the internal balloon space 140a. As a non-limiting example the occlusion balloon may have an occlusion diameter $D_O$ of approximately fifteen millimeters (15 mm) when five cubic centimeters (5 cc) of fluid are introduced into the internal balloon space 140a, an occlusion diameter $D_O$ of twenty millimeters (20 mm) when eight cubic centimeters (8 cc) are introduced, twenty-five millimeters when thirteen cubic centimeters (13 cc) are introduced, thirty millimeters (30 mm) when twenty cubic centimeters (20 cc) are introduced and thirty-two millimeters (32 mm) when twenty-four cubic centimeters (24 cc) are introduced. These diameters and volumes are not limiting, but are presented as an example of the diameter range and pressures utilized with the first preferred occlusion balloon 140.

Figure 7:
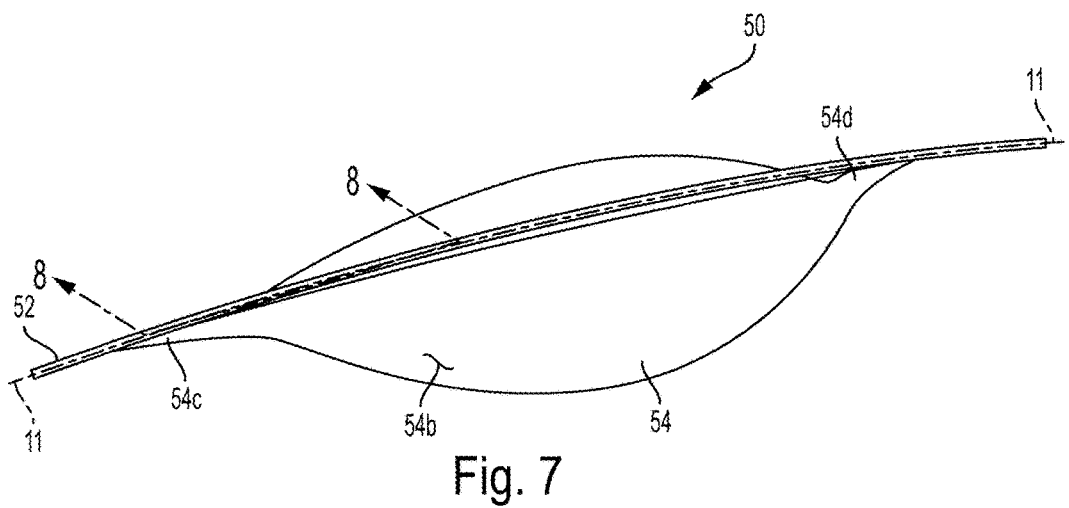
FIG. 7 is a top perspective view of a portion of an occlusion catheter system in accordance with a second preferred embodiment of the present invention, showing an occlusion balloon in an inflated or partially inflated configuration.
Figure 8:
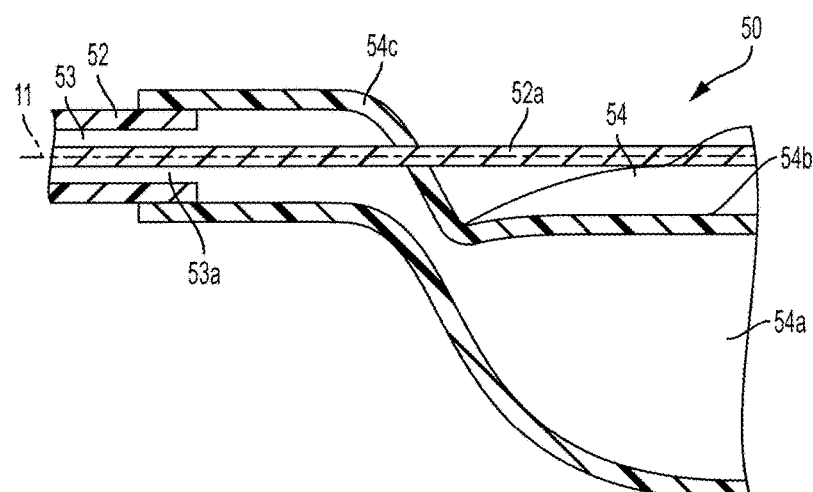
FIG. 8 is a cross-sectional view of the occlusion catheter system of FIG. 7, taken along line 8-8 of FIG. 7.

Referring to FIGS. 7 and 8, a second preferred embodiment of an occlusion catheter system 50 includes an inflation catheter member 52 with a stiffener member 53 therein and an occlusion balloon 54 mounted to the inflation catheter member 52. The inflation catheter member 52 preferably includes the guiding atraumatic tip 450 at its distal end to facilitate insertion of the occlusion catheter system 50 into the large vessel VW, preferably the aorta, of the patient. In the second preferred embodiment, the stiffener member 53 of the inflation catheter member 52 extends through proximal and distal ends 54c, 54d of the occlusion balloon 54, such that the stiffener member 53 is in contact with a portion of an external balloon surface 54b of the occlusion balloon 54 between the proximal and distal ends 54c, 54d. An inflation lumen 53a is preferably defined or formed between an internal surface of the inflation catheter member 52 and an external surface of the stiffener member 53, with the inflation lumen 53a being in fluid communication with an internal balloon space 54a of the occlusion balloon 54. The proximal end 54c of the occlusion balloon 54 is attached to the inflation catheter member 52 such that the inflation lumen 53a is in fluid communication with the internal balloon space 54a and the distal end 54d of the occlusion balloon 54 is attached to the stiffener member 53. The stiffener member 53 is preferably solid and substantially cylindrical in the second preferred embodiment, but is not so limited and may be constructed at a tube with an internal lumen (not shown) for pressure sensing, delivery of medication, introduction of a guide wire or other functions. Alternatively, the stiffener member 53, in this or any of the preferred embodiments, may include the internal lumen that permits use of a guide wire for guiding the system 50 to a preferred location in the patient's vessel VW. Any of the preferred catheter members 12, 52, 52', 1244, 1244', 312, 412, 512, 612, 712, 812, 1412, 1512, 1612, 1712, 1812 described herein may be adapted to include the lumen 15 that extends completely through the catheter member 12, 52, 52', 1244, 1244', 312, 412, 512, 612, 712, 812, 1412, 1512, 1612, 1712, 1812 for use with a guidewire to guide the occlusion balloon 140 to a preferred location.

In operation, the occlusion catheter system 50 is introduced into the patient's vessel VW and the occlusion balloon 54 is positioned where the technician or medical professional desires occlusion of the vessel VW. In an insertion configuration, the occlusion balloon 54 is wrapped or folded onto or around the stiffener member 53, such that the folded occlusion balloon 54 has substantially the same profile or a smaller diameter/profile than the inflation catheter member 52. The profile or diameter of the occlusion catheter system 50 is, therefore, greatest at the connection between the inflation catheter member 52 and the proximal end 54c of the occlusion balloon 54.

When the occlusion catheter system 50 is appropriately positioned in the vessel, the technician or medical professional introduces fluid or gas into the occlusion balloon 54 through the inflation lumen 53a to inflate the inflation balloon 54. The occlusion balloon 54 inflates into the inflated or partially inflated configuration and at least partially engages internal surfaces VS of the vessel VW with the external balloon surface 54b. The stiffener member 53 is also in contact with the external balloon surface 54b along a portion of the occlusion balloon 54 to deform the occlusion balloon 54, substantially parallel to a longitudinal axis 11 of the occlusion catheter system 50. The deformation of the occlusion balloon 54 preferably creates blood flow channels along opposite sides of the stiffener member 53 within the vessel VW or a single blood flow channel between the stiffener member 53, the internal surfaces VS of the vessel VW and the external balloon surface 54b proximate the stiffener member 53. This deformation of the occlusion balloon 54 proximate the stiffener member 53 allows at least partial perfusion of blood flow past the occlusion balloon 54 within the vessel VW. The occlusion balloon 54 may also be designed and configured such that the vessel VW is fully occluded when inflated to a predetermined pressure or within a pressure range.

Figure 9:
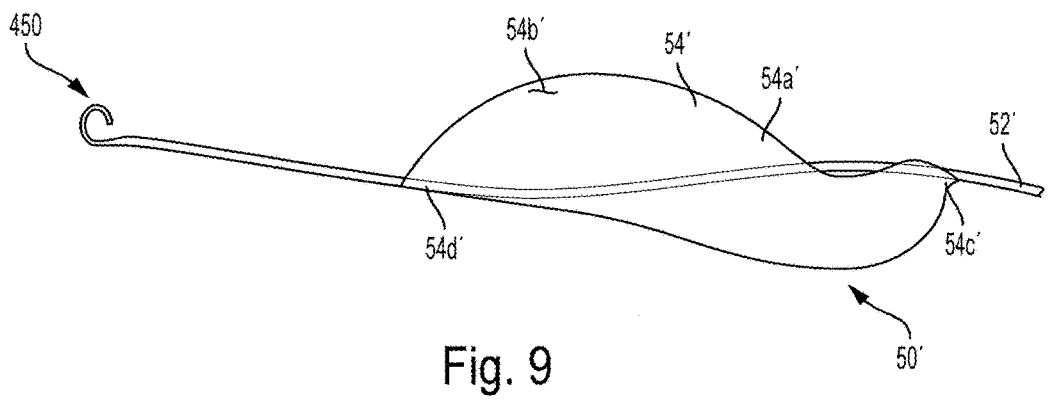
FIG. 9 is a top perspective view of a portion of an occlusion catheter system in accordance with a third preferred embodiment of the present invention, showing an occlusion balloon in an inflated or partially inflated configuration.

Referring to FIG. 9, in a third preferred embodiment an occlusion catheter system 50' has a similar configuration and function when compared to the second preferred occlusion catheter system 50 and the same reference numerals are utilized to identify the same or similar features, with a prime symbol (') utilized to distinguish the third preferred embodiment from the second preferred embodiment. The occlusion catheter system 50' of the third preferred embodiment includes the stiffener member 53' positioned proximate or in facing engagement with the external balloon surface 54b', but the occlusion balloon 54 spirals or is configured to spiral around the stiffener member 53' in an assembled configuration. The external balloon surface 54b' proximate the stiffener member 53', thereby defines or forms a spiral or curved blood flow channel (not shown) between the external balloon surface 54b', the external surface of the stiffener member 53' and the internal surface VS of the vessel VW. In the inflated or partially inflated configuration, the spiral or arcuate blood flow channel is formed, thereby permitting flow of blood through the vessel VW and partial occlusion of the vessel VW.

Referring to FIGS. 7-9, in the second and third preferred embodiments of the occlusion catheter system 50, 50', the stiffener member 53, 53' creates a disruption in a potential seal between the vessel surface VS and the occlusion balloon 54, 54' when the occlusion balloon 54, 54' is in the inflated or partially inflated configuration. By preventing the vessel surface VW from conforming to the external balloon surface 54b, 54b' the stiffener member 53, 53' preferably creates two small flow paths for the blood to flow over the occlusion balloon 54, 54' through the channel for partial occlusion. The facing engagement or contact between the stiffener member 53, 53' and external balloon surface 54b, 54b' with the vessel wall VW being in contact with the internal vessel surface VS stabilizes the occlusion balloon 54, 54', as it is being inflated and deflated during partial occlusion.

Figure 10:
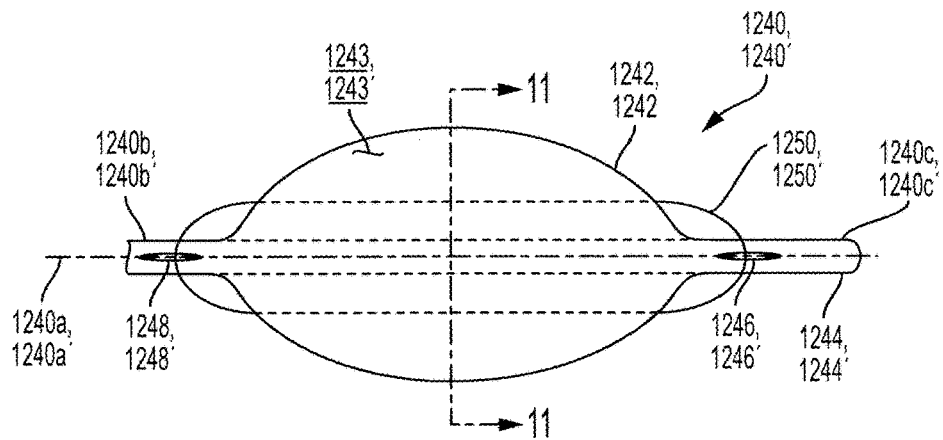
FIG. 10 is a side elevational view of fourth and fifth preferred embodiments of an occlusion catheter system that may be utilized with any of the occlusion catheter systems of the preferred embodiments of the occlusion catheter systems described herein, wherein the occlusion balloon is in an inflated or partially inflated configuration.
Figure 11:
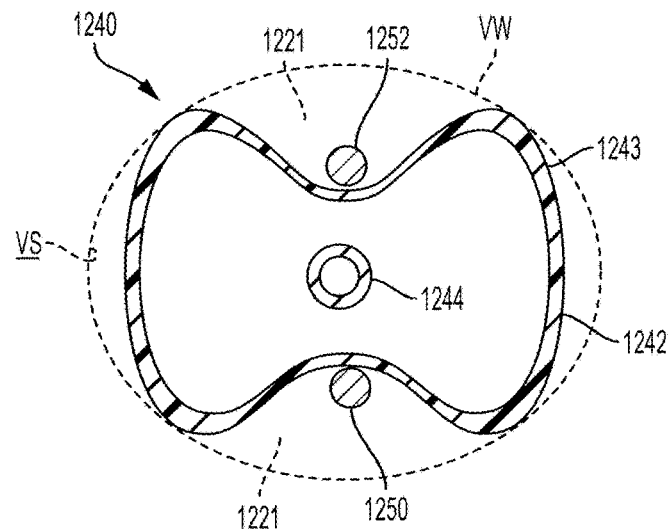
FIG. 11 is a cross-sectional view of the occlusion catheter system of FIG. 10, taken along line 11-11 of FIG. 10 in accordance with the fourth preferred embodiment.
Figure 12:
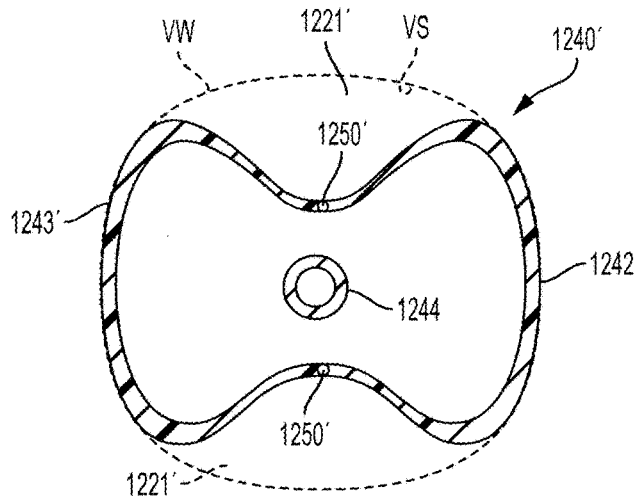
FIG. 12 is a cross-sectional view of the occlusion catheter system of FIG. 10, taken along line 11-11 of FIG. 10, wherein a restraining filament is incorporated into the occlusion perfusion balloon in accordance with the fifth preferred embodiment.

Similar to the second and third preferred embodiments, referring to FIGS. 10-12, fourth and fifth preferred embodiments of the occlusion catheter system 1240, 1240' include a compliant occlusion balloon 1242, 1242' and at least one restraining filament 1250, 1250' connected to proximal and distal catheters 1240b, 1240b', 1240c, 1240c' with the restraining filament 1250, of the fourth preferred embodiment positioned on an outside of an outer surface 1243 of the balloon 1242. The proximal catheter 1240*b*, 1240*b*' includes an inflation lumen (not shown) therein that carries fluid or gas to and from the balloon 1242, 1242' to facilitate inflation and deflation of the balloon 1242, 1242'. The restraining filament 1250, 1250' deforms at least one section of the occlusion balloon 1242, 1242' radially inward toward a longitudinal axis 1240*a*, 1240*a*' of the balloon 1242, 1242' and away from the internal surface VS of the vessel VW or allows an adjacent portion of the balloon 1242, 1242' to extend further away from the longitudinal axis 1240*a*, 1240*a*' than the portion proximate the filament 1240, 1240'. The inclusion of the restraining filament 1250, 1250' preferably creates a reverse curvature in the balloon 1242, 1242' and permits fluid to flow past the balloon 1242, 1242' through a blood flow channel or multiple blood flow channels (not shown). The blood flow channels preferably extend substantially parallel to the longitudinal axis 1240*a*, 1240*a*' when the balloon 1242, 1242' is positioned within the vessel VW and is in the inflated configuration. When a desired time elapses, a desired arterial blood pressure is achieved, or when other indicators suggest, the tension on the restraining filament 1250, 1250' may be released, the reverse curvature preferably expands and the balloon 1242, 1242' preferably returns to its occlusion position in apposition with the vessel surface VS of the vessel VW. At least portions of the external surface 1243, 1243' of the balloon 1242 are consistently in contact with internal surfaces VS of the vessel VW during this inflation and filament 1250 release procedure such that the occlusion balloon 1242 is engaged with the vessel surface VS to limit movement or vibration of the balloon 1242 relative to the vessel VW.

In the occlusion catheter system 1240 of the fourth preferred embodiment, the proximal and distal catheters 1240*b*, 1240*c* accommodate the at least one restraining filament 1250 within the proximal and distal catheters 1240*b*, 1240*c*. The filament 1250 is restrained in the proximal and distal catheters 1240*b*, 1240*c* such that the filament 1250 exits the catheters 1240*b*, 1240*c* near the proximal and distal ends of the balloon 1242 and overlies the balloon 1250 along a portion of the length of the balloon 1250. The filament 1250 is also preferably movable within the proximal catheter 1240*b* so that a user is able to provide tension against the outer surface 1243 of the balloon 1250 to deform the balloon 1250 and define channels or flow paths 1221 between the outer surface 1243 and the inner surface VS of the vessel VW. The channels or flow paths 1221 are preferably oriented substantially parallel to or along the longitudinal axis 1240*a*.

In the fourth preferred embodiment, the catheters 1240*b*, 1240*c* include a distal port 1246 passing through the outer wall of the distal catheter 1240*c* and a proximal port 1248 also passing through the outer wall of the proximal catheter 1240*b*. The restraining filament 1250 preferably traverses from the proximal end of the proximal catheter 1240*b*, where it is accessible to the medical practitioner for tensioning, through a lumen (not shown) in the proximal catheter 1240*b*, exits the proximal port 1248, passes over the balloon 1242 adjacent the outer surface 1243 of the balloon 1242, and anchors or is attached at the distal port 1246 to the distal catheter 1240*c*. In this manner, tensioning the filament 1250 at the proximal end of the proximal catheter 1240*b* causes the filament 1250 to tension against the balloon 1242 or block expansion of the balloon 1242 proximate the filament 1250. When the balloon 1242 is inflated, the portions of the balloon 1242 spaced from the filament 1250 expand away from the longitudinal axis 1240*a*, while the portions of the balloon 1242 adjacent and beneath the filament 1250 are blocked from expansion by the filament 1250. Accordingly, the outer surface 1243 of the balloon 1242 forms or defines the blood flow channels 1221 extending substantially parallel to the longitudinal axis 1240*a* or along the length of the filament 1250 between the expanded portions of the balloon 1242. The channels 1221 permit blood flow through the vessel VW while portions of the outer surface 1243 are in contact with the inside surface VS of the vessel VW.

Referring specifically to FIG. 12, the fifth preferred occlusion catheter system 1240' has similar features in comparison to the fourth preferred occlusion catheter system 1240 and like reference numerals are utilized to identify like features, with a prime symbol (') utilized to distinguish the features of the fifth preferred occlusion catheter system 1240' from the features of the forth preferred occlusion catheter system 1240. In the fifth preferred embodiment, at least one restraining filament 1250' is positioned within the interior space or within the material of the balloon 1242', thereby joining the at least one filament 1250' with the inner wall surface of the balloon 1242'. This joining between the restraining filament 1250' and the inner wall surface of the balloon 1242' may be accomplished by adhesives, thermo-bonding, co-molding or reflowing. Alternatively, one or more lumens may be co-extruded with the inner wall surface of the balloon 1242' or tubular members joined to the inner wall surface of the balloon 1242', and the at least restraining filament 1250' is subsequently positioned within this at least one lumen or tubular member and anchored therein. The balloon 1242' may alternatively be formed from different materials, with the filament 1250' being constructed of a stiffer material than the remainder of the balloon 1242' such that the portion of the balloon 1242' with the filament 1250' therein does not expand at the same rate or to the same extent as the remainder of the balloon 1242'. In this fifth preferred embodiment, the occlusion catheter system 1240' does not necessarily include the proximal port 1248' and the distal port 1246', as the filament 1250' may be positioned within the catheters 1240*b*', 1240*c*' or within a lumen of the catheters 1240*b*', 1240*c*'. The filament 1250' would, therefore, typically not be exposed to the blood vessel VW or blood flow in such a configuration, as the filament 1250' is encased within the balloon 1242' and the catheters 1240*b*', 1240*c*', where the filament 1250 is not exposed to fluid and blood flow during use.

Referring to FIGS. 13 and 14, a sixth preferred embodiment of an occlusion catheter system 100 includes a plurality of occlusion balloons 154*a*, 154*b*, 154*c* carried commonly on an inflation catheter member 152. The plurality of balloons 154*a*, 154*b*, 154*c* may be incorporated with any of the preferred occlusion catheter systems 10, 50, 50', 1240, 1240', described herein. The plurality of balloons 154*a*, 154*b*, 154*c* are preferably, independently expandable though inflation lumens or an inflation lumen (not shown) in the inflation catheter member 152. The inflation lumen preferably communicates independently with each one of the plurality of balloons 154*a*, 154*b*, 154*c*, but is not so limited. In the inflated configuration, each of the balloons 154*a*, 154*b*, 154*c* is preferably in contact with portions of the internal wall VS of the vessel VW, thereby reducing the possibility that the plurality of balloons 154*a*, 154*b*, 154*c* will lose contact with the vessel VW and move or vibrate out of its preferred positioning as a result of partial perfusion of blood past the balloons 154*a*, 154*b*, 154*c*.

Referring to FIGS. 15 and 16, a seventh preferred embodiment of an occlusion catheter system 200 has similarities to the sixth preferred embodiment of the occlusion catheter system 100 and like reference numerals are utilized to identify like features, with a "2" prefix utilized to distinguish the seventh preferred embodiment of the occlusion catheter system 200. The seventh preferred occlusion catheter system 200 includes multiple occlusion balloons 254a, 254b, 254c formed by constraining the occlusion balloon 254 with restraining filaments 270a, 270b. The restraining filaments 270a, 270b provide flexibility in formation of the multiple occlusion balloons 254a, 254b, 254c as they may be shifted along the length of the occlusion balloon 254 to define or form multiple occlusion balloons 254a, 254b, 254c having different sizes and shapes, depending on clinical need. The multiple occlusion balloons 254a, 254b, 254c, similar to the balloons 154a, 154b, 154c of the sixth preferred embodiment, reduce the possibility that the plurality of balloons 254a, 254b, 254c will lose contact with the vessel and move or vibrate out of their preferred positioning as a result of partial perfusion of blood past the balloons 254a, 254b, 254c.

Figure 17:
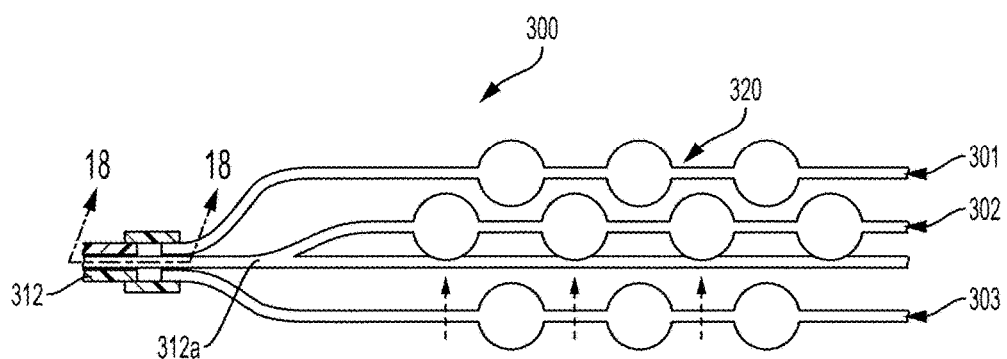
FIG. 17 is a magnified, side elevational view of an occlusion catheter system in accordance with an eighth preferred embodiment, showing occlusion balloon strands in an inflated or partially inflated configuration that may be utilized with any of the preferred catheters described herein.
Figure 18:
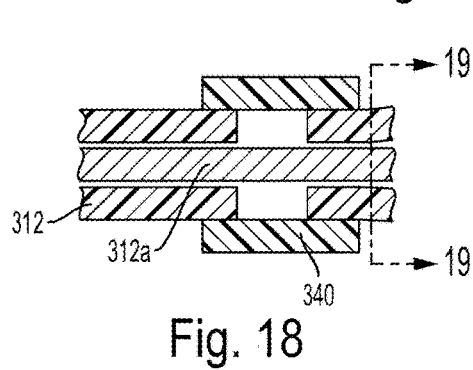
FIG. 18 is a cross-sectional view of the occlusion catheter system of FIG. 17, taken along line 18-18 of FIG. 17.
Figure 19:
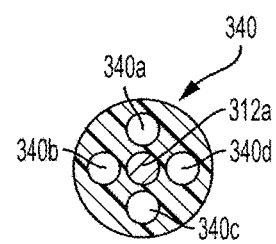
FIG. 19 is a cross-sectional view of the occlusion catheter system of FIG. 17, taken along line 19-19 of FIG. 18.

Referring to FIGS. 17-19, an eighth preferred embodiment of an occlusion catheter system 300 comprises a plurality of occlusion balloon strings 320 that may be utilized to replace any of the preferred occlusion balloons 140, 54, 54', 1240, 1240', 154a, 154b, 154c, 254a, 254b, 254c described herein. The occlusion balloon strings 320 may also be connected to any of the preferred inflation catheter members 12, 52, 52', 1240b, 1240c, 1240b', 1240c', 152, 252, without significantly impacting the function of the preferred occlusion catheter system 300 of the eighth preferred embodiment.

In the eighth preferred embodiment, the occlusion balloon strings 320 include individual balloon strands 301, 302, 303 with multiple occlusion balloons mounted thereon along a length of the occlusion catheter system 300. The individual balloon strands 301, 302, 303 are connected to a manifold 340, which is connected to an inflation catheter member 312. The manifold 344 includes multiple exit ports 340a, 340b, 340c, 340d that are associated with the balloon strands 301, 302, 303 to provide individual fluid communication with each of the balloon strands 301, 302, 303. The individual occlusion balloons on the balloon strands 301, 302, 303 are preferably, but not necessarily, staggered along the length of the occlusion catheter system 300 to maximize or facilitate seating and packing of the individual balloons in an inflated configuration. A stiffener member 312a preferably extends through and past the balloon strands 301, 302, 303 to structurally support the balloon strands 301, 302, 303 and a distal end (not shown) of the occlusion catheter system 300, which preferably includes the atraumatic tip 450.

In operation, the occlusion catheter system 300 of the eighth preferred embodiment is inserted into the vessel VW so that the balloon strands 301, 302, 303 are positioned in the vessel VW where occlusion or partial occlusion is desired. Fluid or gas is introduced into the balloon strands 301, 302, 303 to inflate the balloon strands 301, 302, 303, including the individual balloons. The fluid is directed to the appropriate balloon strands 301, 302, 303 by the multiple exit ports 340a, 340b, 340c, 340d in the manifold 340. The exit ports 340a, 340b, 340c, 340d may be selectively opened or closed to permit flow of the fluid or gas into the respective balloon strands 301, 302, 303, thereby inflating, partially inflating or not inflating the strands 301, 302, 303, respectively. When the balloon strands 301, 302, 303 are in the inflated or partially inflated configuration, the individual balloons pack or seat against each other to prevent resistance to the flow of blood through the vessel VW. At least portions of the individual balloons of the strands 301, 302, 303 are in contact with the inside surface VS of the vessel VW in the inflated configuration to secure the occlusion balloon strings 320 relative to the vessel VW while blood is partially perfusing through the vessel VW along the strings 320. The amount of resistance may be at least partially controlled by the inflation of the strands 301, 302, 303, the number of strands 301, 302, 303, the length of the strands 301, 302, 303, the shape of the individual balloons, the materials utilized to construct the strands 301, 302, 303, the number of strands 301, 302, 303 that are inflated or partially inflated, and other factors related to the strands 301, 302, 303 and the preferred occlusion catheter system 300. For full inclusion, the individual balloons preferably pack tightly together to prevent blood flow through the vessel VW or are at least partially compliant to form to the shape of the vessel VW in the inflated configuration.

Figure 20:
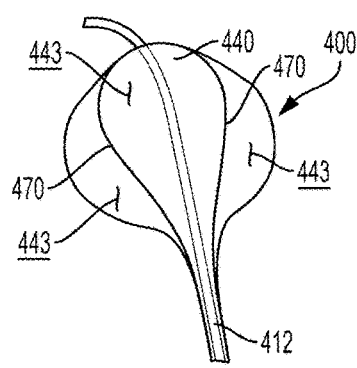
FIG. 20 is a rear perspective view of an occlusion catheter system in accordance with a ninth preferred embodiment, showing an occlusion balloon in an inflated or partially inflated configuration that may be utilized with any of the preferred catheters described herein.

Referring to FIG. 20, a ninth preferred embodiment of an occlusion catheter system 400 comprises an occlusion balloon 440 that may be utilized to replace any of the preferred occlusion balloons 140, 54, 54', 1240, 1240', 154a, 154b, 154c, 254a, 254b, 254c. The occlusion balloon 440 of the ninth preferred embodiment is constrained by longitudinal straps 470 that connect to an inflation catheter member 412, which may comprise any of the preferred inflation catheter members 12, 52, 52', 1240b, 1240c, 1240b', 1240c', 152, 252, without significantly impacting the function of the preferred occlusion catheter system 400 of the ninth preferred embodiment. The longitudinal straps 470 constrain the inflation of the occlusion balloon 440, thereby creating blood flow channels (not shown) along the length of the occlusion balloon 440 in the inflated configuration to allow partial flow of blood past the occlusion balloon 440. The blood flow channels are formed between an outer surface 443 of the balloon 440 and the inner surfaces VS of the vessel VW.

Figure 21:
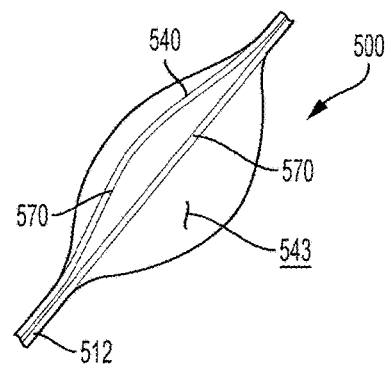
FIG. 21 is a top perspective view of an occlusion catheter system in accordance with a tenth preferred embodiment, showing an occlusion balloon in an inflated or partially inflated configuration that may be utilized with any of the preferred catheters described herein.

Referring to FIG. 21, a tenth preferred embodiment of an occlusion catheter system 500 comprises an occlusion balloon 540 that may be utilized to replace any of the preferred occlusion balloons 140, 54, 54', 1240, 1240', 154a, 154b, 154c, 254a, 254b, 254c. The occlusion balloon 540 of the tenth preferred embodiment is preferably constrained by compliant longitudinal straps 570 that connect to an inflation catheter member 512. The inflation catheter member 512 may be configured and constructed in the same or a similar fashion to any of the preferred inflation catheter members 12, 52, 52', 1240b, 1240c, 1240b', 1240c', 152, 252 described herein, without significantly impacting the function of the preferred occlusion catheter system 500 of the tenth preferred embodiment. The longitudinal straps 570 constrain inflation of the occlusion balloon 540, thereby creating blood flow channels along the length of the occlusion balloon 540 in the inflated or partially inflated configurations to allow partial flow of blood past the occlusion balloon 540 when inserted into the vessel VW.

Figure 22:
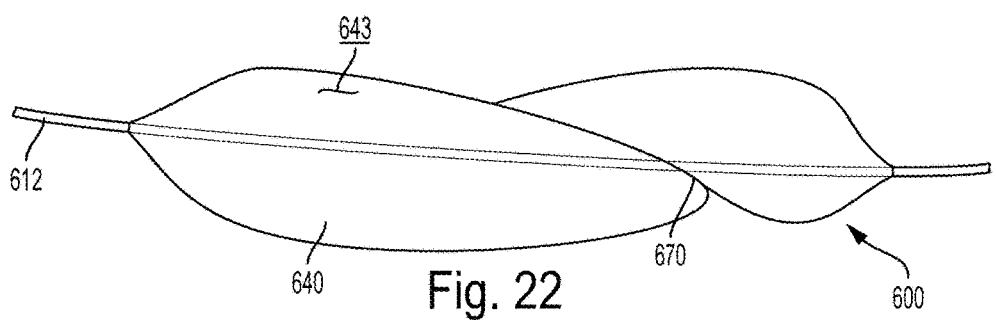
FIG. 22 is a side perspective view of an occlusion catheter system in accordance with an eleventh preferred embodiment, showing an occlusion balloon in an inflated or partially inflated configuration that may be utilized with any of the preferred catheters described herein.

Referring to FIG. 22, an eleventh preferred embodiment of an occlusion catheter system 600 comprises an occlusion balloon 640 that may be utilized to replace any of the preferred occlusion balloons 140, 54, 54', 1240, 1240', 154a, 154b, 154c, 254a, 254b, 254c. The occlusion balloon 640 of the eleventh preferred embodiment is preferably constrained by a fiber constraint 670, such as a Nylon fiber, that connects to an inflation catheter member 612 on either end of the occlusion balloon 612. The inflation catheter member 612 may comprise any of the preferred inflation catheter members 12, 52, 52', 1240b, 1240c, 1240b', 1240c', 152, 252, without significantly impacting the function of the preferred occlusion catheter system 600 of the eleventh preferred embodiment. The fiber constraint 670 constrains the inflation of the occlusion balloon 640, thereby creating a substantially spiral or arcuate blood flow channel along the length of the occlusion balloon 640 between an outer surface 643 of the balloon and the inner surface VS of the vessel VW in the inflated configuration to allow partial flow of blood past the occlusion balloon 640.

Figure 23:
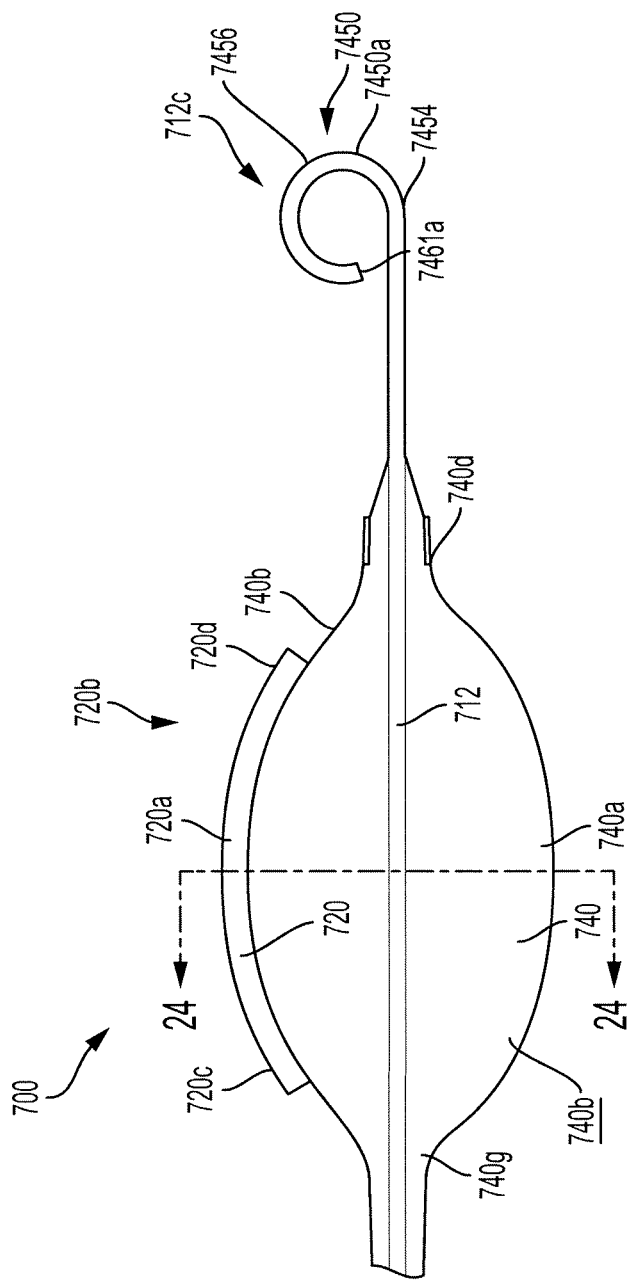
FIG. 23 is a side elevational view of a distal portion of an occlusion catheter system in accordance with a twelfth preferred embodiment, showing an occlusion balloon in an inflated or partially inflated configuration that may be utilized with any of the preferred catheters described herein.
Figure 24:
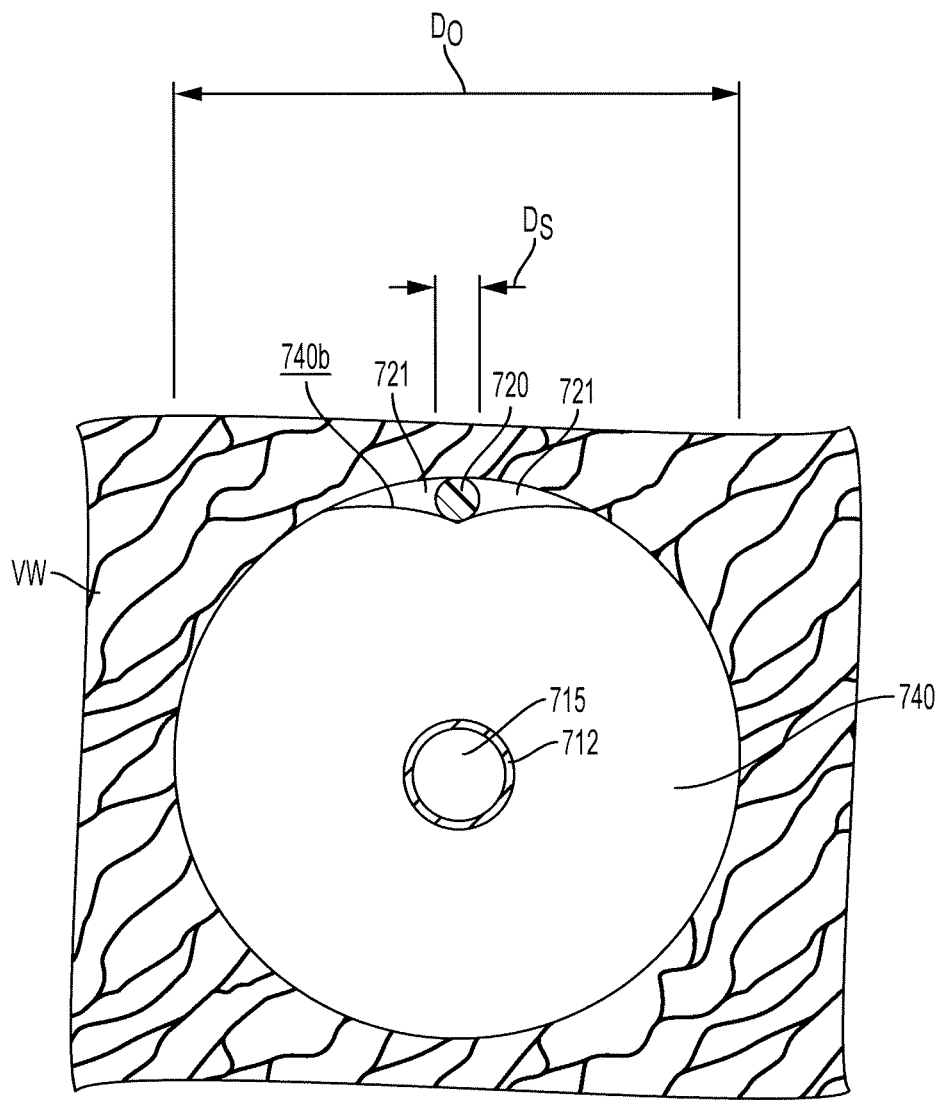
FIG. 24 is a cross-sectional view of the occlusion catheter system of FIG. 23 positioned within a vessel, taken along lines 24-24 of FIG. 23.

Referring to FIGS. 23 and 24, a twelfth preferred embodiment of an occlusion catheter system 700 includes an occlusion balloon 740 with a spine 720 mounted longitudinally on an external balloon surface 740*b*. The twelfth preferred occlusion catheter system 700 has similar features to the first preferred occlusion catheter system 10 and similar reference numbers are utilized to identify similar features between the first and twelfth preferred embodiments, with a "7" prefix utilized to distinguish the features of the twelfth preferred embodiment. The twelfth preferred occlusion catheter system 700 also preferably includes a distal catheter end 712*c* that is similar to or the same as the atraumatic tip 450 described in FIGS. 4 and 5. The atraumatic tip of the twelfth preferred embodiment is, therefore, identified by reference number 7450 and relevant features of the atraumatic tip 7450 are similarly numbered with the "7" prefix.

The spine 720 of the twelfth preferred embodiment is a solid polymeric component attached to the external surface 740*b* of the occlusion balloon 740 with proximal and distal spine ends 720*c*, 720*d* stopping short of the proximal and distal balloon ends 740*c*, 740*d*. The spine 720 of the twelfth preferred embodiment has a substantially constant spine diameter $D_S$ based on its solid polymeric construction and is not configured for over-driving and flattening, as was described above with the first preferred inflatable spine 20. The spine 720 of the twelfth preferred embodiment is not limited to being substantially solid or to being constructed of a polymeric material. The spine 720 may alternatively be constructed of a balloon attached to the occlusion balloon 740 that is inflated concurrently or separately from the inflation of the occlusion balloon 740. The spine 720 may alternatively be constructed of a tube or hollow cylinder that is attached to the external surface 740*b* that defines a channel through the tube in the inflated configuration. The preferred spine 720 is attached to the external surface 740*b* of the occlusion balloon 740 to prevents the occlusion balloon 740 from sealing against inner surfaces VS of the vessel wall VW within which the occlusion balloon 740 is inserted and inflated. The spine 720, therefore, creates leak paths or flow channels 721 along the vessel VW to permit blood flow to pass the occlusion balloon 740 in the inflated configuration. In the twelfth preferred embodiment, a single spine 720 is mounted to the occlusion balloon 740, however, the single spine 720 is not limiting and the occlusion balloon 740 may include two or more spines 720 mounted on the external surface 740*b* to create more leak paths or flow paths 721 within the vessel VW.

Referring to FIGS. 25A-25C, a thirteenth preferred embodiment of an occlusion catheter system 800 includes an occlusion balloon 840 with several spines or balloon spines 820*x*, 820*y*, 820*z* mounted along an external balloon surface 840*b*. The balloon spines 820*x*, 820*y*, 820*z* preferably wrap arcuately around the circumference of the external balloon surface 840*b* and are attached to the catheter member 812 near proximal and distal ends of the balloon 840. The thirteenth preferred occlusion catheter system 800 has similar features to the first preferred occlusion catheter system 10 and similar reference numbers are utilized to identify similar features between the first and thirteenth preferred embodiments, with an "8" prefix utilized to distinguish the features of the thirteenth preferred embodiment. The thirteenth preferred occlusion catheter system 800 also preferably includes a distal catheter end 812*c* that is similar or the same as the atraumatic tip 450 described in FIGS. 4 and 5. The atraumatic tip 812*c* of the thirteenth preferred embodiment is, therefore, identified by reference number 8450 and relevant features of the atraumatic tip 8450 are similarly numbered with the "8" prefix.

The several or multiple balloon spines 820*x*, 820*y*, 820*z* of the thirteenth preferred embodiment are connected at their proximal ends to the catheter member 812 by separate lumens 813*x*, 813*y*, 813*z*. The separate lumens 813*x*, 813*y*, 813*z* may be connected to individual inflation ports (not shown) that permit individual inflation or deflation of the multiple balloon spines 820*x*, 820*y*, 820*z* by a medical technician or physician or may all be in fluid communication with a single inflation port for inflation and deflation of the multiple balloon spines 820*x*, 820*y*, 820*z* and/or the occlusion balloon 840 concurrently, thereby permitting individual inflation and deflation, concurrent inflation and deflation or inflation and deflation in stages based upon how many inflation ports are included and their fluid communication with the multiple balloon spines 820*x*, 820*y*, 820*z* and/or the occlusion balloon 840. The multiple balloon spines 820*x*, 820*y*, 820*z* define multiple flow channels or leak paths (not shown) in the inflated configuration, thereby potentially permitting additional blood flow along the vessel VW in the inflated configuration.

Figure 26:
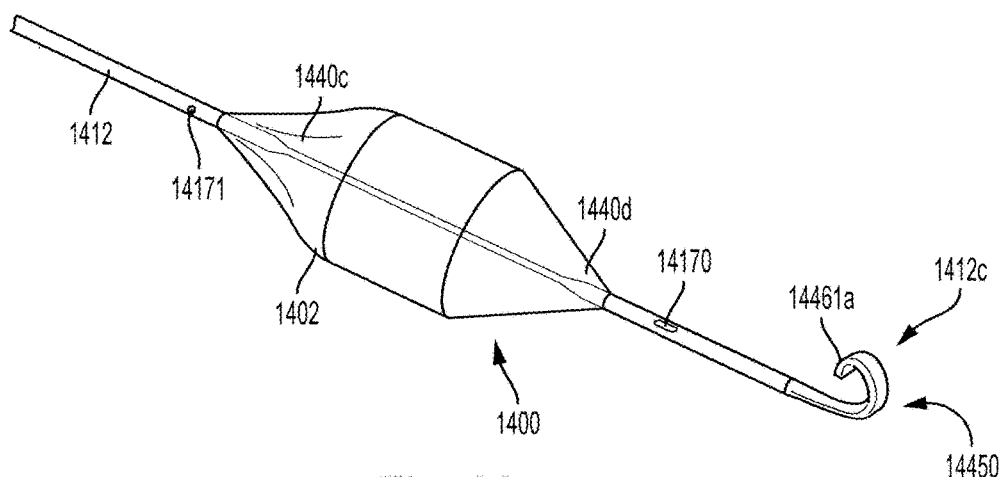
FIG. 26 is a top perspective view of a portion of an occlusion catheter system in accordance with a fourteenth preferred embodiment of the present invention, showing occlusion balloons in an inflated or partially inflated configuration that may be utilized with any of the preferred catheters described herein.
Figure 27:
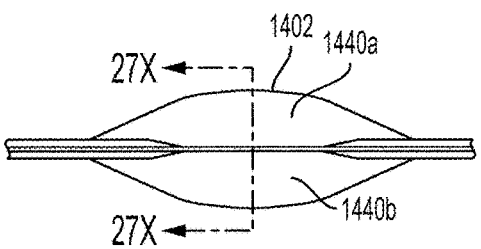
FIG. 27 is a top plan view of a portion of the occlusion catheter system of FIG. 26, showing the occlusion balloons in the inflated or partially inflated configuration.
Figure 27A:
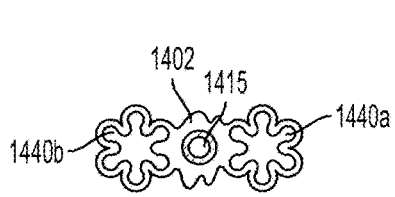
FIG. 27A is a cross-sectional view of the occlusion catheter system of FIG. 26, taken along line 27X-27X of FIG. 27 with the occlusion balloons in a substantially uninflated or deflated configuration.
Figure 27B:
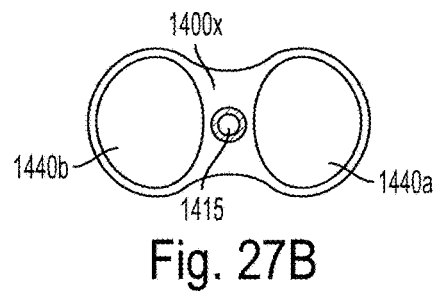
FIG. 27B is a cross-sectional view of the occlusion catheter system of FIG. 26, taken along line 27X-27X of FIG. 27 with the occlusion balloons in an approximately twenty-five percent (25%) inflated configuration.
Figure 27C:
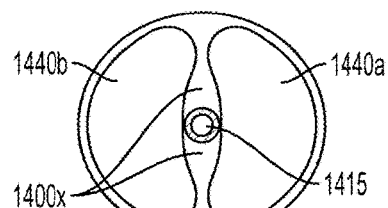
FIG. 27C is a cross-sectional view of the occlusion catheter system of FIG. 27, taken along line 27X-27X of FIG. 27 with the occlusion balloons in an approximately fifty percent (50%) inflated configuration.
Figure 27D:
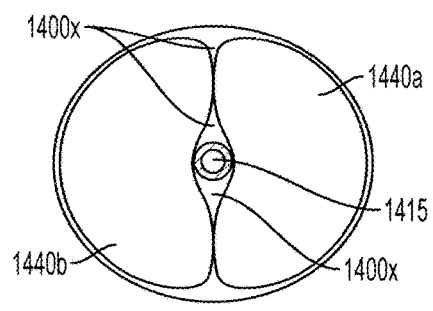
FIG. 27D is a cross-sectional view of the occlusion catheter system of FIG. 27, taken along line 27X-27X of FIG. 27 with the occlusion balloons in a substantially inflated configuration.

Referring to FIGS. 26-27D, a fourteenth preferred embodiment of an occlusion catheter system 1400 includes a first occlusion balloon 1440*a* and a second occlusion balloon 1440*b* that together have a similar function as the occlusion balloon 140 of the first preferred occlusion catheter system 10, but without the inclusion of the balloon spine 20. The fourteenth preferred embodiment includes a substantially flexible sleeve 1402 that wraps around the first and second occlusion balloons 1440*a*, 1440*b* to facilitate a substantially circular shape of the combined occlusion balloons 1440*a*, 1440*b* in partially and inflated configurations and to compact the first and second occlusion balloons 1440*a*, 1440*b* around the hypotube of the catheter 1412 in an uninflated configuration (FIG. 27A). The fourteenth preferred occlusion catheter system 1400 has similar features to the first preferred occlusion catheter system 10 and similar reference numbers are utilized to identify similar features between the first and fourteenth preferred embodiments, with a "14" prefix utilized to distinguish the features of the fourteenth preferred embodiment. The fourteenth preferred occlusion catheter system 1400 also preferably includes a distal catheter end 1412*c* that is similar or the same as the atraumatic tip 450 described in FIGS. 4 and 5. The atraumatic tip 1412*c* of the fourteenth preferred embodiment is, therefore, identified by reference number 14450 and relevant features of the atraumatic tip 14450 are similarly numbered with the "14" prefix.

In the fourteenth preferred embodiment, the first and second occlusion balloons 1440*a*, 1440*b* are preferably approximately the same size, are positioned on either side of the hypotube of the catheter 1412 and are connected at their proximal and distal ends 1440*c*, 1440*d* to the catheter 1412. The first and second occlusion balloons 1440*a*, 1440*b* are preferably connected to the same inflation lumen (not shown), but are not so limited and may be connected to individual inflation lumens (not shown) for selective inflation of the first and second occlusion balloons 1440*a*, 1440*b*.

In the fourteenth preferred embodiment, the flexible sleeve 1402 is comprised of a flexible laminate membrane that generally holds the first and second occlusion balloons 1440a, 1440b in a generally cylindrical shape as the occlusion balloons 1440a, 1440b are inflated. The first and second occlusion balloons 1440a, 1440b are compliant or partially compliant to allow inflation expansion to occlusion of the flexible sleeve's 1402 annular space. As the first and second occlusion balloons 1440a, 1440b are inflated from the uninflated configuration (FIG. 27A) to the substantially fully inflated configuration (FIG. 27D), flow channels or leak paths 1400x are defined between the outer surfaces of the hypotube of the catheter 1412, the outer surface of the occlusion balloons 1440a, 1440b and inner surfaces of the flexible sleeve 1402. The flow channels or leak paths 1400x allow at least partial flow of blood through the vessel VW and past the occlusion balloons 1440a, 1440b. Referring to FIGS. 27A-27D, the first and second occlusion balloons 1440a, 1440b are shown being inflated from the uninflated configuration (FIG. 27A), to an approximately twenty-five percent (25%) inflation configuration (FIG. 27B), to an approximately fifty percent (50%) inflation configuration (FIG. 27C), to a nearly fully inflated or ninety-five percent (95%) inflation configuration (FIG. 27D).

Figure 28:
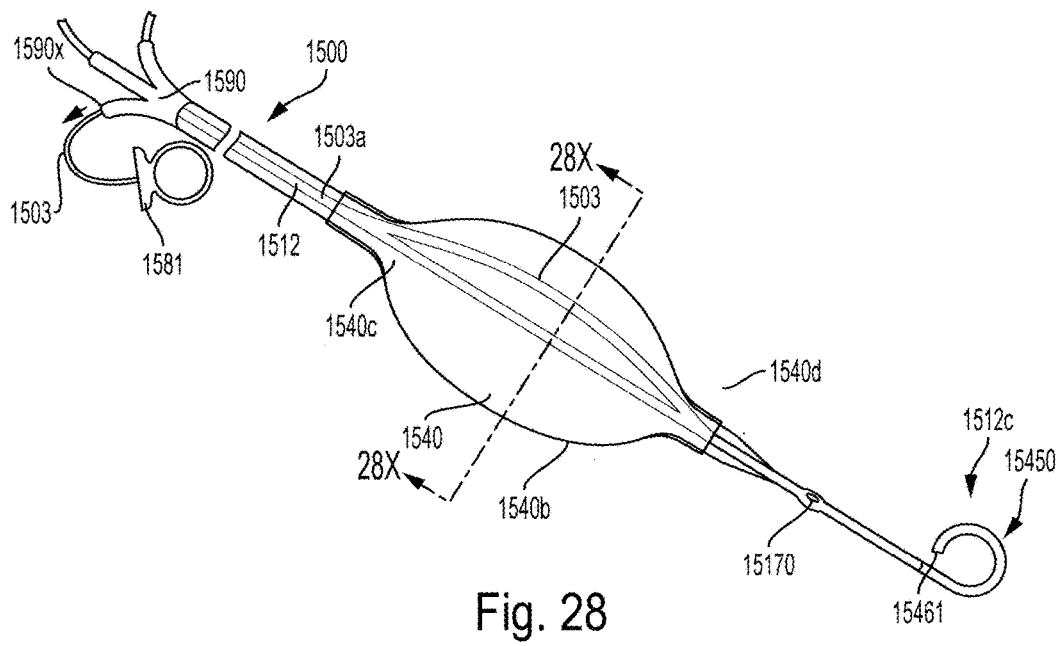
FIG. 28 is a top perspective view of an occlusion catheter system in accordance with a fifteenth preferred embodiment of the present invention with the occlusion balloon in a fully or partially inflated configuration and a flexible strap extending along an outer surface of the occlusion balloon.
Figure 28A:
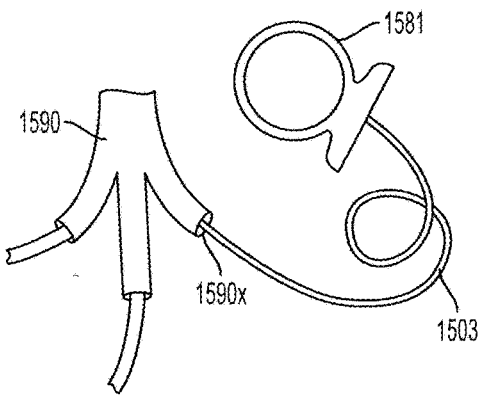
FIG. 28A is a magnified top plan view of an inflation hub of the occlusion catheter system of FIG. 28.
Figure 28B:
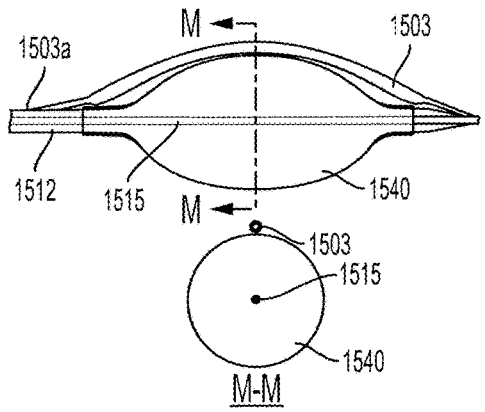
FIG. 28B is a cross-sectional view along line 28X-28X of FIG. 28 and a side elevational view of the occlusion balloon in a fully or partially inflated configuration and a flexible strap substantially untensioned.
Figure 28C:
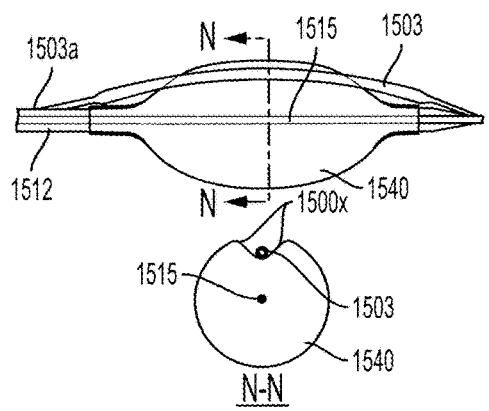
FIG. 28C is a cross-sectional view along line 28X-28X of FIG. 28 and a side elevational view of the occlusion balloon in a fully or partially inflated configuration and the flexible strap tensioned.

Referring to FIGS. 28-28C, a fifteenth preferred embodiment of an occlusion catheter system 1500 includes an occlusion balloon 1540 with a flexible strap 1503 attached to a distal portion of the catheter member 1512 and slidably mounted in an inflation hub 1590. The fifteenth preferred occlusion catheter system 1500 has similar features to the first preferred occlusion catheter system 10 and similar reference numbers are utilized to identify similar features between the first and fifteenth preferred embodiments, with a "15" prefix utilized to distinguish the features of the fifteenth preferred embodiment. The fifteenth preferred occlusion catheter system 1500 also preferably includes a distal catheter end 1512c that is similar or the same as the atraumatic tip 450 described in FIGS. 4 and 5. The atraumatic tip 1512c of the fifteenth preferred embodiment is, therefore, identified by reference number 15450 and relevant features of the atraumatic tip 15450 are similarly numbered with the "15" prefix.

The flexible strap 1503 is preferably fixed to the distal portion of the catheter member 1512, is positioned along the external surface 1540b of the occlusion balloon 1540, slides through an opening 1503a in the catheter 1512 near the proximal occlusion balloon end 1540c, through the proximal portion of the catheter 1512, through a lumen in the inflation hub 1590 and out of an opening 1590x at the proximal end of the inflation hub 1590. A strap handle 1581 is connected to a proximal end of the flexible strap 1503 that a medical practitioner or physician is able to manipulate to apply pressure to the external surface 1540b of the occlusion balloon 1540 toward the hypotube 1515 of the catheter member 1512 to deform the occlusion balloon 1540 and create or define flow channels or leak paths 1500x between the external surface 1540b of the occlusion balloon 1540, the flexible strap 1503 and the internal surfaces VS of the vessel VW in the inflated or partially inflated configuration of the occlusion balloon 1540. The flexible strap 1503 may also be untensioned and lie on the external surface 1540b of the occlusion balloon 1540 such that the external surface 1540b of the occlusion balloon 1540 is positioned against the internal surface VS of the vessel VW to fully occlude the vessel VW. The medical technician or physician is therefore able to selective create full occlusion to various levels of partial occlusion of the vessel VW by applying various levels of tension to the flexible strap 1503.

Figure 29:
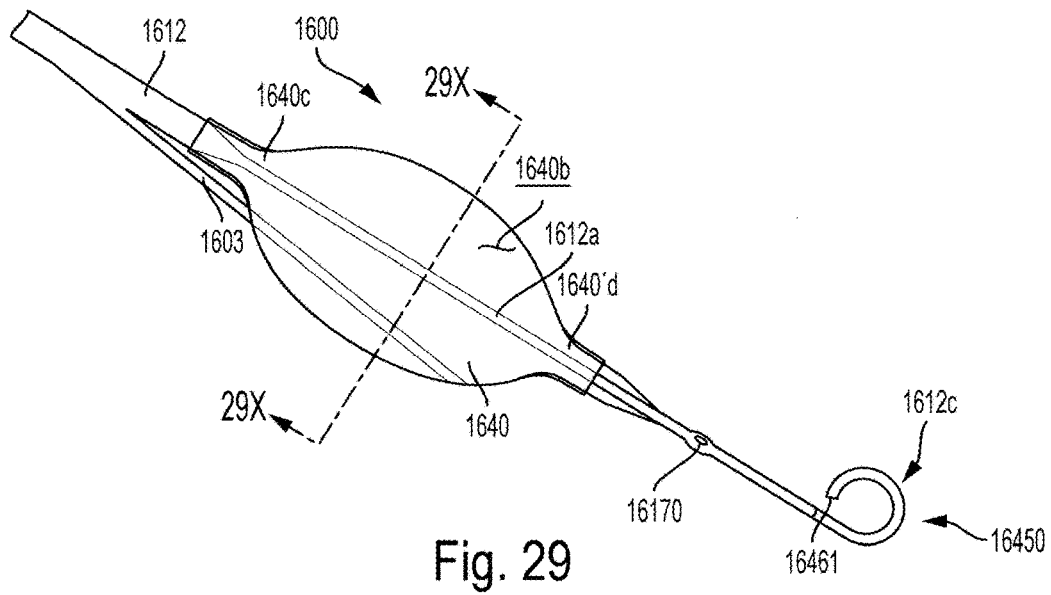
FIG. 29 is a top perspective view of an occlusion catheter system in accordance with a sixteenth preferred embodiment of the present invention with the occlusion balloon in a fully or partially inflated occlusion balloon and a twisting rod.
Figure 29A:
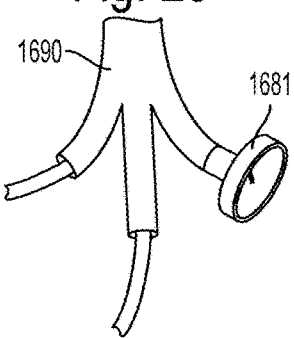
FIG. 29A is a magnified top plan view of an inflation hub of the occlusion catheter system of FIG. 29.
Figure 29B:
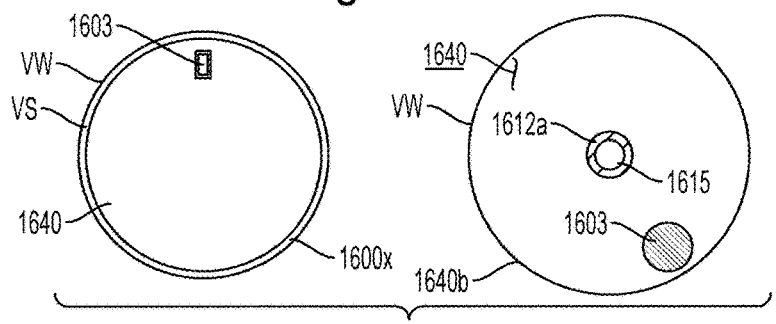
FIGS. 29B and 29C are cross-sectional views of the occlusion catheter system of FIG. 29, taken along line 29X-29X of FIG. 29.
Figure 29C:
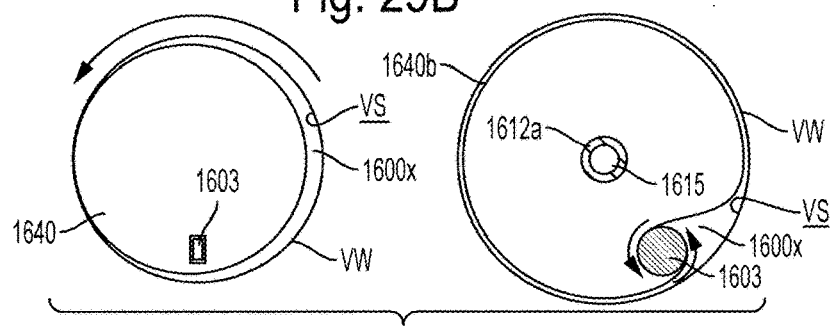

Referring to FIGS. 29-29C, a sixteenth preferred embodiment of an occlusion catheter system 1600 includes an occlusion balloon 1640 with a twisting rod 1603 attached to the external balloon surface 1640b of the occlusion balloon 1640 and pivotably mounted in an inflation hub 1690. The sixteenth preferred occlusion catheter system 1600 has similar features to the first preferred occlusion catheter system 10 and similar reference numbers are utilized to identify similar features between the first and sixteenth preferred embodiments, with a "16" prefix utilized to distinguish the features of the sixteenth preferred embodiment. The sixteenth preferred occlusion catheter system 1600 also preferably includes a distal catheter end 1612c that is similar to or the same as the atraumatic tip 450 described in FIGS. 4 and 5. The atraumatic tip 1612c of the sixteenth preferred embodiment is, therefore, identified by reference number 16450 and relevant features of the atraumatic tip 16450 are similarly numbered with the "16" prefix.

The twisting rod 1603 is preferably fixed and pivotably attached to the proximal portion of the catheter member 1612 and is positioned on and attached to the external surface 1640b of the occlusion balloon 1640. A twisting rod handle 1681 is connected to a proximal end of the twisting rod 1603 that a medical practitioner or physician is able to manipulate to deform the external surface 1640b of the occlusion balloon 1640 toward the hypotube 1612a of the catheter member 1612 to deform the occlusion balloon 1640 and create or define flow channels or leak paths 1600x between the external surface 1640b of the occlusion balloon 1640, the twisting rod 1603 and the internal surfaces VS of the vessel VW in the inflated or partially inflated configuration of the occlusion balloon 1640. The twisting rod 1603 may also be untensioned and lie on the external surface 1640b of the occlusion balloon 1640 such that the external surface 1640b of the occlusion balloon 1640 is positioned against the internal surface VS of the vessel VW to fully occlude the vessel VW. The medical technician or physician is therefore able to selectively create full occlusion to various levels of partial occlusion of the vessel VW by applying various levels of tension to the twisting rod 1603.

Figure 30:
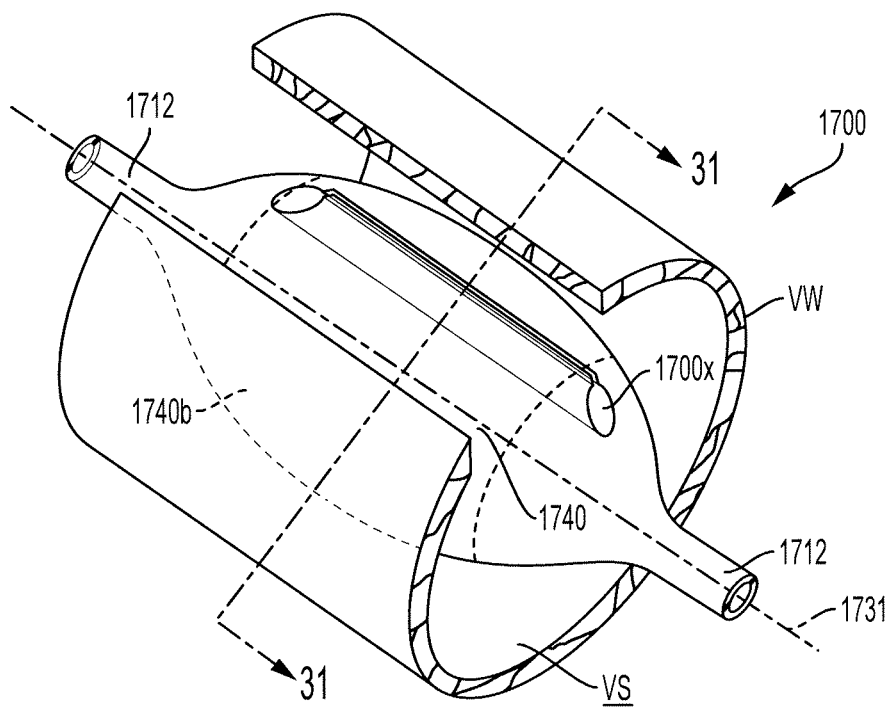
FIG. 30 is a top perspective view of an occlusion balloon in accordance with a seventeenth preferred embodiment of the present invention that may be utilized with any of the preferred catheters described herein.
Figure 31:
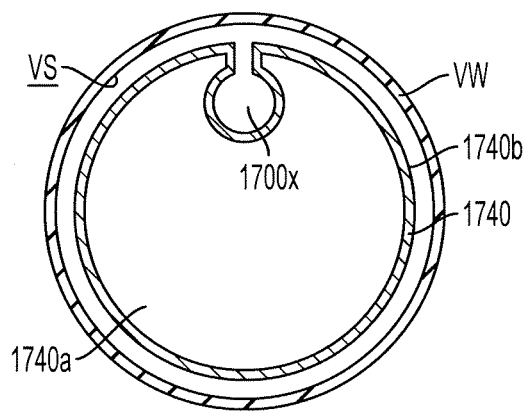
FIG. 31 is a cross-sectional view of the occlusion balloon taken along line 31-31 of FIG. 30 with the occlusion balloon in an inflated or partially inflated configuration.

Referring to FIGS. 30 and 31, a preferred occlusion balloon 1740 in accordance with a seventeenth preferred embodiment of an occlusion catheter system 1700 includes an occlusion balloon 1740 with a flow channel 1700X defined at a peripheral side of the balloon 1740. The seventeenth preferred occlusion balloon 1740 may be utilized with any of the preferred occlusion catheter systems described herein. In the seventeenth preferred embodiment, the occlusion balloon 1740 is substantially compliant and the flow channel 1700X is pre-formed at the periphery of the balloon 1750. The flow channel 1700X runs along or substantially parallel to a longitudinal axis 1731 of the occlusion balloon 1740 to permit partial flow of blood past the occlusion balloon 1740. The seventeenth preferred occlusion balloon 1731 could me mounted to any of the preferred occlusion catheter systems described herein without significantly impacting the functions of the preferred systems.

Figure 32:
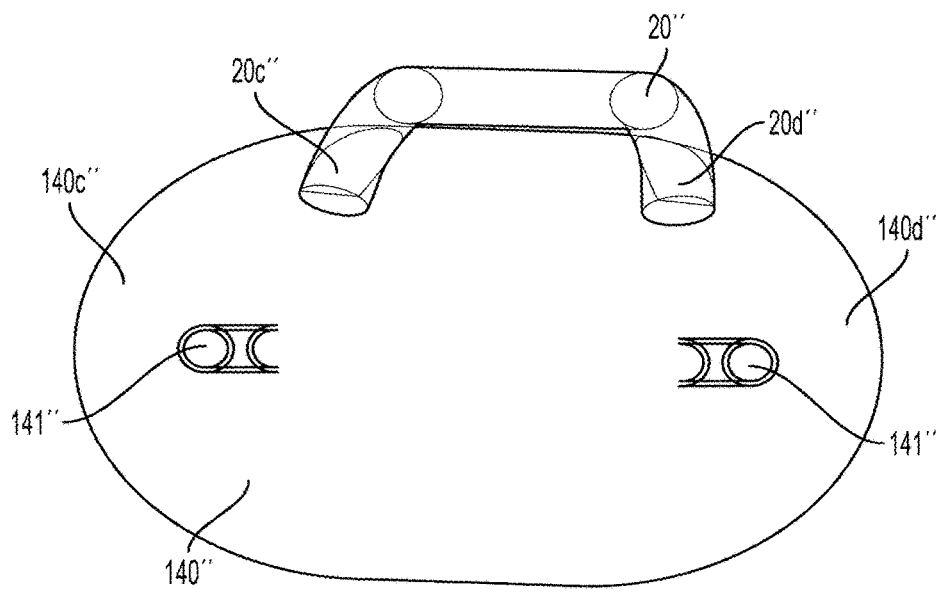
FIG. 32 is a top plan, partially exploded view of an alternative preferred embodiment of an occlusion balloon that may be utilized with any of the occlusion catheter systems of the present invention, including the occlusion catheter system of FIG. 1, wherein a balloon spine is exploded from an occlusion balloon.
Figure 33:
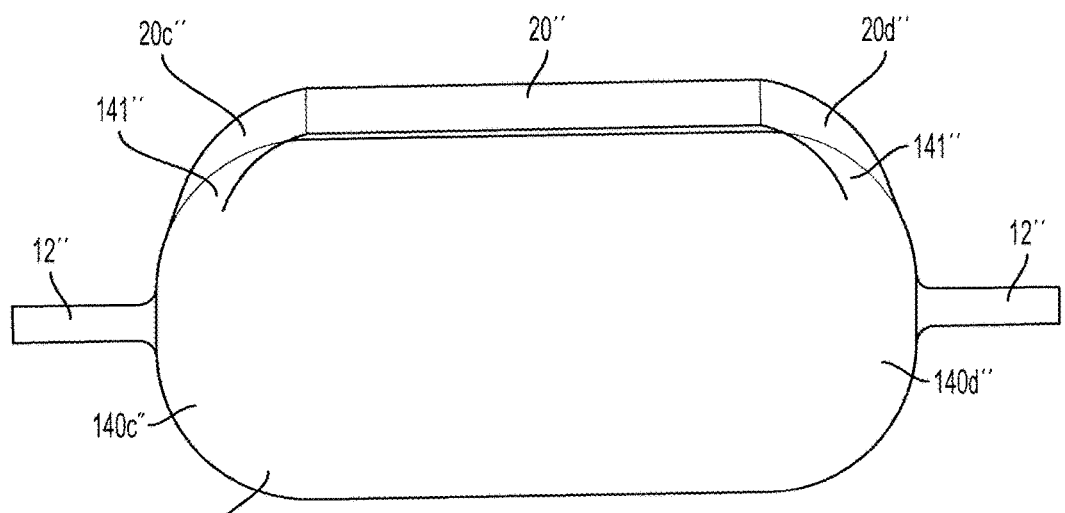
FIG. 33 is a side elevational view of the occlusion balloon of FIG. 32.

Referring to FIGS. 32 and 33, in an alternative preferred embodiment of an occlusion balloon assembly may be utilized with any of the preferred occlusion balloon systems described herein, such as the first preferred occlusion balloon system 10, a balloon spine 20″ is connected at domed portions at proximal and distal balloon ends 140c″, 140d″ of the occlusion balloon 140″. This alternative preferred occlusion balloon assembly has a similar configuration and function when compared to the first preferred occlusion balloon assembly and the same reference numerals are utilized to identify the same or similar features, with a double-prime symbol (″) utilized to distinguish this alternative preferred embodiment from the first preferred embodiment. The occlusion balloon 140″ of this alternative preferred embodiment includes attachment ports 141″ in domed portions of the occlusion balloon 140″ in the proximal and distal balloon ends 140c″, 140d″. The connections at the attachment ports 141″ provide fluid flow channels into the spine 20″ from the inside of the occlusion balloon 140″ such that the spine 20″ and occlusion balloon 140″ fill at the same pressure during inflation and are likewise deflated to the same or similar pressures. The attachment ports 141″ may be integrally formed with the balloon 140″ or may be comprised of mechanical or adhesive bonding of the spine 20″ to the occlusion balloon 140″.

Figure 34:
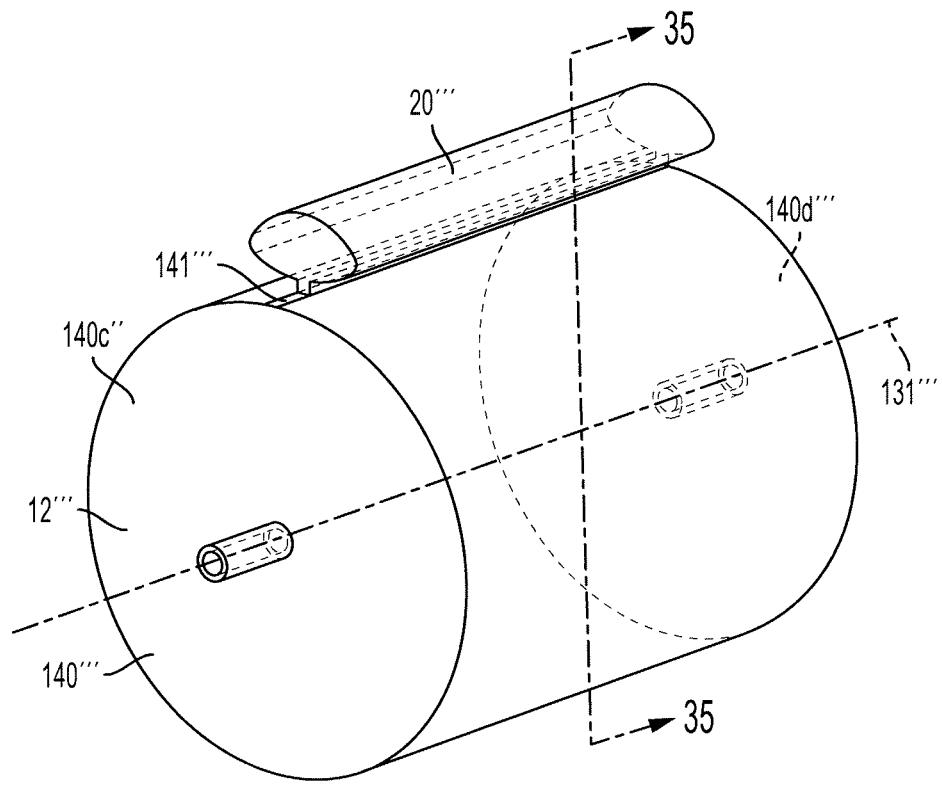
FIG. 34 is a side perspective view of an alternative preferred embodiment of an occlusion balloon assembly that may be utilized with any of the occlusion catheter systems of the present invention, including the occlusion catheter system of FIG. 1.
Figure 35:
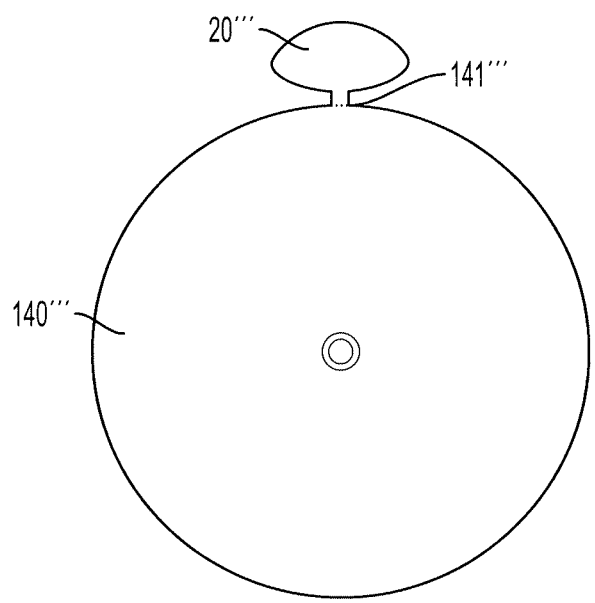
FIG. 35 is a cross-sectional view of the balloon assembly of FIG. 34, taken along line 35-35 of FIG. 34.

Referring to FIGS. 34 and 35, in a further alternative preferred embodiment of an occlusion balloon 140‴ for an occlusion balloon assembly that may be utilized with any of the preferred occlusion balloon systems described herein, such as the first preferred occlusion balloon system 10. In this alternative preferred embodiment, the spine 20‴ is connected substantially longitudinally to the external balloon surface 140b‴ of the occlusion balloon 140‴. This further alternative preferred occlusion balloon 140‴ has a similar configuration and function when compared to the first preferred occlusion balloon assembly and the same reference numerals are utilized to identify the same or similar features, with a triple-prime symbol (‴) utilized to distinguish this further alternative preferred embodiment from the first preferred embodiment and the above-identified alternative preferred embodiment of FIGS. 32 and 33. The occlusion balloon 140‴ of this further alternative preferred embodiment includes a longitudinal attachment port 141‴ that extends along a length of the occlusion balloon 140‴, at least where the occlusion balloon 140‴ would come into contact with the internal surfaces VS of the vessel VM. The connection of the spine 20‴ to the occlusion balloon 140‴ at the attachment port 141‴ provides a fluid flow channel between the spine 20‴ and the inside of the occlusion balloon 140‴ such that the spine 20‴ and occlusion balloon 140‴ fill at the same pressure during inflation and are likewise deflated to the same or similar pressures. The spine 20‴ is shown in this further alternative preferred embodiment as having an oval-type shape, but is not so limited and may have nearly any shape that results in flow channels being formed in an inflated or partially inflated configuration to permit partial blood flow past the occlusion balloon 140‴, as was described in detail above.

Figure 36:
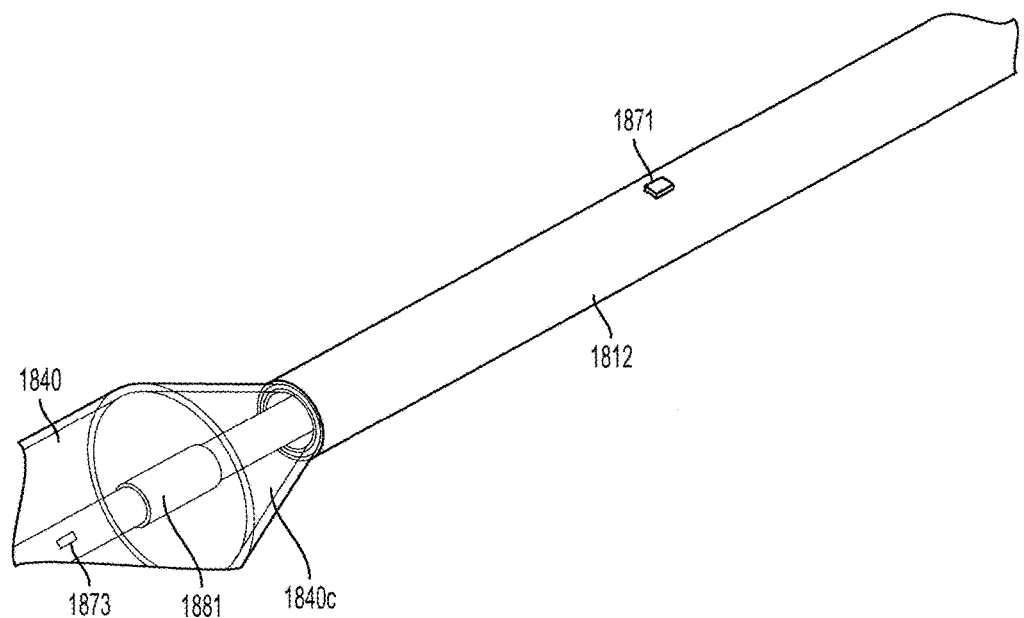
FIG. 36 is a magnified, top perspective view of a proximal portion near a proximal balloon end of an occlusion balloon in accordance with an eighteenth preferred embodiment of the present invention that may be utilized with any of the preferred catheters described herein.
Figure 37:
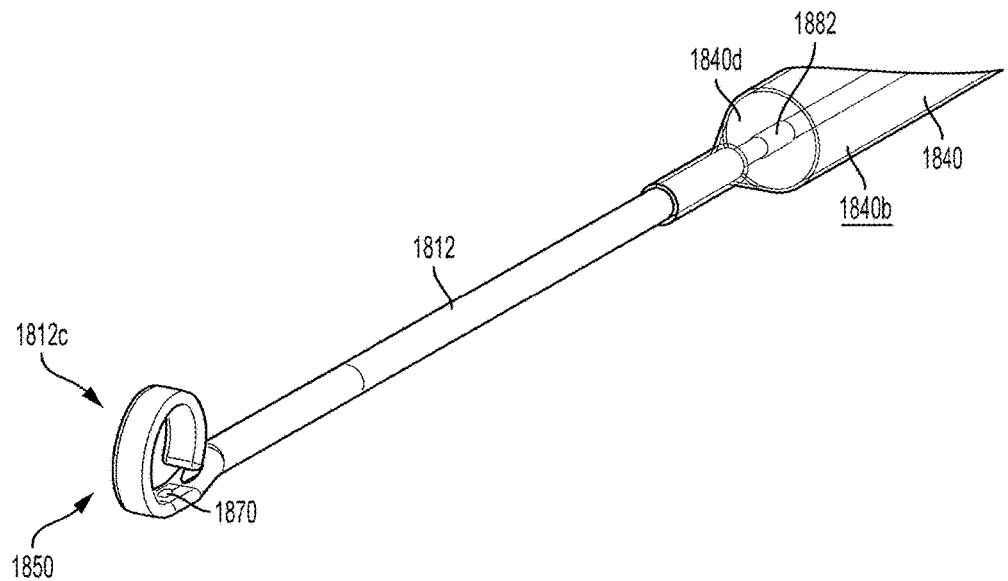
FIG. 37 is a magnified top perspective view of a distal portion of the proximal balloon end of the occlusion balloon catheter system of FIG. 36.
Figure 38:
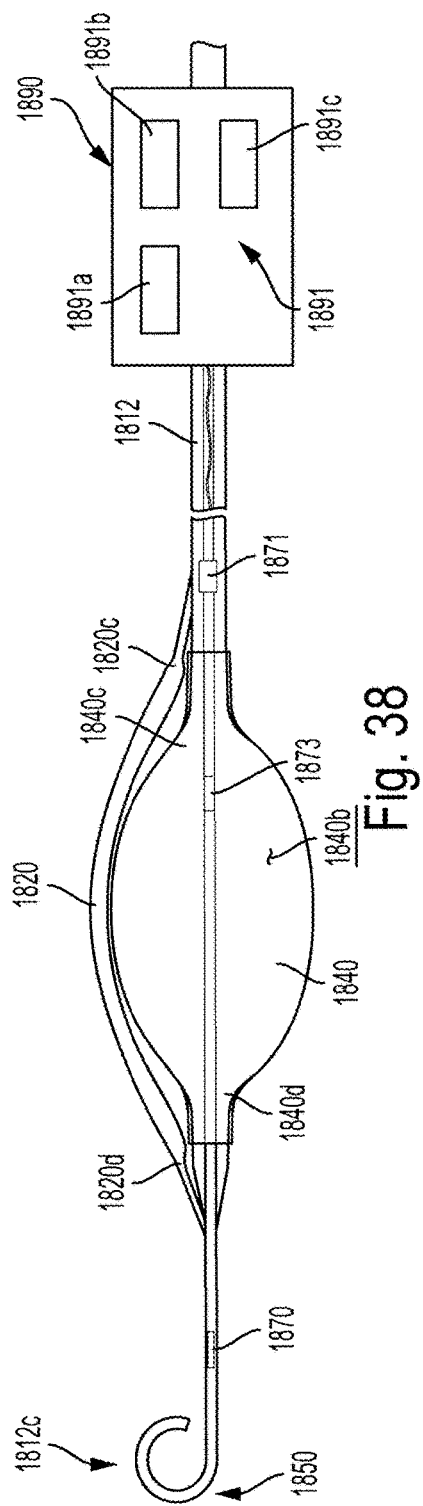
FIG. 38 is a side elevational diagram of an occlusion catheter system in accordance with the eighteenth preferred embodiment of the present invention.
Figure 39:
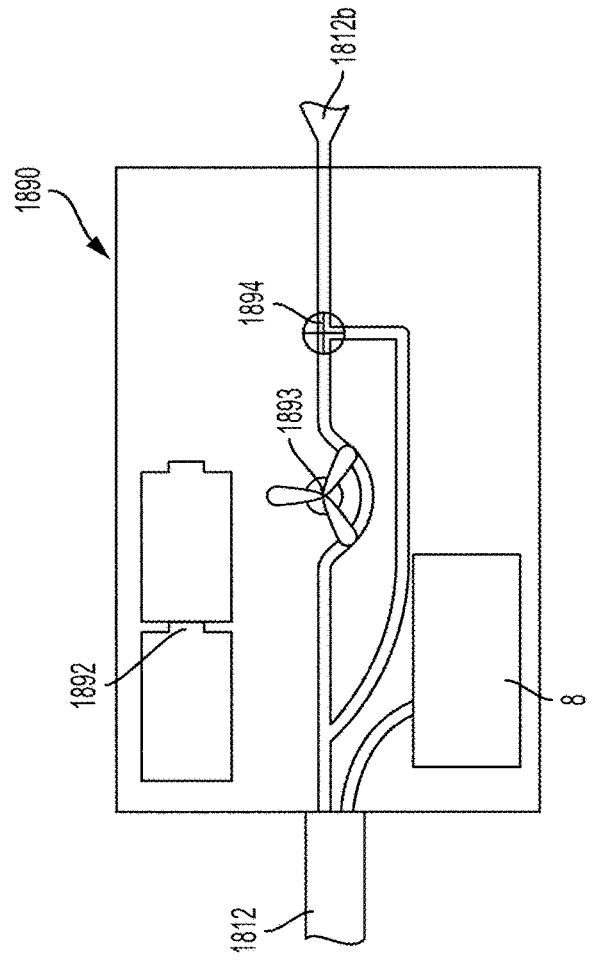
FIG. 39 is a diagram of a controller associated with the occlusion catheter system of FIG. 38.

Referring to FIGS. 36 and 37, an eighteenth preferred embodiment of an occlusion catheter system 1800 includes an inflation catheter member 1812 with an occlusion balloon 1840 mounted thereto. The eighteenth preferred occlusion catheter system 1800 has similar features to the first preferred occlusion catheter system 10 and similar reference numbers are utilized to identify similar features between the first and eighteenth preferred embodiments, with an "18" prefix utilized to distinguish the features of the eighteenth preferred embodiment and the features described in the eighteenth preferred embodiment may be utilized with any of the preferred embodiments described herein. The preferred occlusion catheter system 1800 may also include an inflatable spine 1820, as is shown in FIG. 38.

The eighteenth preferred occlusion catheter system 1800 includes additional components that can be used to electronically display pressures related to the occlusion procedure and manage occlusion with more precision and safety with the preferred system 1800. The preferred occlusion catheter system 1800 includes micro-scale proximal and distal pressure sensors or transducers 1871, 1870 to precisely monitor distal and proximal blood pressure when the occlusion balloon 1840 is inserted in the vessel VW and pressurized to partially or fully inflated configurations. The occlusion catheter system 1800 also preferably monitors the internal pressure in the occlusion balloon 1840 with an internal balloon pressure sensor 1873. These pressure sensors 1870, 1871, 1873 can be used independently for open-loop feedback or with a full-feedback controller device to manage the inflation and deflation of the occlusion balloon 1840.

In the eighteenth preferred embodiment, the proximal and distal electronic pressure sensors 1871, 1870 are incorporated or fixedly attached to the catheter 1812. The proximal pressure sensor 1871 is preferably fixed to the proximal portion of the catheter member 1812 near the proximal end 1840c of the occlusion balloon 1840 and the distal pressure sensor 1870 is mounted to the atraumatic tip 1850 at the distal catheter end 1812c. The electronic pressure sensors 1871, 1870, 1873 are preferably comprised of micro-scale pressure transducers 1871, 1870, 1873 that can be incorporated into or fixedly attached to the catheter member 12. These pressure sensors 1871, 1870, 1873 can sense blood pressure distal and proximal to the occlusion balloon 1840, respectively and within the occlusion balloon 1840. The output of the sensors 1871, 1870, 1873 is preferably used to monitor patient blood pressure during procedures associated with the occlusion catheter system 1800. The pressure sensors 1871, 1870, 1873 are not limited to placements, as shown in FIGS. 36 and 37, and may be otherwise placed on the catheter member 1812 or the occlusion catheter system 1810 to sense pressures or other patient parameters that are utilized to monitor the related procedures. The catheter member 1812 also preferably includes occlusion balloon radiopaque markers 1881, 1882 near ends of the working portion of the occlusion balloon 1840 at transitions to the proximal and distal balloon ends 1840c, 1840d so that a technician is able to visualize placement of occlusion balloon 1840 in the vessel VW using visualization techniques, such as X-ray or fluoroscopy.

Referring to FIGS. 36-39, in use, the eighteenth preferred occlusion catheter system 1800 is inserted at least partially into the vessel VW such that the occlusion balloon 1840 is positioned at the preferred location. The preferred location may be monitored by visualization techniques and location of the radiopaque markers 1881, 1882. The occlusion balloon 1840 is inflated to the partially or fully inflated configuration to provide partial or full occlusion of the vessel VW, depending on the treatment or physician preferences. The pressure sensors 1871, 1870, 1873 transmit signals to the controller 8 and the pressures are preferably displayed as pressure readings on a small display screen 1891 mounted to the occlusion catheter system 1800 by a control hub 1890. The control hub 1890 is preferably mounted on the proximal portion of the catheter member 1812 and includes the integrated LCD screen 1891 to display the pressures from the pressure sensors 1870, 1871, 1873.

Monitoring the pressures displayed on the display screen 1891 allows the user to observe blood pressure responses to the various inflation configurations of the occlusion balloon 1840, in real time and in a convenient location, as the pressurization of the occlusion balloon 1840 is modified. The positioning of the control hub 1890 with the display screen 1891 thereon is preferred, versus a vital monitor that may or may not be conveniently located relative to the procedure for observation by the technician or physician. The display of the pressures from the pressure sensors 1870, 1871, 1873 on the display screen 1891, which may include a first display 1891a, a second display 1891b and a third display 1891c, with a localized signal processor acts as a means for open-loop feedback of the occlusion catheter system 1800. The first display 1891a may display the pressure inside the occlusion balloon 1840 from the internal balloon pressure sensor 1873, the second display 1891b may display the pressure proximally of the occlusion balloon 1840 from the proximal pressure sensor 1871 and the third display 1891c may display the pressure distally of the occlusion balloon 1840 from the distal pressure sensor 1870. The senor 1870, 1871, 1873 data may also be transmitted to a central processor in a wired or wireless manner for depiction, manipulation and/or processing. For example, the collected data may be wirelessly transmitted to a remote central processor for storage and depiction on a larger display, such as a television screen, tablet, vital sign monitor or related equipment for viewing by a larger audience, manipulation and recording or storage. The display 1891 may also include other collected data or calculated information for the user, such as a pressure ratio between the distal and proximal pressure sensors 1870, 1871, an indication of the degree or percentage of occlusion based on an algorithm that uses the proximal and distal pressures to provide an approximation of the degree of occlusion. The degree of occlusion could be displayed as a percentage, on a scale, such as 1-5, as a dial gauge or in other manners that provide an estimation of the degree of occlusion to the user.

The control hub 1890 preferably includes the controller 8, a power source 1893, a pump 1893 and a valve 1894 therein. The valve 1894 is preferably utilized to switch from a manual pressurization at the proximal catheter end 1812b to a mechanical pressurization technique utilizing the pump 1893. The power source 1892 is preferably comprised of a battery or batteries stored in the control hub 1890 and power the pump 1893 and the display screen 1891. The controller 8 may include a circuit board to process signals, make calculations related to the collected data, control the operating components and perform related functions described herein.

In a non-limiting, preferred example, as conditions change within the patient with the occlusion balloon 1840 positioned in the vessel VW and in the partially or fully inflated configurations, the sensors 1870, 1871, 1873 provide passive feedback to the practitioner to indicate the need for changes to the occlusion balloon's 1840 volume to manage blood pressure distal and proximal to the occlusion balloon 1840. If the occlusion balloon 1840 is inflated in a constricted vessel VW, occlusion may be lost as the vessel VW relaxes and the passive feedback can indicate to the practitioner that additional volume or pressure is required in the occlusion balloon 1840 to maintain occlusion.

In an additional non-limiting example, the vessel VW may be partially occluded by forming the blood flow channels 21 to permit limited blood flow around the occlusion balloon 1840. This partial occlusion (pREBOA) is a dynamic scenario where the vessel VW is partially occluded, allowing some blood to flow past the occlusion balloon 1840. This partial flow pas the occlusion balloon 1840 creates pressures being sensed by both the proximal and distal pressure sensors 1871, 1870. In use, the distal pressure sensor 1870 is typically going to have the higher pressure, as it will be placed upstream in the arterial vessel VW and the proximal pressure sensor 1871 is typically going to have the lower pressure, as it is placed downstream in the arterial vessel VW past the occlusion balloon 1840 in the blood flow. The pressure ratio, which may provide an estimation of the degree of occlusion of the vessel VW, of the occlusion catheter system 1800 in this situation is the outlet pressure or pressure at the proximal pressure sensor 1871 divided by the inlet pressure or pressure at the distal pressure sensor 1870. This partial occlusion configuration requires additional attention from the practitioner in response to the dynamic circulatory system of the patient. As the patient responds to treatment, the amount of pressure or volume applied to the occlusion balloon 1840 needed to maintain a specified amount of partial occlusion will typically change. Passive feedback can be used to indicate to the user when manual adjustments are required in order to maintain the desired amount of partial occlusion desired. The occlusion catheter system 1800 may also utilize different sensors, such as flow, force, temperature or other sensors, to monitor this partial occlusion configuration to customize the flow for the patient and their condition or treatment. For example, the flow sensor may be utilized to determine how much blood flow is received by the patient's lower extremities when the occlusion balloon 1840 is positioned in the patient's aorta and a timer may be utilized to signal when additional blood flow to the patient's lower extremities is required or preferred before the lower extremities are damaged. Typically, the required time is extended with greater blood flow and lowered with reduced or lowered blood flow.

The controller 8 in the occlusion catheter system 1800 of the eighteenth preferred embodiment may be comprised of a small, mobile controller unit 8. The controller 8 is not so limited and may be positioned remotely from the catheter member 1812 and communicate through wired or wireless channels with the sensors 1870, 1871, 1873. The controller 8 may also communicate with the pump 1893 to introduce pressurized fluid or withdraw fluid from the occlusion and balloon spines 1840, 1820. The controller 8 is preferably connected to the pressure sensors 1870, 1871, 1873 and other sensors, as is described herein, for management of the occlusion state of the occlusion balloon 1840 in a closed loop configuration (full feedback). The controller 8 can be set to maintain the distal and/or proximal pressures or the pressure ratio between the two by continually adjusting the volume or pressure of the fluid introduced into the occlusion balloon 1840 using the preferably small, internal, locally powered pump 1893. The controller 8 may be set to maintain the proximal pressure measured by the proximal pressure sensor 1871 at approximately zero when maintaining full occlusion and at a pressure greater than zero when maintaining partial occlusion through creation of the blood flow channels 21. For partial occlusion, the controller 8 is preferably set to manage the pressure ratio or a pressure ratio within a range, to maintain a user-specified amount of partial occlusion. The controller 8 may also be configured to permit the user to select a distal pressure setpoint that sets a desired pressure for the distal pressure sensor 1870, which is typically the upstream side of the occlusion balloon 1840 when the system 1800 is positioned in the artery. The controller 8 preferably adjusts the occlusion balloon 1840 and/or the balloon spine 20 volume until the setpoint is achieved. The controller 8 may also be based on a proximal side setpoint associated with the proximal pressure sensor 1871 or a target degree of occlusion (i.e. a preferred percentage of occlusion or pressure ratio). The valve 1894 may be utilized to switch between a manual pressurization of the system 1800, wherein pressure is manually introduced and withdrawn by the user, such as with a syringe, and the above-described closed loop feedback configuration, wherein the controller 8 substantially controls the pressure within the occlusion and balloon spines 1840, 1820.

The controller 8, the pressure sensors 1870, 1871, 1873 and any other sensors associated with the occlusion catheter system 1800 or any of the other herein described preferred occlusion catheter systems 10, 50, 50', 1240, 1240', 1400, 1500, 1600, 1700 may include wireless communication transmitters that transmit sensed data to a central server (not shown) or to each other. The controller 8 or other sensors 1870, 1871, 1873 may be connected to each other or to the central server by Bluetooth or other wireless technology. The central server may be comprised of a handheld device, tablet, or other central processor that is able to display the sensed data, store the sensed data or otherwise manipulate the data for immediate or later use. The data may be displayed at the central server in the same or a similar manner to the data depicted on the below-described display screen 1991 of the nineteenth preferred embodiment. The wireless protocol is preferably secured to prevent any unauthorized receipt of the data.

Figure 40:
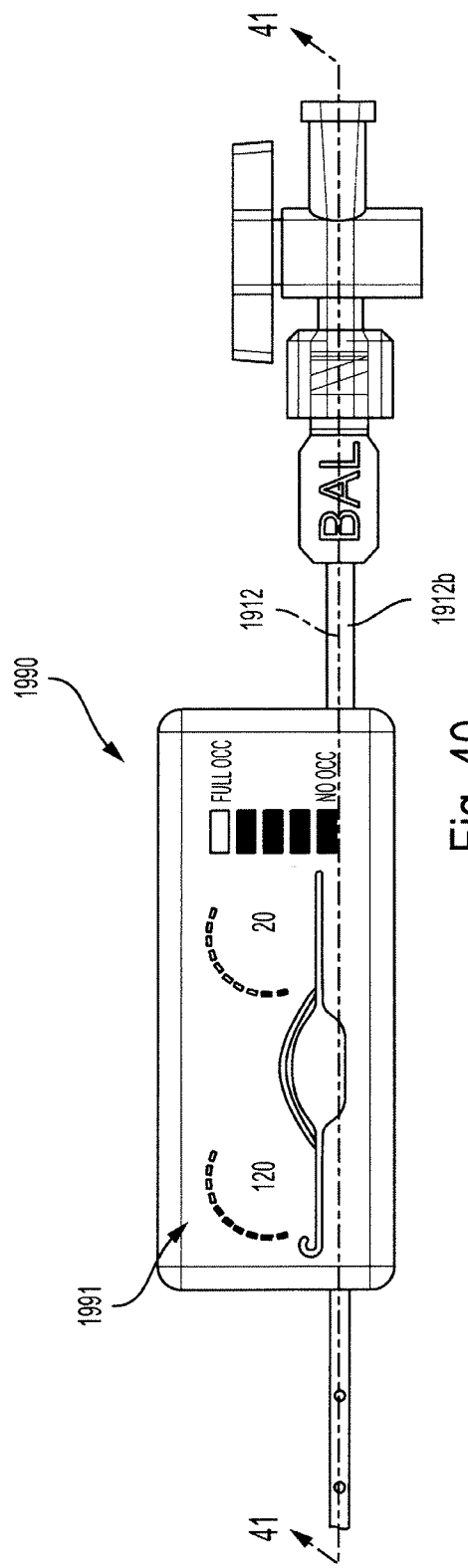
FIG. 40 is a front elevational view of a control hub of a nineteenth preferred embodiment that may be utilized with any of the preferred occlusion catheter systems described herein.
Figure 41:
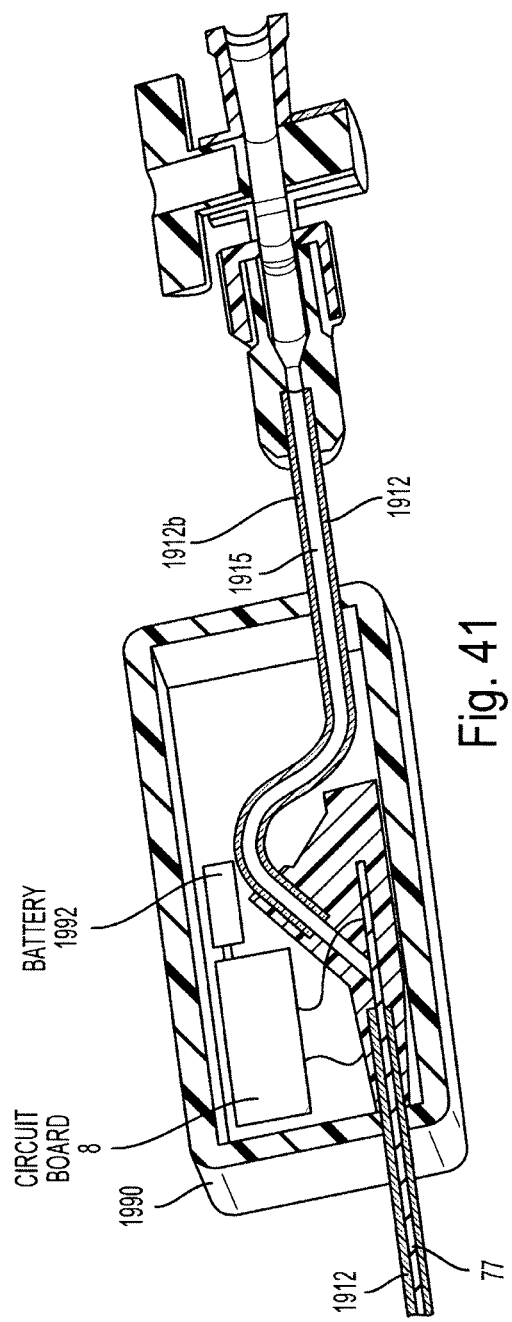
FIG. 41 is a cross-sectional view of the control hub and portions of the occlusion catheter system of FIG. 40, taken along line 41-41 of FIG. 40.
Figure 42:
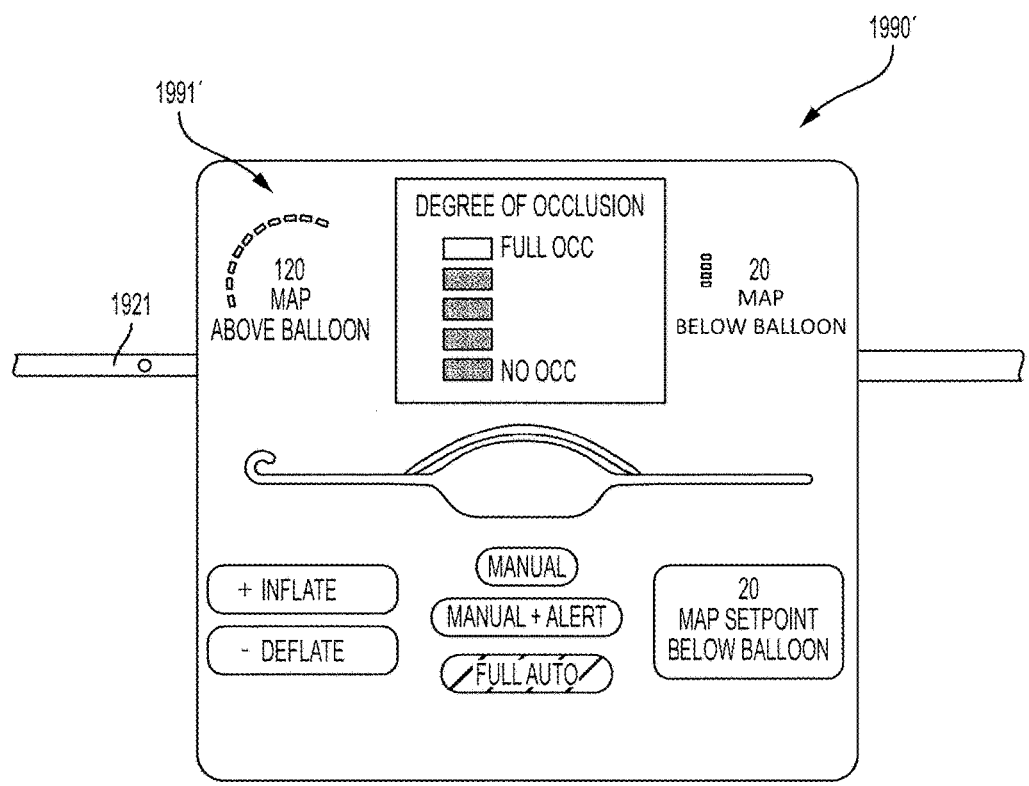
FIG. 42 is a magnified front elevational view of an alternative display for the control hub of FIG. 40.

Referring to FIGS. 40-42, an alternative control hub 1990 in accordance with a nineteenth preferred embodiment may be mounted or attached to any of the preferred occlusion catheter systems described herein. The alternative control hub 1990 and the related occlusion catheter system features shown in FIGS. 40-42 have similarities to the control hub 1800 of the eighteenth preferred embodiment and the occlusion catheter system 10 of the first preferred embodiment and the same reference numbers are utilized for the nineteenth preferred embodiment with a "19" prefix utilized to distinguish the features of the nineteenth preferred embodiment. The alternative control hub 1990 may be fixedly attached to the inflation catheter member 12 near its proximal catheter end 1912b or may be removably attached thereto.

The display screen 1991 of the nineteenth preferred embodiment has a single or first display screen 1991 with multiple depictions thereon. The preferred display screen 1991 shows a representation of the occlusion balloons 140, 140'', 140''', 54, 1240, 320, 540, 440, 640, 740, 840, 1440, 1540, 1640, 1740, 1840 mounted to the catheter members 12, 52, 52', 1244, 1244', 312, 412, 512, 612, 712, 812, 1412, 1512, 1612, 1712, 1812 of any of the preferred embodiments with sensed pressure depicted at the proximal and distal portions of the occlusion balloons 140, 140'', 140''', 54, 1240, 320, 540, 440, 640, 740, 840, 1440, 1540, 1640, 1740, 1840. The display screen 1991 also preferably shows a visual indication of occlusion level in the vessel VW. For example, the display screen 1991 of FIG. 40 shows a pressure of one hundred twenty millimeters of Mercury (120 mmHG) at the distal portion, a pressure of twenty millimeters of Mercury (20 mmHG) at the proximal portion and a nearly full occlusion of the vessel VW. These particular depictions on the display screen 1991 are not limited to including or showing these features, but these preferred representations provide a quick visual reference to the technician to determine the amount of pressure loss resulting from the occlusion within the vessel VW. The visual depiction of the preferred catheters and occlusion balloon with the distal and proximal pressures placed near the distal and proximal portions of the depicted occlusion balloon is intuitively readable and understandable for the medical technician when viewing the display screen 1991 during use.

In the nineteenth preferred embodiment, the control hub 1990 includes the controller or circuit board 8 therein that is powered by the power source or batteries 1992. The controller 8 is preferably in communication with the proximal and distal pressure sensors positioned at proximal and distal sides of the occlusion balloon.

In an alternative nineteenth preferred embodiment, the display screen 1991' may include alternative visual representations of pressures, occlusion degree, controls and settings related to the occlusion catheter systems of the preferred embodiments described herein. The alternative preferred embodiment of the display screen 1991' has similar features when compared to the nineteenth preferred display screen 1991 with a prime symbol ("'") utilized to distinguish the alternative nineteenth preferred embodiment. The nineteenth preferred embodiment display screen 1991' includes the occlusion balloon and catheter member depictions with the inflatable spine attached thereto and pressure indications at the proximal and distal end portions.

A degree of occlusion depiction is positioned between the pressure indications and a lower portion of the display screen 1991' includes controls, including "inflate," "deflate," "manual," "manual+alert," "full auto" and a set point representation. The alternative preferred display screen 1991' is preferably a touch screen such that contacting the "inflate" and "deflate" depictions result in the preferred catheter system inflating or delating one or both of the occlusion balloon and the inflatable spine. The "inflate" and "deflate" depictions or buttons may immediately result in the controller 8 urging pressurized fluid into or drawing fluid out of the preferred occlusion balloon 140 and inflatable spine 20, respectively. The "manual" button results in the controller 8 not controlling the operation of the preferred system 10 and permitting manual inflation and deflation by the user or technician. The "manual+alert" button facilitates manual operation of the preferred occlusion catheter systems, but provides alerts depending on pre-set parameters, such as a maximum internal pressure permitted for the occlusion balloon or inflatable spine, minimum pressure at the proximal end portion of the occlusion balloon or other pre-set parameters that, when exceeded result in a visual and/or audible alarm to notify the user or technician. The "full auto" button results in the controller 8 controlling operation of the preferred occlusion catheter system controlling the operation based on predetermined schedules or programming. The display screen 1991' may also include a running time or clock indicating the amount of time that the occlusion balloon 140 is set at fully occlusion to provide an indication to the physician regarding potential ischemia to downstream tissue and organs in the patient's body. The controller 8 may be programmed to automatically urge the occlusion balloon 140 and the spine 20 to the partially occluded or partially inflated configuration to provide blood flow to the downstream tissues and organs. The display screen 1991' may further include two clocks or timers, one showing the amount of time the system 10 spends in full occlusion and the amount of time the system 10 spends in partial occlusion.

The mean arterial pressure ("MAP") setpoint below balloon provides an indication of a setting indicating that the controller 8 will adjust the downstream or proximal portion pressure to maintain at the level of approximately twenty millimeters of Mercury (20 mmHg) in this particular configuration. The downstream pressure setpoint is not limited to twenty millimeters of Mercury (20 mmHg) and may be otherwise set based on physician and patient requirements, but is preferably set in a range of approximately fifteen to thirty millimeters of Mercury (15-30 mmHg). The controller 8, accordingly, adjusts the volume or pressure in the occlusion balloon 140, 140'', 140''', 54, 1240, 320, 540, 440, 640, 740, 840, 1440, 1540, 1640, 1740, 1840 and/or the spine 20,

20''', 20'''', 1820 until the proximal portion pressure is approximately twenty millimeters of Mercury (20 mmHg). Setting the proximal portion pressure to a predetermined pressure may be proportionally related to blood flow downstream of the occlusion balloon 140, which the physician may utilize to avoid ischemia to lower body organs and tissue during the preferred procedure. The controller 8 may concurrently or separately be configured or programmed to maintain the distal pressure from the distal pressure sensor 170 between ninety and one hundred fifty millimeters of Mercury (90-150 mmHg) to prevent excessively high or low pressure on the upstream side of the occlusion balloon 140. The alternative preferred display screen 1991' is not limiting and the display screen 1991' may be otherwise arranged or configured to provide useful visual information to the technician during use of the system.

Figure 43:
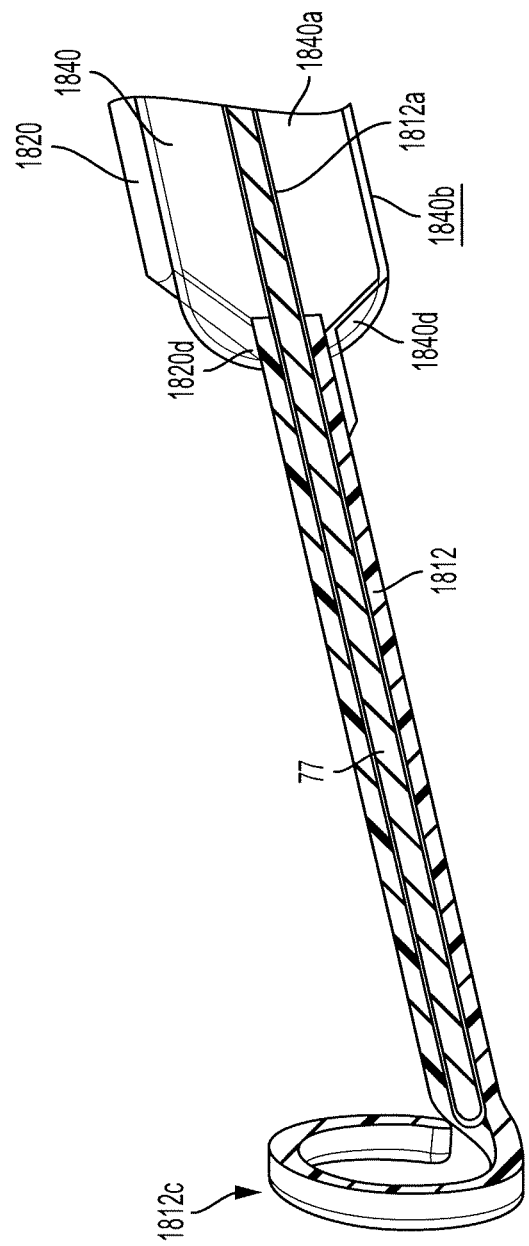
FIG. 43 is a cross-sectional view of a distal portion of an inflation catheter member that may be utilized with any of the preferred inflation catheter systems described herein.

Referring to FIGS. 41 and 43, the preferred systems may include a metallic center rod 77 that is positioned in the hypotube lumen 15 of the stiffener member 1812a. The center rod 77 may be positioned in the hypotube lumen 15 when the hypotube lumen 15 is not being utilized for guidewires, pressure sensing or other functional reasons related to the preferred systems to prevent blood from pooling and clotting in the hypotube lumen 15. The preferred systems are not limited to including the center rod 77, the center rod 77 being metallic and may function or be constructed of other materials without significant impact to the use of the center rod 77. The center rod 77 may, for example, be constructed of a polymeric material that is at least partially flexible for insertion in the hypotube lumen 15.

Figure 44:
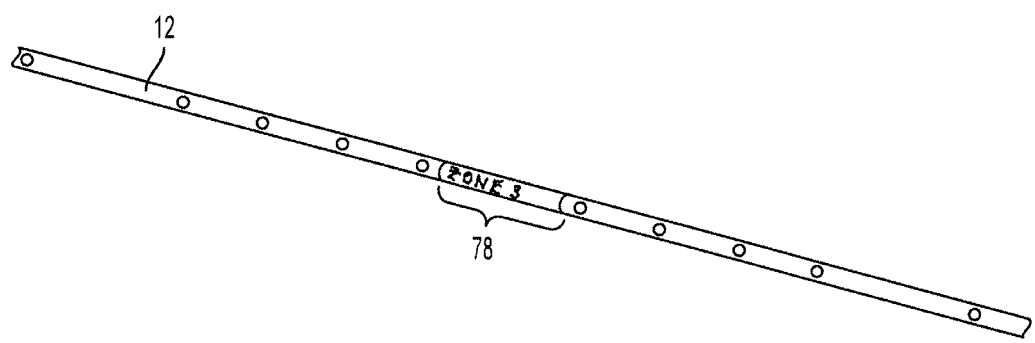
FIG. 44 is a side perspective view of a proximal portion of an inflation catheter member that may be utilized with any of the preferred inflation catheter systems described herein.
Figure 45:
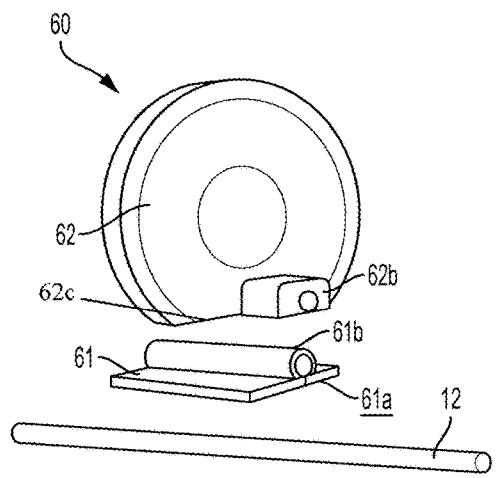
FIG. 45 is a partially exploded, front perspective view of a preferred quick securing device that may be utilized with any of the preferred occlusion catheter systems described herein.
Figure 46:
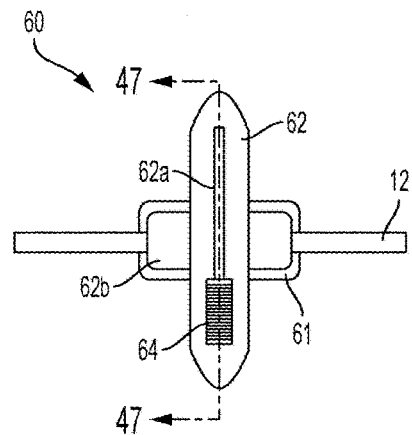
FIG. 46 is a top plan view of the quick securing device of FIG. 45, wherein the device is in an unsecured configuration.
Figure 47:
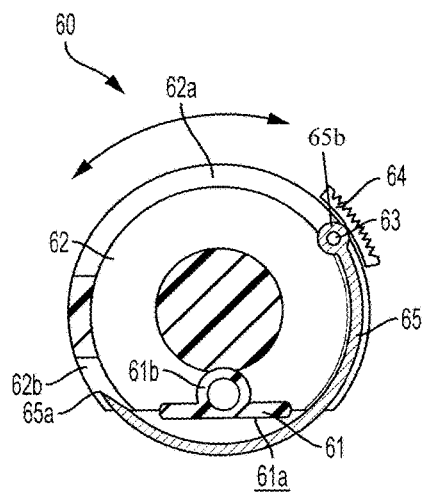
FIG. 47 is a cross-sectional view of the quick securing device of FIG. 45, taken along line 47-47 of FIG. 46, wherein the device is in a secured configuration.
Figure 48:
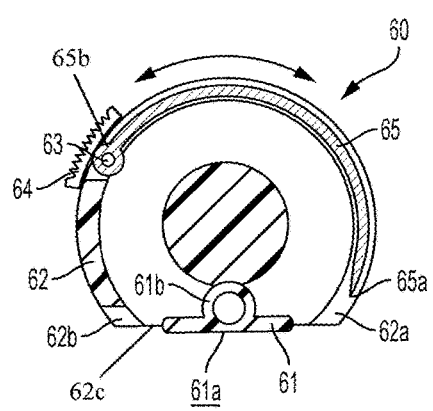
FIG. 48 is a cross-sectional view of the quick securing device of FIG. 45, taken along line 47-47 of FIG. 46, wherein the device is in an unsecured configuration.

Referring to FIG. 44, any of the proximal portions of the preferred inflation catheter members 12, 52, 52', 1244, 1244', 312, 412, 512, 612, 712, 812, 1412, 1512, 1612, 1712, 1812 may include visual indicator marks thereon indicating the depth or distance the occlusion balloon 140, 140'', 140''', 54, 1240, 320, 540, 440, 640, 740, 840, 1440, 1540, 1640, 1740, 1840 is inserted into the patient. The visual indicators may include a zone indicator 78 that provides a range of depth indicating when the occlusion balloon 140, 140'', 140''', 54, 1240, 320, 540, 440, 640, 740, 840, 1440, 1540, 1640, 1740, 1840 is likely in a particular zone of the aorta. The zones of the aorta are described in FIGS. 13 and 14 and the related specification sections of US Patent Application Publication No. 2014/0243873, titled, "Fluoroscopy Independent Balloon Guided Occlusion Catheter and Method," the contents of which are incorporated herein by reference. The zone indicator 78 of FIG. 44 is a "zone 3" indicator and provides a visual indication to the user, when positioned at the entry level of the patients skin, regarding where the occlusion balloon 140, 140'', 140''', 54, 1240, 320, 540, 440, 640, 740, 840, 1440, 1540, 1640, 1740, 1840 is located within the patient, preferably, within which zone the occlusion balloon 140, 140'', 140''', 54, 1240, 320, 540, 440, 640, 740, 840, 1440, 1540, 1640, 1740, 1840 is located; here zone 3. In use, the user inserts the catheter member 12, 52, 52', 1244, 1244', 312, 412, 512, 612, 712, 812, 1412, 1512, 1612, 1712, 1812 into the patient until the zone indicator 78 is positioned at the skin level, which provides a visual indication to the user that the occlusion balloon 140, 140'', 140''', 54, 1240, 320, 540, 440, 640, 740, 840, 1440, 1540, 1640, 1740, 1840 is located at or near the referenced zone of the aorta of the zone indicator 78. The zone indicator 78 is not limited to representing zone 3 and may be configured for zones 1 and 2 and the catheter member 12, 52, 52', 1244, 1244', 312, 412, 512, 612, 712, 812, 1412, 1512, 1612, 1712, 1812 may include each of the zone 1, 2 and 3 indicators thereon. In addition, the zone indicator 78 may be adapted for use with different vessels VW of the patient's body and, therefore, different preferred inflation locations for the occlusion balloon 140.

The zones of the aorta referenced herein preferably include zone 1, which extends from the original of the left subclavian artery to the celiac artery, zone 3, which extends from the lowest renal artery to the aortic bifurcation and zone 2, which comprises portions of the aortic artery between zones 1 and 3. In a young male, the diameter of the vessel VW in zone 1 is approximately twenty millimeters (20 mm), in zone 3 is approximately fifteen millimeters (15 mm) and in zone 2 is between fifteen and twenty millimeters (15-20 mm).

Referring to FIGS. 45-48, the preferred occlusion catheter systems and the associated inflation catheter members 12, 52, 52', 1244, 1244', 312, 412, 512, 612, 712, 812, 1412, 1512, 1612, 1712, 1812 may be secured to the patient by a rapid catheter securement device or mechanism 60 that secures the substantially cylindrical catheter 12, 52, 52', 1244, 1244', 312, 412, 512, 612, 712, 812, 1412, 1512, 1612, 1712, 1812, preferably the proximal portion of the catheter 12, 52, 52', 1244, 1244', 312, 412, 512, 612, 712, 812, 1412, 1512, 1612, 1712, 1812 to a patient 60. The catheter securing member 60 is described herein as securing the inflation catheter member 12 of the first preferred embodiment to the patient for simplicity, but may be used with any of the preferred inflation catheter members 12, 52, 52', 1244, 1244', 312, 412, 512, 612, 712, 812, 1412, 1512, 1612, 1712, 1812, without significantly impacting the design and function of the securement device 60.

The catheter securing mechanism 60 includes a base member 61 that is removably attachable to the inflation catheter member 12, a needle housing 62 that is removably attachable to the base member 61, a movable needle holder 63 that is pivotable relative to the needle housing 62, an operation handle 64 attached to the needle holder 63 and an arcuate needle 65 secured to the needle holder 63 and the operation handle 64. The base member 61 is preferably slidable along the proximal portion of the catheter member 12 so that it can be adjusted for positioning near a puncture in the patient where the catheter member 12 is introduced into the patient. The needle 65 and needle holder 63 are slidably mounted in an arcuate housing slot 62a that guides the needle 65 and needle holder 63 in an arcuate path proximate to an arcuate edge of the needle housing 62. The needle housing 62 and the base member 61 are preferably constructed of a biocompatible, substantially rigid polymeric material that is able to take on the general size and shape of the needle housing 62 and the base member 61. The base member 61 is able to snap fit or slide and engage the inflation catheter member 12 and the base member 61 is in-turn snap fit or securable to the needle housing 62.

The base member 61 preferably includes a skin facing surface 61a and a tubular engagement mechanism 61b. The tubular engagement mechanism 61b snap fits or is otherwise securable to the inflation catheter member 12 for movement along its length. The needle housing 62 includes a base boss 62b and a generally frusta-circular or frusta-disc shape with the base boss 62b positioned on a substantially flat lower side 62c of the needle housing 62. The base boss 62b is preferably able to snap fit or otherwise attach to the tubular engagement mechanism 61b to secure the base member 61 to the needle housing 62 in an assembled configuration.

In use, any of the preferred occlusion catheter systems with the associated the catheter members 12, 52, 52', 1244, 1244', 312, 412, 512, 612, 712, 812, 1412, 1512, 1612, 1712,

1812 are inserted into the patient with the occlusion balloon 140, 140'', 140''', 54, 1240, 320, 540, 440, 640, 740, 840, 1440, 1540, 1640, 1740, 1840 inserted into the vessel VW at the predetermined location. The base member 61 is engaged to attached to the proximal portion of the catheter member 12, 52, 52', 1244, 1244', 312, 412, 512, 612, 712, 812, 1412, 1512, 1612, 1712, 1812 with the tubular engagement mechanism 61b engaged around the catheter member 12, 52, 52', 1244, 1244', 312, 412, 512, 612, 712, 812, 1412, 1512, 1612, 1712, 1812 and the skin facing surface 61a facing or in facing engagement with the patient's skin. The base member 61 is preferably slidable along the catheter member 12 so that the base member 61 can be moved away from an insertion puncture during insertion and then moved to a position proximate the puncture to anchor the catheter member 12 to the patient. The housing 62 is then snap fit or otherwise engaged to the base member 61 by securing the base boss 62b to the tubular engagement mechanism 61b with the needle 65, the needle holder 63 and the operation handle 64 in an initial position (FIGS. 46 and 48) in the housing slot 62a. In the initial position, a needle tip 65a is positioned within and covered by the housing 62 to prevent or reduce the likelihood of inadvertent needle sticks. The needle 65 also has a needle base end 65b that is securely mounted to the operation handle 64.

The assembled base member 61, inflation catheter member 12 and needle housing 62 may be mechanically secured together by fasteners, clips, adhesive bonding or other engagement mechanisms or may be secured by the snap fit described above. The assembled catheter securing mechanism 60 is moved to a position close to the puncture in the patient and the skin facing surface 61a is placed on the patient's skin near the puncture. The user then grasps the operation handle 64 and urges the movable needle holder 63 and the needle 65 in an arcuate motion along the housing slot 62a. The tip 65a of the needle 65 pierces the patient's skin as the needle 65, needle holder 63 and operation handle are guided to the secured position (FIG. 47) by the housing slot 62a. The needle 65 secures the assembly to the patient's skin to prevent or limit movement of the catheter member 12, 52, 52', 1244, 1244', 312, 412, 512, 612, 712, 812, 1412, 1512, 1612, 1712, 1812 relative to the patient such that the occlusion balloon 140, 140'', 140''', 54, 1240, 320, 540, 440, 640, 740, 840, 1440, 1540, 1640, 1740, 1840 generally does not move from its preferred position. In the secured position, the tip 65a is positioned in an end slot 62b that covers the tip 65a and prevents or limits potential needle pricks. The arcuate-shape of the needle 65 facilitates movement along the housing slot 62a and extension of the needle 65 out of the needle housing 62 into the patient's skin in the secured position.

Following completion of the procedure, the user grasps the operation handle 64 and moves the operation handle 64, the needle holder 63 and the needle 65 from the secured position back to the initial position, guided by the housing slot 62a. The user is then able to remove the catheter securing member 60 from the catheter member 12, 52, 52', 1244, 1244', 312, 412, 512, 612, 712, 812, 1412, 1512, 1612, 1712, 1812 from the patient. The preferred occlusion catheter member is then removed from the patient. The preferred needle 65 has a semi-circular profile, extending along an approximately one hundred eighty degree (180°) arc and rotating through a slightly less than one hundred eighty degree (180°) arc between the initial position and the secured position.

The rapid catheter securement device or member 60 for securing the substantially cylindrical catheter 12, 52, 52', 1244, 1244', 312, 412, 512, 612, 712, 812, 1412, 1512, 1612, 1712, 1812, preferably the proximal portion of the catheter 12, 52, 52', 1244, 1244', 312, 412, 512, 612, 712, 812, 1412, 1512, 1612, 1712, 1812 that extends out of the patient in a working position has the base member 61, the needle housing 62 and the arcuate needle 65 that are assembled and engaged to the catheter 12, 52, 52', 1244, 1244', 312, 412, 512, 612, 712, 812, 1412, 1512, 1612, 1712, 1812 to mount the catheter 12, 52, 52', 1244, 1244', 312, 412, 512, 612, 712, 812, 1412, 1512, 1612, 1712, 1812 to the patient. The base member 61 has the skin facing surface 61a and the tubular engagement mechanism 61b. The engagement mechanism 61b is configured to movably engage the catheter 12, 52, 52', 1244, 1244', 312, 412, 512, 612, 712, 812, 1412, 1512, 1612, 1712, 1812 such that the engagement mechanism 61b is movable, preferably slidable, along the proximal portion of the catheter 12, 52, 52', 1244, 1244', 312, 412, 512, 612, 712, 812, 1412, 1512, 1612, 1712, 1812 prior to and during insertion so that the engagement mechanism 61b can be moved close to the incision or puncture in the patient for securing to the patent.

The needle housing 62 has an arcuate housing slot 62a, a base boss 62b and a substantially flat lower side 62c. The needle housing 62, therefore, has a frusta-circular profile cut-off by the flat lower side 62c where the needle housing 62 is positioned at the patient's skin near the entry puncture or incision. The base boss 62b positioned proximate the flat lower side 62c and, therefore, proximate the patient's skin in a mounted configuration.

The arcuate needle 65 has the tip 65a and the needle base end 65b. The needle 65 is movably mounted to the needle housing 62 and is movable along the arcuate housing slot 62a. The needle tip 65a is positioned within the needle housing 62 along the housing slot 62a in an initial position and at least a portion of the needle 65 is positioned outside the needle housing 62 in a secured position proximate the flat lower side 62c. In the preferred embodiment, a middle portion of the needle 65 between the tip 65a and the needle base 65b extends out of the housing beyond the flat lower side 62c and into the patient to secure the catheter securing member 60 and the engaged catheter 12, 52, 52', 1244, 1244', 312, 412, 512, 612, 712, 812, 1412, 1512, 1612, 1712, 1812 to the patient as a result of the needle 65 engaging the patient's skin and soft tissue. The catheter securing member 60, therefore, limits movement of the catheter 12, 52, 52', 1244, 1244', 312, 412, 512, 612, 712, 812, 1412, 1512, 1612, 1712, 1812 relative to the patient when the occlusion balloon 140 and spine 20 are inflated and the pulsatile pressure and flow in the vessel VW applies force to the catheter 12, 52, 52', 1244, 1244', 312, 412, 512, 612, 712, 812, 1412, 1512, 1612, 1712, 1812.

In the preferred embodiment, the engagement mechanism 61b is tubular and wraps around the catheter 12, 52, 52', 1244, 1244', 312, 412, 512, 612, 712, 812, 1412, 1512, 1612, 1712, 1812 in the assembled configuration, providing a slidable engagement so that the base member 61 can be adjusted along the length of the catheter 12, 52, 52', 1244, 1244', 312, 412, 512, 612, 712, 812, 1412, 1512, 1612, 1712, 1812. The tip 65a is preferably positioned within an end slot or base boss 62b when the needle 65 is positioned in the secured position such that the tip 65 is not exposed, but is positioned within the needle housing 62 in the secured position. This positioning of the tip 65 limits exposure of the tip 65a and potential needle sticks for users.

The catheter securing member 60 also preferably includes the operation handle 64 attached to the base end or needle base 65b of the needle 65 opposite the tip 65a. The operation handle 64 is graspable by a user to move the needle 65 from the initial position to the secured position along the arcuate housing slot 62a. The needle holder 63 is movably mounted to the needle housing 62 and is movable along the arcuate housing slot 62a. The needle holder 63 is attached to the base end 65b of the needle 65 opposite the tip 65a. The needle housing 62 includes the base boss 62b proximate the flat lower side 62c. The base boss 62b is removably mountable to the engagement mechanism 61b of the base member 61 and substantially covers the engagement mechanism 61b in the assembled configuration.

It will be appreciated by those skilled in the art that changes could be made to the embodiments described above without departing from the broad inventive concept thereof. For example, any of the preferred occlusion balloons may be configured and adapted for use with any of the preferred occlusion catheter systems described herein by attaching the occlusion balloon or occlusion balloon assembly to the associated catheter of the occlusion catheter system. It is understood, therefore, that this invention is not limited to the particular embodiments disclosed, but it is intended to cover modifications within the spirit and scope of the present invention as defined by the present description.

We claim:

1. An occlusion catheter system for occlusion or partial occlusion of a relatively large vessel having an internal surface, the occlusion catheter system comprising:
   an inflation catheter member having a stiffener member, a first inflation lumen, a proximal catheter end and a distal catheter end, the inflation catheter member defining a longitudinal axis, the inflation catheter member having an atraumatic tip on the distal catheter end;
   an occlusion balloon having an internal balloon space, an external balloon surface, a proximal balloon end and a distal balloon end, the proximal and distal balloon ends connected to the inflation catheter between the proximal catheter end and the distal catheter end, the occlusion balloon substantially centered along the longitudinal axis in an inflated configuration, the first inflation lumen being in fluid communication with the internal balloon space;
   a distal pressure sensor attached to the inflation catheter member between the distal balloon end and the atraumatic tip; and
   an inflatable spine having an internal spine space, an external spine surface, a proximal spine end and a distal spine end, the proximal and distal spine ends connected to the inflation catheter, a portion of the external balloon surface contacting the external spine surface when the occlusion balloon and the inflatable spine are in an inflated configuration, the proximal spine end connected to the inflation catheter near the proximal balloon end and the distal spine end connected to the inflation catheter near the distal balloon end, the occlusion balloon and the inflatable spine configured to define blood flow channels with the internal surface and the external balloon surface when the occlusion catheter system is at least partially positioned in the vessel and the occlusion balloon and the inflatable spine are in a partially inflated configuration, the inflatable spine has a substantially constant spine diameter between the proximal spine end and the distal spine end in partially and fully inflated configurations.

2. The occlusion catheter system of claim 1 wherein the occlusion balloon has an occlusion diameter, the occlusion diameter being at least twice the spine diameter when the occlusion balloon and the inflatable spine are inflated at a partial inflation pressure.

3. The occlusion catheter system of claim 1, wherein the first inflation lumen is in fluid communication with the inflatable spine.

4. The occlusion catheter system of claim 1, wherein the inflation catheter member includes a second inflation lumen, the second inflation lumen being in fluid communication with the inflatable spine.

5. The occlusion catheter system of claim 1, wherein the occlusion balloon is constructed of a compliant polymeric material and the inflatable spine is constructed of a non-compliant material.

6. The occlusion catheter system of claim 1, wherein the pressure sensor is comprised of an electronic pressure sensor.

7. The occlusion catheter system of claim 1, wherein the pressure sensor is comprised of a distal side port in the inflation catheter member, the stiffener member including a lumen therein, the distal side portion in fluid communication with the lumen in the stiffener member.

8. The occlusion catheter system of claim 7, wherein the stiffener member is comprised of a hypotube and the lumen is comprised of a hypotube lumen.

9. The occlusion catheter system of claim 8, wherein the hypotube is constructed of a nitinol material.

10. The occlusion catheter system of claim 1, wherein the occlusion balloon and the inflatable spine are configured such that the occlusion balloon over-drives and substantially flattens the inflatable spine against the internal surface in the fully inflated configuration.

11. The occlusion catheter system of claim 1, wherein the atraumatic tip is comprised of a generally flattened cylinder having two generally planar opposing surfaces.

12. The occlusion catheter system of claim 1, further comprising:
   a proximal pressure sensor mounted to the catheter member proximally relative to the occlusion balloon.

13. The occlusion catheter system of claim 12, further comprising:
   a controller in communication with the proximal and distal pressure sensors; and
   a pump in fluid communication with the occlusion balloon and the inflatable spine, the controller configured to one of introduce pressurized fluid into the occlusion balloon and the inflatable spine and withdraw fluid from the occlusion balloon and the inflatable spine based on pressure measurements from the proximal and distal pressure sensors.

14. The occlusion catheter system of claim 1, further comprising:
   a control hub mountable to the catheter member near the proximal catheter end, the control hub including a display screen and a power source, the control hub configured to depict pressure on the display screen from the distal pressure sensor.

15. An occlusion catheter system for occlusion or partial occlusion of a relatively large vessel having an internal surface, the occlusion catheter system comprising:
   an inflation catheter member having a stiffener member, a first inflation lumen, a second inflation lumen, a proximal catheter end and a distal catheter end, the inflation catheter member defining a longitudinal axis, the inflation catheter member having an atraumatic tip on the distal catheter end;

an occlusion balloon having an internal balloon space, an external balloon surface, a proximal balloon end and a distal balloon end, the proximal and distal balloon ends connected to the inflation catheter between the proximal catheter end and the distal catheter end, the occlusion balloon substantially centered along the longitudinal axis in an inflated configuration, the first inflation lumen being in fluid communication with the internal balloon space;

a distal pressure sensor attached to the inflation catheter member between the proximal balloon end and the atraumatic tip; and an inflatable spine having an internal spine space, an external spine surface, a proximal spine end and a distal spine end, the proximal and distal spine ends connected to the inflation catheter, the internal spine space being in fluid communication with the second inflation lumen, a portion of the external balloon surface contacting the external spine surface when the occlusion balloon and the inflatable spine are in an inflated configuration, the proximal spine end connected to the inflation catheter near the proximal balloon end and the distal spine end connected to the inflation catheter near the distal balloon end, the inflatable spine has a substantially constant spine diameter between the proximal spine end and the distal spine end in partially and fully inflated configurations.

16. The occlusion catheter system of claim 15, wherein the occlusion balloon is constructed of a compliant polymeric material and the inflatable spine is constructed of a non-compliant material.

17. The occlusion catheter system of claim 16, wherein the occlusion balloon is constructed of a compliant first polyurethane material and the inflatable spine is constructed of non-compliant second polyurethane material, the first polyurethane material having a first durometer and the second polyurethane material having a second durometer, the second durometer being greater than the first durometer.

18. The occlusion catheter system of claim 15, wherein the occlusion balloon and the inflatable spine are configured to define blood flow channels with the internal surface and the external balloon surface when the occlusion catheter system is at least partially positioned in the vessel and the occlusion balloon and the inflatable spine are in the partially inflated configuration.

19. The occlusion catheter system of claim 15, wherein the occlusion balloon and the inflatable spine are configured such that the occlusion balloon over-drives and substantially flattens the inflatable spine against the internal surface in the fully inflated configuration.

20. The occlusion catheter system of claim 15, wherein the inflation catheter member includes a stiffener member extending substantially coaxially and substantially defining the longitudinal axis.

21. The occlusion catheter system of claim 20, wherein the stiffener member is comprised of a hypotube.

22. The occlusion catheter system of claim 15, wherein the pressure sensor is comprised of an electronic pressure sensor.

23. The occlusion catheter system of claim 15, further comprising:
a proximal pressure sensor mounted to the catheter member proximally relative to the occlusion balloon.

24. The occlusion catheter system of claim 23, further comprising:
a controller in communication with the proximal and distal pressure sensors; and
a pump in fluid communication with the occlusion balloon and the inflatable spine, the controller configured to one of introduce pressurized fluid into the occlusion balloon and the inflatable spine and withdraw fluid from the occlusion balloon and the inflatable spine based on pressure measurements from the proximal and distal pressure sensors.

25. The occlusion catheter system of claim 15, further comprising:
a control hub mountable to the catheter member near the proximal catheter end, the control hub including a display screen and a power source, the control hub configured to depict pressure on the display screen from the distal pressure sensor.

* * * * *